(12) United States Patent
Kamath et al.

(10) Patent No.: US 12,143,386 B2
(45) Date of Patent: Nov. 12, 2024

(54) DIABETES MANAGEMENT PARTNER INTERFACE FOR WIRELESS COMMUNICATION OF ANALYTE DATA

(71) Applicant: Dexcom, Inc., San Diego, CA (US)

(72) Inventors: Apurv Ullas Kamath, San Diego, CA (US); Michael Robert Mensinger, San Diego, CA (US); Nicholas Polytaridis, San Diego, CA (US); Gary A. Morris, San Diego, CA (US); Alexandra Elena Constantin, San Jose, CA (US); Douglas William Burnette, San Diego, CA (US); Mario Remon, Ft. Lauderdale, FL (US); Jorge R. Barreras, Miami, FL (US); Benjamin Elrod West, San Diego, CA (US); Christopher Robert Hannemann, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 18/484,256

(22) Filed: Oct. 10, 2023

(65) Prior Publication Data

US 2024/0039921 A1 Feb. 1, 2024

Related U.S. Application Data

(63) Continuation of application No. 17/661,739, filed on May 2, 2022, now Pat. No. 11,818,133, which is a
(Continued)

(51) Int. Cl.
*H04L 9/40* (2022.01)
*A61B 5/00* (2006.01)
(Continued)

(52) U.S. Cl.
CPC ........ *H04L 63/101* (2013.01); *A61B 5/14532* (2013.01); *A61B 5/686* (2013.01);
(Continued)

(58) Field of Classification Search
CPC ..... H04L 63/101; G16H 10/65; H04W 76/14; A61B 5/14532
(Continued)

(56) References Cited

U.S. PATENT DOCUMENTS 5,748,882 A 5/1998 Huang
7,294,105 B1 * 11/2007 Islam .................. A61B 5/0006
128/903
(Continued)

FOREIGN PATENT DOCUMENTS

CN 107073207 A 8/2017
JP 2009535715 A 10/2009
(Continued)

OTHER PUBLICATIONS

Daniel A. Domingo-Lopez; Medical devices, smart drug delivery, wearables and technology for the treatment of Diabetes Mellitus; Science direct: pp. 1-5 (Year: 2017).*
(Continued)

*Primary Examiner* — Monjur Rahim
(74) *Attorney, Agent, or Firm* — Patterson + Sheridan, LLP

(57) ABSTRACT

Systems, devices, and methods are disclosed for wireless communication of analyte data. In embodiments, a method of using a diabetes management partner interface to configure an analyte sensor system for wireless communication with a plurality of partner devices is provided. The method includes the analyte sensor system receiving authorization to provide one of the partner devices with access to a set of configuration parameters via the diabetes management part-
(Continued)

ner interface. The set of configuration parameters is stored in a memory of the analyte sensor system. The method also includes, responsive to input received from the one partner device via the diabetes management partner interface, the analyte sensor system setting or causing a modification to the set of configuration parameters, according to a system requirement of the one partner device.

17 Claims, 25 Drawing Sheets

Related U.S. Application Data continuation of application No. 16/169,886, filed on Oct. 24, 2018, now Pat. No. 11,363,025, which is a continuation of application No. 16/169,661, filed on Oct. 24, 2018, now Pat. No. 11,153,317.

(60) Provisional application No. 62/579,061, filed on Oct. 30, 2017.

(51) Int. Cl.
| | |
|---|---|
| A61B 5/145 | (2006.01) |
| G16H 10/60 | (2018.01) |
| G16H 10/65 | (2018.01) |
| G16H 40/40 | (2018.01) |
| G16H 40/63 | (2018.01) |
| G16H 50/20 | (2018.01) |
| H04W 12/06 | (2021.01) |
| H04W 52/02 | (2009.01) |
| H04W 76/14 | (2018.01) |
| A61B 5/1495 | (2006.01) |
| H04W 4/38 | (2018.01) |
| H04W 4/80 | (2018.01) |

(52) U.S. Cl.
CPC .............. *G16H 10/60* (2018.01); *G16H 10/65* (2018.01); *G16H 50/20* (2018.01); *H04W 12/06* (2013.01); *H04W 52/0277* (2013.01); *H04W 76/14* (2018.02); *A61B 5/0002* (2013.01); *A61B 5/0004* (2013.01); *A61B 5/14503* (2013.01); *A61B 5/14546* (2013.01); *A61B 5/1495* (2013.01); *A61B 5/486* (2013.01); *A61B 5/7445* (2013.01); *A61B 5/746* (2013.01); *H04L 2209/88* (2013.01); *H04W 4/38* (2018.02); *H04W 4/80* (2018.02)

(58) Field of Classification Search
USPC ........................................................ 713/168
See application file for complete search history.

(56) References Cited

U.S. PATENT DOCUMENTS

| | | | |
|---|---|---|---|
| 8,579,853 B2 | 11/2013 | Reggiardo et al. | |
| 9,041,730 B2 | 5/2015 | Johnson et al. | |
| 9,136,973 B2 | 9/2015 | Huang et al. | |
| 9,152,784 B2 | 10/2015 | Das et al. | |
| 9,804,148 B2 | 10/2017 | Hayter et al. | |
| D852,837 S | 7/2019 | Mazlish et al. | |
| 10,426,896 B2 | 10/2019 | Desborough et al. | |
| 2005/0283203 A1 | 12/2005 | Flaherty et al. | |
| 2009/0076349 A1* | 3/2009 | Libbus ............... | A61B 5/02055 |
| | | | 600/301 |
| 2010/0161959 A1 | 6/2010 | Sood | |
| 2011/0006876 A1 | 1/2011 | Moberg et al. | |
| 2011/0201911 A1* | 8/2011 | Johnson ............... | A61B 5/0013 |
| | | | 345/173 |
| 2012/0096451 A1 | 4/2012 | Tenbarge et al. | |
| 2012/0322461 A1 | 12/2012 | Ito et al. | |
| 2013/0191513 A1 | 7/2013 | Kamen et al. | |
| 2014/0235984 A1 | 8/2014 | Wilbur et al. | |
| 2014/0369268 A1 | 12/2014 | Huang et al. | |
| 2015/0018633 A1* | 1/2015 | Kovachev ............... | A61B 5/486 |
| | | | 600/301 |
| 2015/0205947 A1 | 7/2015 | Berman et al. | |
| 2015/0207790 A1 | 7/2015 | Lu et al. | |
| 2015/0221194 A1* | 8/2015 | Sarkar ................ | G08B 13/1427 |
| | | | 340/870.16 |
| 2015/0277845 A1* | 10/2015 | Kim ...................... | G06F 3/1462 |
| | | | 345/1.2 |
| 2015/0341438 A1* | 11/2015 | Sloan .................... | A61B 5/0004 |
| | | | 455/41.2 |
| 2016/0055130 A1 | 2/2016 | Bentley et al. | |
| 2016/0057196 A1 | 2/2016 | Bentley et al. | |
| 2016/0066843 A1 | 3/2016 | Mensinger et al. | |
| 2016/0174277 A1* | 6/2016 | Yoon ..................... | H04W 76/14 |
| | | | 370/338 |
| 2016/0183854 A1 | 6/2016 | Lee | |
| 2016/0324463 A1 | 11/2016 | Simpson et al. | |
| 2016/0328577 A1* | 11/2016 | Howley ................. | G16H 20/60 |
| 2017/0055890 A1 | 3/2017 | Kube et al. | |
| 2017/0080207 A1 | 3/2017 | Perez et al. | |
| 2017/0173262 A1 | 6/2017 | Veltz | |
| 2017/0181628 A1 | 6/2017 | Burnette et al. | |
| 2017/0189614 A1* | 7/2017 | Mazlish .............. | A61M 5/1452 |
| 2017/0203030 A1* | 7/2017 | Brewer ............. | A61M 5/14244 |
| 2017/0281000 A1 | 10/2017 | Wedekind et al. | |
| 2018/0000395 A1 | 1/2018 | Lucisano et al. | |
| 2018/0047228 A1 | 2/2018 | Hyde et al. | |
| 2018/0085532 A1* | 3/2018 | Desborough .......... | G16H 50/20 |
| 2018/0121610 A1* | 5/2018 | Cayle ..................... | G16H 40/20 |
| 2018/0125689 A1* | 5/2018 | Perez ................. | A61N 1/36014 |
| 2018/0144817 A1 | 5/2018 | Lofgren et al. | |
| 2018/0172664 A1 | 6/2018 | Love et al. | |
| 2018/0279911 A1 | 10/2018 | Lucisano et al. | |
| 2019/0116088 A1 | 4/2019 | Mueglitz et al. | |
| 2019/0125224 A1 | 5/2019 | Kamath et al. | |
| 2019/0132801 A1 | 5/2019 | Kamath et al. | |
| 2019/0173885 A1 | 6/2019 | Kamath et al. | |
| 2019/0246357 A1 | 8/2019 | Cole et al. | |
| 2023/0293060 A1 | 9/2023 | Duvall et al. | |

FOREIGN PATENT DOCUMENTS

| | | |
|---|---|---|
| JP | 2017503619 A | 2/2017 |
| WO | 2016207206 A1 | 12/2016 |

OTHER PUBLICATIONS

Fortino G., et al., "BodyCloud: Integration of Cloud Computing and Body Sensor Networks," 2012, IEEE 4th International Conference on Cloud Computing Technology Science, 2012, 6 pages.
International Preliminary Report on Patentability for Application No. PCT/US2018/057390 mailed May 14, 2020, 18 pages.
International Search Report and Written opinion for Application No. PCT/US2018/057390 mailed Feb. 21, 2019, 20 pages.
Nathaniel D., et al., "A Digital Ecosystem of Diabetes Data and Technology: Services, Systems, and Tools Enabled by Wearables, Sensors, and Apps," Journal of Diabetes Science and Technology, 2016, vol. 10, No. 1, pp. 35-41.
Valavanis E., et al., "MobiShare: Sharing Context-Dependent Data Services from Mobile Sources," IEEE: 2003, pp. 1-8.
Zarkogianni K., et al., "A Review of Emerging Technologies for the Management of Diabetes Mellitus," IEEE Transactions on Biomedical Engineering, Dec. 2015, vol. 62, No. 12, pp. 2735-2749.

* cited by examiner

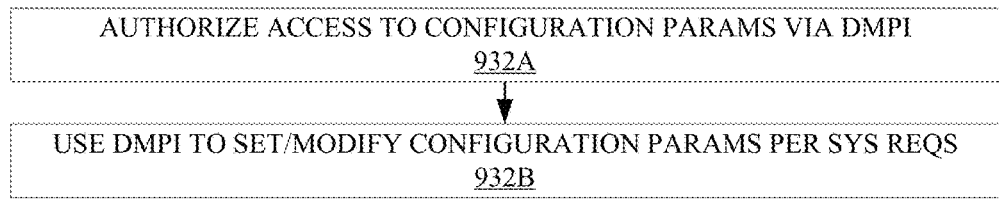
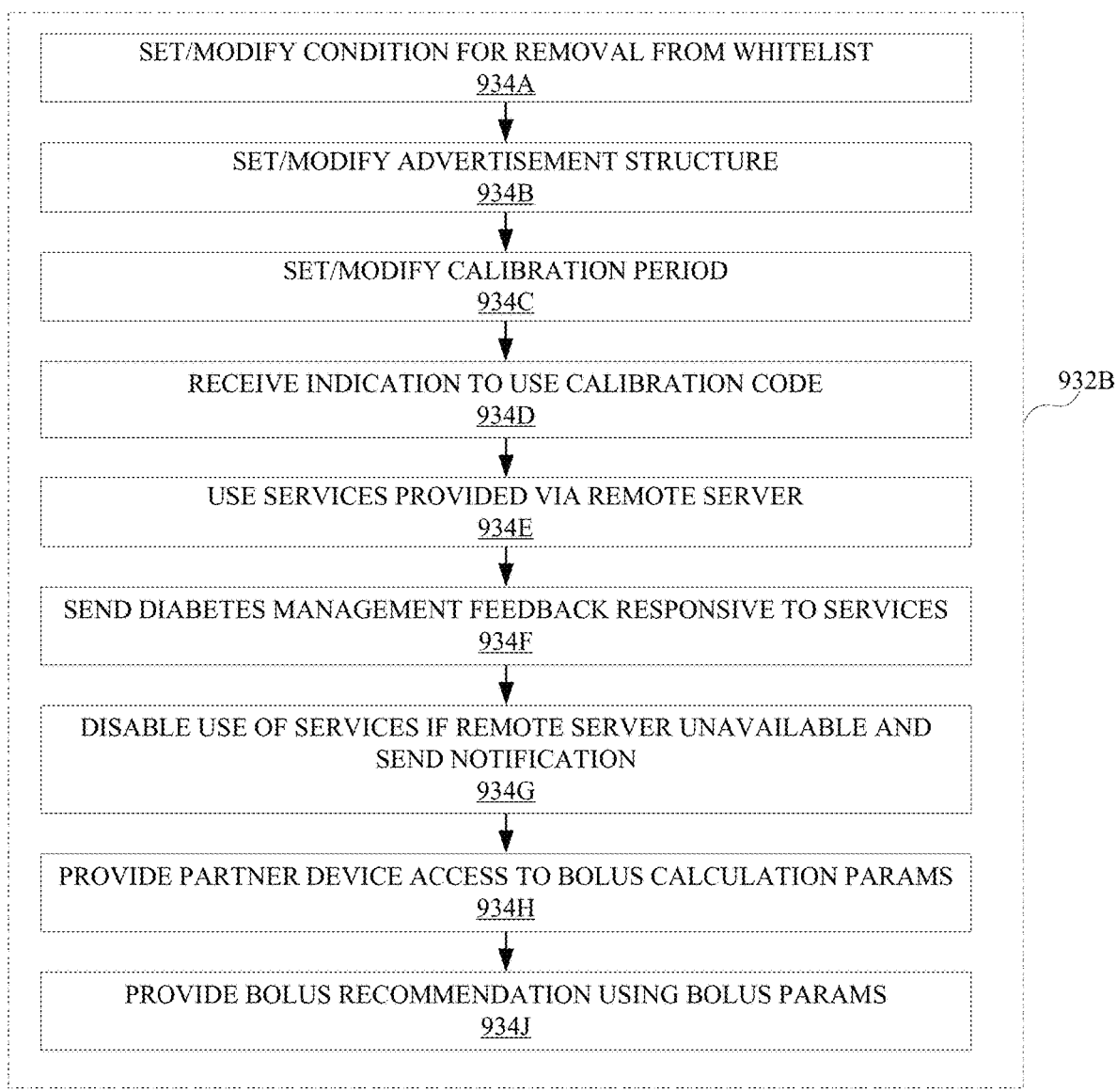

ENABLE 1ST PATH WITH 1ST DEGREE OF ACCESS/CONTROL
938A

ENABLE 2ND PATH WITH 2ND DEGREE OF ACCESS/CONTROL BY MODIFYING THE 1ST DEGREE OF ACCESS/CONTROL
938B

SET/CHANGE CONFIGURATION PARAMS IN ACCORDANCE WITH SYS REQS OF PARTNER DEVICE
942A

GRANT PERMISSION TO CONFIGURE ACCURACY/CAL PARAMS
946A

REVOKE PERMISSION TO CONFIGURE ACCURACY/CAL PARAMS
946B

SET/MODIFY AMOUNT OF TIME TO REMAIN ON WHITELIST
946C

DIABETES MANAGEMENT PARTNER INTERFACE FOR WIRELESS COMMUNICATION OF ANALYTE DATA

INCORPORATION BY REFERENCE TO RELATED APPLICATIONS

This application is a continuation of U.S. patent application Ser. No. 17/661,739, filed May 2, 2022, which is a continuation of U.S. patent application Ser. No. 16/169,886, filed Oct. 24, 2018, now U.S. Pat. No. 11,363,025, which is a continuation of U.S. patent application Ser. No. 16/169,661, filed Oct. 24, 2018, now U.S. Pat. No. 11,153,317, which claims the benefit of U.S. Provisional Application No. 62/579,061, filed Oct. 30, 2017. Each of the aforementioned applications is incorporated by reference herein in its entirety, and each is hereby expressly made a part of this specification.

TECHNICAL FIELD

The present disclosure relates generally to an interface for the wireless communication of analyte data gathered using an analyte sensor system. More particularly, the present disclosure is directed to systems, methods, apparatuses, and devices, for using a diabetes management partner interface to improve the flexibility an analyte sensor system in wireless communications with a display device, a medical device, and/or other (e.g., electronic) devices.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which may require uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display. The transmission to wireless display devices can be wireless. The remote device can then provide the user with information about the user's blood glucose levels. Because systems using such implantable sensors can provide more up to date information to users, they may reduce the risk of a user failing to regulate the user's blood glucose levels. Nevertheless, such systems typically still rely on the user to take action in order to regulate the user's blood glucose levels, for example by making an injection.

Certain devices have been introduced to automate regulation of users' blood glucose levels. The introduction of such devices can create issues of interoperability issues with other devices that may be employed for blood glucose monitoring (e.g., the remote device described above), particularly for example where the aforementioned devices are deployed by a different manufacturers. For example, the device introduced for automatic blood glucose level regulation may be subject to certain requirements regarding interference, battery life, accuracy and reliability, and so forth. Such requirements may not be known in advance by the manufacturer of the monitoring device, and/or it may be desirable in some cases to change the requirements from time to time, including based on ecosystem configurations such as the available network connections, number of connected devices, etc. In addition, with an increasing number of electronic devices becoming network connectable, more devices can be used to manage health conditions such as diabetes. But maintaining synchronized analyte data communication among multiple devices, while useful, has become increasingly more difficult for users.

Accordingly, conventional systems are not well-suited for the deployment and integration of devices for monitoring blood glucose levels and additional devices for regulating blood glucose levels, particularly where such devices are offered by various manufacturers, where such devices communicate wirelessly over various types of communication networks and/or media, and where a particular level of flexibility and/or adaptability is desirable.

SUMMARY

A first aspect of the present disclosure includes a method of using a diabetes management partner interface to configure an analyte sensor system for wireless communication with a plurality of partner devices. The method includes the analyte sensor system receiving authorization to provide one of the partner devices with access to a set of configuration parameters via the diabetes management partner interface. The set of configuration parameters is stored in a memory of the analyte sensor system. The method also includes, responsive to input received from the one partner device via the diabetes management partner interface, the analyte sensor system setting or causing a modification to the set of configuration parameters, according to a system requirement of the one partner device.

In certain implementations of the first aspect, which may be generally applicable but are also particularly applicable in connection with any other implementation of the first aspect, the one partner device is an automatic insulin delivery device or a manual insulin delivery device.

In certain implementations of the first aspect, which may be generally applicable but are also particularly applicable in connection with any other implementation of the first aspect, the set of configuration parameters includes one or more of a set of wireless connectivity parameters, a set of access control parameters, and a set of analyte data parameters.

In certain implementations of the first aspect, which may be generally applicable but are also particularly applicable in connection with any other implementation of the first aspect, the system requirement is associated with one of: a battery capacity of the one partner device; an accuracy requirement of the one partner device; a communication protocol used by the one partner device; a regulatory requirement applicable to the one partner device; and an expected operational time of the one partner device.

In certain implementations of the first aspect, which may be generally applicable but are also particularly applicable in connection with any other implementation of the first aspect, the set of wireless connectivity parameters includes a condition under which the one partner device is to be removed from a whitelist maintained for the analyte sensor system. In embodiments, the analyte sensor system setting or causing the modification to the set of configuration parameters according to the system requirement of the one partner device includes the analyte sensor system setting the condition such that the one partner device is to be removed from the whitelist when a battery level of the one partner delivery device meets a threshold.

In certain implementations of the first aspect, which may be generally applicable but are also particularly applicable in connection with any other implementation of the first aspect, the set of wireless connectivity parameters includes an advertisement structure. In embodiments, the analyte sensor system setting or causing the modification to the set of configuration parameters according to the system requirement of the one partner device includes the analyte sensor system using the diabetes management partner interface to set or modify the advertisement structure.

In certain implementations of the first aspect, which may be generally applicable but are also particularly applicable in connection with any other implementation of the first aspect, the set of access control parameters includes one or more of: a number of display devices that the analyte sensor system may connect to; and a level of access or control the analyte sensor system may give to one or more of the display devices.

In certain implementations of the first aspect, which may be generally applicable but are also particularly applicable in connection with any other implementation of the first aspect, the set of analyte data parameters includes a calibration period for the analyte sensor system. In embodiments, the analyte sensor system setting or causing the modification to the set of configuration parameters according to the system requirement of the one partner device includes the analyte sensor system using the diabetes management partner interface to set or modify the calibration period.

In certain implementations of the first aspect, which may be generally applicable but are also particularly applicable in connection with any other implementation of the first aspect, the set of analyte data parameters includes a factory calibration code. In embodiments, the analyte sensor system uses the diabetes management partner interface to receive from the one partner device an indication to use the factory calibration code, according to the system requirement of the one partner device. The analyte sensor system setting or causing the modification to the set of configuration parameters according to the system requirement of the one partner device may include the analyte sensor system using the diabetes management partner interface to set or modify the calibration period to zero or none.

In certain implementations of the first aspect, which may be generally applicable but are also particularly applicable in connection with any other implementation of the first aspect, the set of wireless connectivity parameters includes settings in a remote server. The analyte sensor system setting or causing the modification to the set of configuration parameters according to the system requirement of the one partner device may include using the diabetes management partner interface to configure the analyte sensor to perform a number of operations. Such operations may include the use of services provided via the remote server. Such operations may include, responsive to services provided via the remote server, transmitting diabetes management feedback to one or more display devices connected to the analyte sensor system. Such operations may include, if the services provided via the remote server become unavailable, disabling the use of the services and send a related notification to display devices connected to the analyte sensor system.

In certain implementations of the first aspect, which may be generally applicable but are also particularly applicable in connection with any other implementation of the first aspect, the set of analyte date parameters includes bolus calculation parameters. In embodiments, the analyte sensor system setting or causing the modification to the set of configuration parameters according to the system requirement of the one partner device includes the analyte sensor system using the diabetes management partner interface to provide the one partner device with access to the bolus calculation parameters. In embodiments, the method also includes the analyte sensor system providing a bolus recommendation based on a calculation performed using the bolus calculation parameters.

A second aspect of the present disclosure includes an analyte sensor system for wireless communication with a plurality of partner devices. The analyte sensor system is configurable by use of a diabetes management partner interface. The analyte sensor system includes an analyte senor used to generate analyte information. The analyte sensor system includes a transceiver adapted to transmit and receive wireless signals. Further, the analyte sensor system includes a memory to store a set of configuration parameters used by the transceiver to transmit and receive the wireless signals. The analyte sensor system also includes circuitry operatively coupled to the transceiver and the memory and adapted to cause the analyte sensor system to perform a number of operations. Such operations include, receiving authorization to provide one of the partner devices with access to a set of configuration parameters via the diabetes management partner interface. Such operations include, responsive to input received from the one partner device via the diabetes management partner interface, setting or causing a modification to the set of configuration parameters, according to a system requirement of the partner device.

In certain implementations of the second aspect, which may be generally applicable but are also particularly applicable in connection with any other implementation of the second aspect, the one partner device is an automatic insulin delivery device or a manual insulin delivery device.

In certain implementations of the second aspect, which may be generally applicable but are also particularly applicable in connection with any other implementation of the second aspect, the set of configuration parameters comprises one or more of a set of wireless connectivity parameters, a set of access control parameters, and a set of analyte data parameters.

In certain implementations of the second aspect, which may be generally applicable but are also particularly applicable in connection with any other implementation of the second aspect, the system requirement is associated with one of: a battery capacity of the one partner device; an accuracy requirement of the one partner device; a communication protocol used by the one partner device; a regulatory requirement applicable to the one partner device; and an expected operational time of the one partner device.

In certain implementations of the second aspect, which may be generally applicable but are also particularly applicable in connection with any other implementation of the second aspect, the set of wireless connectivity parameters includes a condition under which the one partner device is to be removed from a whitelist maintained for the analyte sensor system. In embodiments, the circuitry is further adapted to cause the analyte sensor system to set the condition such that the one partner device is to be removed from the whitelist when a battery level of the one partner delivery device meets a threshold, according to the system requirement of the one partner device.

In certain implementations of the second aspect, which may be generally applicable but are also particularly applicable in connection with any other implementation of the second aspect, the set of wireless connectivity parameters includes an advertisement structure. In embodiments, the circuitry is further adapted to cause the analyte sensor system to use the diabetes management partner interface to set or modify the advertisement structure.

In certain implementations of the second aspect, which may be generally applicable but are also particularly applicable in connection with any other implementation of the second aspect, the set of access control parameters comprises one or more of: a number of display devices that the analyte sensor system may connect to; and a level of access or control the analyte sensor system may give to one or more of the display devices.

In certain implementations of the second aspect, which may be generally applicable but are also particularly applicable in connection with any other implementation of the second aspect, the set of analyte data parameters comprises a calibration period for the analyte sensor system. In embodiments, the circuitry is further adapted to cause the analyte sensor system to use the diabetes management partner interface to set or modify the calibration period.

In certain implementations of the second aspect, which may be generally applicable but are also particularly applicable in connection with any other implementation of the second aspect, the set of analyte data parameters comprises a factory calibration code. In embodiments, the circuitry is further adapted to cause the analyte sensor system to use the diabetes management partner interface to receive from the one partner device an indication to use the factory calibration code, according to the system requirement of the one partner device. In embodiments, the circuitry is further adapted to cause the analyte sensor system to use the diabetes management partner interface to set or modify the calibration period to zero or none.

In certain implementations of the second aspect, which may be generally applicable but are also particularly applicable in connection with any other implementation of the second aspect, the set of wireless connectivity parameters includes settings in a remote server. In embodiments, the circuitry is further adapted to cause the analyte sensor system to use the diabetes management partner interface to configure the analyte sensor to perform additional operations. One such operation is to use services provided via the remote server. One such operation is to, responsive to services provided via the remote server, transmit diabetes management feedback to one or more display devices connected to the analyte sensor system. One such operation is to, if the services provided via the remote server become unavailable, disable the use of the services and send a related notification to display devices connected to the analyte sensor system.

In certain implementations of the second aspect, which may be generally applicable but are also particularly applicable in connection with any other implementation of the second aspect, the set of analyte date parameters includes bolus calculation parameters. In embodiments, the circuitry is further adapted to cause the analyte sensor system to use the diabetes management partner interface to configure the analyte sensor system to provide the one partner device with access to the bolus calculation parameters, according to the system requirement of the partner device. In embodiments, the circuitry is further adapted to cause the analyte sensor to provide a bolus recommendation based on a calculation performed using the bolus calculation parameters.

A third aspect of the present disclosure includes a system. The system includes one or more partner devices adapted to deliver insulin to a user. The system includes an analyte sensor system adapted to generate analyte information. The analyte sensor system includes a set of configuration parameters used to transmit and receive wireless signals. The configuration parameters are configurable by use of a diabetes management partner interface. The system also includes a display device connectable to the analyte sensor system and adapted to display analyte information and to provide authorization for the analyte sensor system to provide one of the partner devices with access to the set of configuration parameters via the diabetes management partner interface. The one partner devices is adapted to use the diabetes management partner interface to set or cause a modification to the set of configuration parameters, according to a system requirement of the partner device.

In certain implementations of the third aspect, which may be generally applicable but are also particularly applicable in connection with any other implementation of the third aspect, the one partner device is an automatic insulin delivery device or a manual insulin delivery device.

In certain implementations of the third aspect, which may be generally applicable but are also particularly applicable in connection with any other implementation of the third aspect, the set of configuration parameters includes one or more of a set of wireless connectivity parameters, a set of access control parameters, and a set of analyte data parameters.

In certain implementations of the third aspect, which may be generally applicable but are also particularly applicable in connection with any other implementation of the third aspect, the system requirement is associated with one of: a battery capacity of the one partner device; an accuracy requirement of the one partner device; a communication protocol used by the one partner device; a regulatory requirement applicable to the one partner device; and an expected operational time of the one partner device.

In certain implementations of the third aspect, which may be generally applicable but are also particularly applicable in connection with any other implementation of the third aspect, the set of wireless connectivity parameters includes a condition under which the one partner device is to be removed from a whitelist maintained for the analyte sensor system. In embodiments, the one partner device is further adapted use the diabetes management partner interface to set or modify the condition such that the one partner device is to be removed from the whitelist when a battery level of the one partner delivery device meets a threshold, according to the system requirement of the one partner device.

In certain implementations of the third aspect, which may be generally applicable but are also particularly applicable in connection with any other implementation of the third aspect, the set of wireless connectivity parameters includes an advertisement structure. In embodiments, the one partner device is further adapted to use the diabetes management partner interface to set or modify the advertisement structure.

In certain implementations of the third aspect, which may be generally applicable but are also particularly applicable in connection with any other implementation of the third aspect, the set of access control parameters includes one or more of: a number of display devices that the analyte sensor system may connect to; and a level of access or control the analyte sensor system may give to one or more of the display devices.

In certain implementations of the third aspect, which may be generally applicable but are also particularly applicable in connection with any other implementation of the third aspect, the set of analyte data parameters includes a calibration period for the analyte sensor system. In embodiments, the one partner device is further adapted to use the diabetes management partner interface to set or modify the calibration period.

In certain implementations of the third aspect, which may be generally applicable but are also particularly applicable in connection with any other implementation of the third aspect, the set of analyte data parameters includes a factory calibration code. In embodiments, the one partner device is further adapted to use the diabetes management partner interface to: provide the analyte sensor system with an indication to use the factory calibration code, according to the system requirement of the one partner device; and to set or modify the calibration period to zero or none.

In certain implementations of the third aspect, which may be generally applicable but are also particularly applicable in connection with any other implementation of the third aspect, the set of wireless connectivity parameters includes settings in a remote server. In embodiments, the one partner device is further adapted to use the diabetes management partner interface to configure the analyte sensor to perform a number of operations. The one partner device is further adapted to use services provided via the remote server. The one partner device is further adapted to, responsive to services provided via the remote server, transmit diabetes management feedback to display device connectable to the analyte sensor system. The one partner device is further adapted to, if the services provided via the remote server become unavailable, disable the use of the services and send a related notification to the display device connectable to the analyte sensor system.

In certain implementations of the third aspect, which may be generally applicable but are also particularly applicable in connection with any other implementation of the third aspect, the set of analyte date parameters includes bolus calculation parameters. In embodiments, the one partner device is further adapted to use the diabetes management partner interface to configure the analyte sensor system to provide the one partner device with access to the bolus calculation parameters, according to the system requirement of the partner device. In embodiments, the one partner device is further adapted to use the diabetes management partner interface receive from the analyte sensor system a bolus recommendation based on a calculation performed using the bolus calculation parameters.

A fourth aspect of the present disclosure includes a method of using a diabetes management partner interface to configure wireless communications among an analyte sensor system and one or more of a display device and a partner device. The method includes an analyte sensor system enabling a first wireless signal communication path. The first wireless communication signal path is between the analyte sensor system and the display device. For the first wireless communication path, the analyte sensor system provides the display device with a first degree of access or control over the analyte sensor system. The method also includes the analyte sensor system enabling a second wireless signal communication path. The second wireless signal communication path is between the analyte sensor system and the partner device. The analyte sensor system enabling the second wireless signal communication path includes causing a modification to the first degree of access or control in order to implement a second degree of access or control according to a system requirement of the partner device. The modification is caused in response to input received from the partner device via the diabetes management partner interface.

In certain implementations of the fourth aspect, which may be generally applicable but are also particularly applicable in connection with any other implementation of the fourth aspect, causing the modification to the first degree of access or control includes using the diabetes management partner interface to set or change a set of configuration parameters implemented by the analyte sensor system, in accordance with the system requirement of the partner device.

In certain implementations of the fourth aspect, which may be generally applicable but are also particularly applicable in connection with any other implementation of the fourth aspect, the set of configuration parameters includes one or more of access control parameters for the display device or the partner device, accuracy or calibration parameters for the analyte sensor system, and wireless communication parameters for communications to be exchanged among the analyte sensor system and one or more of the display device and the partner device.

In certain implementations of the fourth aspect, which may be generally applicable but are also particularly applicable in connection with any other implementation of the fourth aspect, using the diabetes management partner interface to set or change the set of configuration parameters includes granting to the partner device permission to configure the accuracy or calibration parameters for the analyte sensor system via the diabetes management partner interface.

In certain implementations of the fourth aspect, which may be generally applicable but are also particularly applicable in connection with any other implementation of the fourth aspect, using the diabetes management partner interface to set or change the set of configuration parameters includes revoking from the display device permission to configure the accuracy or calibration parameters for the analyte sensor.

In certain implementations of the fourth aspect, which may be generally applicable but are also particularly applicable in connection with any other implementation of the fourth aspect, the access control parameters include a whitelist for devices connectable to the analyte sensor system. The method may also include using the diabetes management partner interface to set or change the set of configuration parameters comprises setting or modifying an amount of time the partner device is to remain on the whitelist before being removed from the whitelist.

A fifth aspect of the present disclosure includes an analyte sensor system for wireless communication with one or more of a display device and a partner device. The analyte sensor system is configurable by use of a diabetes management partner interface. The analyte sensor system includes a memory to store a set of configuration parameters used by a transceiver to transmit and receive the wireless signals. The analyte sensor system also includes circuitry operatively coupled to the transceiver and the memory and adapted to cause the analyte sensor system to perform a number of operations. One such operation is to enable a first wireless signal communication path. The first wireless communication signal path is between the analyte sensor system and the display device. For the first wireless communication path, the analyte sensor system provides the display device with a first degree of access or control over the analyte sensor system. Another such operation is to enable a second wireless signal communication path. The second wireless signal communication path is between the analyte sensor system and the partner device. The second wireless signal communication path is enabled by a modification made by the analyte sensor system to the first degree of access or control. The modification to the first degree of access or control is made in response to input received from the partner device via the diabetes management partner interface. The modification to the first degree of access or control is made in order to implement a second degree of access or control according to a system requirement of the partner device.

In certain implementations of the fifth aspect, which may be generally applicable but are also particularly applicable in connection with any other implementation of the fifth aspect, in order to make the modification to the first degree of access or control, the circuitry is further adapted to cause the analyte sensor system to use the diabetes management partner interface to set or change a set of configuration parameters implemented by the analyte sensor system, in accordance with the system requirement of the partner device.

In certain implementations of the fifth aspect, which may be generally applicable but are also particularly applicable in connection with any other implementation of the fifth aspect, the set of configuration parameters includes one or more of access control parameters for the display device or the partner device, accuracy or calibration parameters for the analyte sensor system, and wireless communication parameters for communications to be exchanged among the analyte sensor system and one or more of the display device and the partner device.

In certain implementations of the fifth aspect, which may be generally applicable but are also particularly applicable in connection with any other implementation of the fifth aspect, the circuitry is further adapted to cause the analyte sensor system to grant to the partner device permission to configure the accuracy or calibration parameters for the analyte sensor system via the diabetes management partner interface.

In certain implementations of the fifth aspect, which may be generally applicable but are also particularly applicable in connection with any other implementation of the fifth aspect, the circuitry is further adapted to cause the analyte sensor system to revoke from the display device permission to configure the accuracy or calibration parameters for the analyte sensor.

In certain implementations of the fifth aspect, which may be generally applicable but are also particularly applicable in connection with any other implementation of the fifth aspect, the access control parameters include a whitelist for devices connectable to the analyte sensor system. In embodiments, the circuitry is further adapted to set or modify an amount of time the partner device is to remain on the whitelist before being removed from the whitelist.

A sixth aspect of the present disclosure includes a method of using a diabetes management partner interface for an analyte sensor system to control wireless communications among the analyte sensor system and one or more remote devices connectable to the analyte sensor system. The one or more remote devices include a display device and a partner device. The method includes the analyte sensor system determining whether a connection request received from one of the remote devices originated from a partner class within the one or more remote devices. The remote devices in the partner class are adapted to provide medicaments. The partner class includes the partner device. The method includes, if the connection request originated from the partner class, the diabetes management partner interface enabling selection of an operating mode corresponding to the partner class. In order to support a system requirement of the partner device, the operating mode uses a set of configuration parameters for the partner class.

In certain implementations of the sixth aspect, which may be generally applicable but are also particularly applicable in connection with any other implementation of the sixth aspect, the method includes exchanging the wireless communications with at least one of the remote devices using the operating mode corresponding to the partner class.

In certain implementations of the sixth aspect, which may be generally applicable but are also particularly applicable in connection with any other implementation of the sixth aspect, exchanging the wireless communications using the operating mode corresponding to the partner class includes transmitting a mode indicator usable by the at least one of the remote devices to determine the operating mode being used.

In certain implementations of the sixth aspect, which may be generally applicable but are also particularly applicable in connection with any other implementation of the sixth aspect, the set of configuration parameters used to support the system requirement of the partner device includes one or more of access control parameters for the display device or the partner device, accuracy or calibration parameters for the analyte sensor system, and wireless communication parameters for communications to be exchanged among the analyte sensor system and one or more of the remote devices.

In certain implementations of the sixth aspect, which may be generally applicable but are also particularly applicable in connection with any other implementation of the sixth aspect, the mode indicator is operable by the analyte sensor system to use the diabetes management partner interface to deactivate access by a set of the remote devices that are not in the partner class to one or more of the access control parameters, the accuracy or calibration parameters, and the wireless communication parameters. In embodiments, access to the one or more of the access control parameters, the accuracy or calibration parameters, and the wireless communication parameters by the set of remote devices is activated when the analyte sensor system uses an operating mode corresponding to the set of remote devices.

In certain implementations of the sixth aspect, which may be generally applicable but are also particularly applicable in connection with any other implementation of the sixth aspect, the method also includes determining that the analyte sensor system has not received a wireless communication from the partner device for at least a predetermined amount of time. The method also includes, in response to the determining, and further in response to receiving a connection request from one of the remote devices in a set of the remote devices that are not in the partner class, the analyte sensor system selecting an operating mode corresponding to the set of the remote devices that are not in the partner class. The operating mode corresponding to the set of remote devices that are not in the partner class follows a set of configuration parameters specific to the set of remote devices that are not in the partner class. In embodiments, the method also includes removing the partner device from a whitelist.

In certain implementations of the sixth aspect, which may be generally applicable but are also particularly applicable in connection with any other implementation of the sixth aspect, the method includes the analyte sensor system using the diabetes management partner interface to receive from the partner device a value for one of the configuration parameters. The method also includes the analyte sensor system modifying the one configuration parameter using the value received from the partner device.

In certain implementations of the sixth aspect, which may be generally applicable but are also particularly applicable in connection with any other implementation of the sixth aspect, the method includes the analyte sensor system sending the value for the configuration parameter to the display device. The value includes one or more of: a specified time after which the partner device is to be removed from a white list maintained for the analyte sensor system; and a specified time after which the display device is to be removed from the whitelist.

In certain implementations of the sixth aspect, which may be generally applicable but are also particularly applicable in connection with any other implementation of the sixth aspect, exchanging the wireless communications using the operating mode corresponding to the partner device includes one or more of: modifying a white list maintained for the analyte sensor system in order to switch off slots for devices other than the partner device; and transmitting advertisement messages directed to only the partner device.

In certain implementations of the sixth aspect, which may be generally applicable but are also particularly applicable in connection with any other implementation of the sixth aspect, the method includes, if the connection request did not originate from the partner class, the analyte sensor system selecting an operating mode corresponding to a set of the remote devices that are not in the partner class. The operating mode corresponding to the set of remote devices that are not in the partner class uses a set of configuration parameters specific to the set of the remote devices that are not in the partner class.

In certain implementations of the sixth aspect, which may be generally applicable but are also particularly applicable in connection with any other implementation of the sixth aspect, the display device is in the set of remote devices that are not in the partner class. In embodiments, the method further includes using the diabetes management partner interface to provide the display device with access to the set of configuration parameters specific to the set of the remote devices that are not in the partner class. The method may further include the analyte sensor system setting or modifying a value for one of the configuration parameters specific to the set of the remote devices that are not in the partner class, responsive to input received from the display device.

In certain implementations of the sixth aspect, which may be generally applicable but are also particularly applicable in connection with any other implementation of the sixth aspect, exchanging the wireless communications using the operating mode corresponding to the partner class includes modifying advertisement slots to advertise only for a the partner device or a partner device controller.

In certain implementations of the sixth aspect, which may be generally applicable but are also particularly applicable in connection with any other implementation of the sixth aspect, exchanging the wireless communications using the operating mode corresponding to the partner class includes: responsive to a command received via the diabetes management partner interface, the analyte sensor system accepting only connection requests received from the partner device. The command may be received from the partner device.

A seventh aspect of the present disclosure includes an analyte sensor system that uses a diabetes management partner interface to control wireless communications among the analyte sensor system and one or more remote devices connectable to the analyte sensor system. The one or more remote devices includes a display device and a partner device. The analyte sensor system includes circuitry operatively coupled to a memory that stores instructions that, when executed, cause the analyte sensor system to perform a number of operations. One such operation is to determine whether a connection request received from one of the remote devices originated from a partner class within the one or more remote devices. The remote devices in the partner class are adapted to provide medicaments. The partner class includes the partner device. Another such operation is to, if the connection request originated from the partner class, use the diabetes management partner interface to enable selection of an operating mode corresponding to the partner class. In order to support a system requirement of the partner device, the operating mode uses a set of configuration parameters for the partner class.

In certain implementations of the seventh aspect, which may be generally applicable but are also particularly applicable in connection with any other implementation of the seventh aspect, the memory further stores instructions that, when executed, cause the analyte sensor system to exchange the wireless communications with at least one of the remote devices using the operating mode corresponding to the partner class.

In certain implementations of the seventh aspect, which may be generally applicable but are also particularly applicable in connection with any other implementation of the seventh aspect, the wireless communications exchanged using the operating mode corresponding to the partner class include a mode indicator sent by the analyte sensor system to the at least one of the remote devices. The mode indicator is usable by the at least one of the remote devices to determine the operating mode being used.

In certain implementations of the seventh aspect, which may be generally applicable but are also particularly applicable in connection with any other implementation of the seventh aspect, the set of configuration parameters used to support the system requirement of the partner device includes one or more of access control parameters for the display device or the partner device, accuracy or calibration parameters for the analyte sensor system, and wireless communication parameters for communications to be exchanged among the analyte sensor system and one or more of the remote devices.

In certain implementations of the seventh aspect, which may be generally applicable but are also particularly applicable in connection with any other implementation of the seventh aspect, the mode indicator is operable by the analyte sensor system to use the diabetes management partner interface to deactivate access by a set of the remote devices that are not in the partner class to one or more of the access control parameters, the accuracy or calibration parameters, and the wireless communication parameters. In embodiments, the memory further stores instructions that, when executed, cause the analyte sensor system to provide access to the one or more of the access control parameters, the accuracy or calibration parameters, and the wireless communication parameters by the set of remote devices when the analyte sensor system uses an operating mode corresponding to the set of remote devices.

In certain implementations of the seventh aspect, which may be generally applicable but are also particularly applicable in connection with any other implementation of the seventh aspect, the memory further stores instructions that, when executed, cause the analyte sensor system to perform additional operations. One such operation is to make a determination that the analyte sensor system has not received a wireless communication from the partner device for at least a predetermined amount of time. Another such operation is to, in response to the determination, and further in response to a connection request received from one of the remote devices in a set of the remote devices that are not in the partner class, select an operating mode corresponding to the set of the remote devices that are not in the partner class. The operating mode corresponding to the set of remote devices that are not in the partner class follows a set of configuration parameters specific to the set of remote devices that are not in the partner class.

In certain implementations of the seventh aspect, which may be generally applicable but are also particularly applicable in connection with any other implementation of the seventh aspect, the memory further stores instructions that, when executed, cause the analyte sensor system to remove the partner device from a whitelist.

In certain implementations of the seventh aspect, which may be generally applicable but are also particularly applicable in connection with any other implementation of the seventh aspect, the memory further stores instructions that, when executed, cause the analyte sensor system to perform additional operations. One such operation is to use the diabetes management partner interface to receive from the partner device a value for one of the configuration parameters. Another such operation is to modify the one configuration parameter using the value received from the partner device.

In certain implementations of the seventh aspect, which may be generally applicable but are also particularly applicable in connection with any other implementation of the seventh aspect, the memory further stores instructions that, when executed, cause the analyte sensor system to send the value for the configuration parameter to the display device. The value includes one or more of: a specified time after which the partner device is to be removed from a white list maintained for the analyte sensor system; and a specified time after which the display device is to be removed from the whitelist.

In certain implementations of the seventh aspect, which may be generally applicable but are also particularly applicable in connection with any other implementation of the seventh aspect, the memory further stores instructions that, when executed, cause the analyte sensor system to perform additional operations. One such operation is to modify a white list maintained for the analyte sensor system in order to switch off slots for devices other than the partner device. Another such operation is to transmit advertisement messages directed to only the partner device.

In certain implementations of the seventh aspect, which may be generally applicable but are also particularly applicable in connection with any other implementation of the seventh aspect, the memory further stores instructions that, when executed, cause the analyte sensor system to: if the connection request did not originate from the partner class, select an operating mode corresponding to a set of the remote devices that are not in the partner class, wherein the operating mode corresponding to the set of remote devices that are not in the partner class uses a set of configuration parameters specific to the set of the remote devices that are not in the partner class.

In certain implementations of the seventh aspect, which may be generally applicable but are also particularly applicable in connection with any other implementation of the seventh aspect, the display device is in the set of remote devices that are not in the partner class, and wherein the memory further stores instructions that, when executed, cause the analyte sensor system to perform additional operations. One such operation is to use the diabetes management partner interface to provide the display device with access to the set of configuration parameters specific to the set of the remote devices that are not in the partner class. Another such operation is to set or modify a value for one of the configuration parameters specific to the set of the remote devices that are not in the partner class, responsive to input received from the display device.

In certain implementations of the seventh aspect, which may be generally applicable but are also particularly applicable in connection with any other implementation of the seventh aspect, the memory further stores instructions that, when executed, cause the analyte sensor system to modify advertisement slots to advertise only for a the partner device or a partner device controller.

In certain implementations of the seventh aspect, which may be generally applicable but are also particularly applicable in connection with any other implementation of the seventh aspect, the memory further stores instructions that, when executed, cause the analyte sensor system to: responsive to a command received via the diabetes management partner interface, accept only connection requests received from the partner device. The command may be received from the partner device.

A eighth aspect of the present disclosure includes a method of using a diabetes management interface to allow configurability of an analyte sensor system that exchanges wireless communications with one or more of a partner device and a display device. The method includes the analyte sensor system determining that a first connection request was sent from a remote device in a first class of remote devices. The method includes the analyte sensor system determining that a second connection request was sent from a remote device in a second class of remote devices. The remote devices of the second class of remote devices are adapted to deliver medicaments. The remote devices of the first class of remote devices do not belong to the second class of remote devices. The method includes the analyte sensor system using any one of a plurality of operating modes. A first operating mode of the plurality is specific to a first configuration that utilizes a remote device in the second class of remote devices and does not utilize a remote device in the first class of remote devices. A second operating mode of the plurality is specific to a second configuration that does not utilize a device from the second class of remote devices. A third operating mode of the plurality is specific to a third configuration that utilizes a remote device in the first class of remote devices and a remote device from the second class of remote devices.

In certain implementations of the eighth aspect, which may be generally applicable but are also particularly applicable in connection with any other implementation of the eighth aspect, using the first operating mode of the plurality includes providing the remote device in the second class of remote devices authority to use the diabetes management partner interface to modify permissions provided to the remote device in the first class of remote devices.

In certain implementations of the eighth aspect, which may be generally applicable but are also particularly applicable in connection with any other implementation of the eighth aspect, using the first operating mode of the plurality further includes the analyte sensor system receiving from the remote device in the first class of remote devices an authentication for the remote device in the second class of remote devices to communicate with the analyte sensor system.

In certain implementations of the eighth aspect, which may be generally applicable but are also particularly applicable in connection with any other implementation of the eighth aspect, using the first operating mode further includes, responsive to input received via the diabetes management partner device from the remote device in the second class of remote devices, the analyte sensor system preventing a connection with devices other than the remote device in the second class of remote devices.

In certain implementations of the eighth aspect, which may be generally applicable but are also particularly applicable in connection with any other implementation of the eighth aspect, preventing the connection includes using a first advertisement slot to advertise to the remote device in the second class of remote devices. Preventing the connection also includes using a second advertisement slot to advertise to the remote device in the second class of remote devices or a controller for the remote device in the second class of remote devices.

In certain implementations of the eighth aspect, which may be generally applicable but are also particularly applicable in connection with any other implementation of the eighth aspect, preventing the connection includes the analyte sensor system using the diabetes management partner interface to set or cause a modification to an advertisement structure to include a single advertisement duration dedicated to the remote device in the second class of devices.

In certain implementations of the eighth aspect, which may be generally applicable but are also particularly applicable in connection with any other implementation of the eighth aspect, preventing the connection includes the analyte sensor system accepting connection requests from only the remote device in the second class of remote devices.

In certain implementations of the eighth aspect, which may be generally applicable but are also particularly applicable in connection with any other implementation of the eighth aspect, using the first operating mode of the plurality further includes the analyte sensor system using input received from the remote device in the second class of remote devices via the diabetes management interface to modify timeout rules associated with the remote device in the second class of remote devices.

In certain implementations of the eighth aspect, which may be generally applicable but are also particularly applicable in connection with any other implementation of the eighth aspect, using the second operating mode of the plurality includes one or more of the following operations: modifying a whitelist to exclude the remote device in the second class of remote devices; rejecting connection requests received from the remote device in the second class of remote devices; and advertising exclusively for remote devices in the first class of remote devices.

In certain implementations of the eighth aspect, which may be generally applicable but are also particularly applicable in connection with any other implementation of the eighth aspect, using the third operating mode of the plurality includes the analyte sensor system receiving, via the diabetes management interface, an indication from the remote device in the second class of remote devices of a level of access to the analyte sensor system that the remote device in the first class of remote devices is to be given.

In certain implementations of the eighth aspect, which may be generally applicable but are also particularly applicable in connection with any other implementation of the eighth aspect, the method includes the analyte sensor system using the diabetes management interface to implement the level of access. The method also includes notifying the remote device in the first class of remote devices of the level of access.

In certain implementations of the eighth aspect, which may be generally applicable but are also particularly applicable in connection with any other implementation of the eighth aspect, according to the level of access, the remote device in the first class of remote devices can receive analyte data from the analyte sensor system but cannot access accuracy or calibration parameters used by the analyte sensor system for the third operating mode.

A ninth aspect of the present disclosure includes an analyte sensor system that exchanges wireless communications with one or more of a partner device and a display device. The analyte sensor system is configurable by way of a diabetes management partner interface. The analyte sensor system includes circuitry operatively coupled to a memory that stores instructions that, when executed, cause the analyte sensor system to perform a number of operations. One such operation is to determine that a first connection request was sent from a remote device in a first class of remote devices. Another such operation is to determine that a second connection request was sent from a remote device in a second class of remote devices. The remote devices of the second class of remote devices are adapted to deliver medicaments. The remote devices of the first class of remote devices do not belong to the second class of remote devices. Another such operation is to use any one of a plurality of operating modes. A first operating mode of the plurality is specific to a first configuration that utilizes a remote device in the second class of remote devices and does not utilize a remote device in the first class of remote devices. A second operating mode of the plurality is specific to a second configuration that does not utilize a device from the second class of remote devices. A third operating mode of the plurality is specific to a third configuration that utilizes a remote device in the first class of remote devices and a remote device from the second class of remote devices.

In certain implementations of the ninth aspect, which may be generally applicable but are also particularly applicable in connection with any other implementation of the ninth aspect, the memory further stores instructions that, when executed, cause the analyte sensor system to, in the first operating mode of the plurality, provide the remote device in the second class of remote devices authority to use the diabetes management partner interface to modify permissions provided to the remote device in the first class of remote devices.

In certain implementations of the ninth aspect, which may be generally applicable but are also particularly applicable in connection with any other implementation of the ninth aspect, the memory further stores instructions that, when executed, cause the analyte sensor system to, in the first operating mode of the plurality, receive from the remote device in the first class of remote devices an authentication for the remote device in the second class of remote devices to communicate with the analyte sensor system.

In certain implementations of the ninth aspect, which may be generally applicable but are also particularly applicable in connection with any other implementation of the ninth aspect, the memory further stores instructions that, when executed, cause the analyte sensor system to, in the first operating mode of the plurality: responsive to input received via the diabetes management partner device from the remote device in the second class of remote devices, prevent a connection with devices other than the remote device in the second class of remote devices.

In certain implementations of the ninth aspect, which may be generally applicable but are also particularly applicable in connection with any other implementation of the ninth aspect, the memory further stores instructions that, when executed, cause the analyte sensor system to use a first advertisement slot to advertise to the remote device in the second class of remote devices; and use a second advertisement slot to advertise to the remote device in the second class of remote devices or a controller for the remote device in the second class of remote devices.

In certain implementations of the ninth aspect, which may be generally applicable but are also particularly applicable in connection with any other implementation of the ninth aspect, the memory further stores instructions that, when executed, cause the analyte sensor system to use the diabetes management partner interface to set or cause a modification to an advertisement structure to include a single advertisement duration dedicated to the remote device in the second class of devices.

In certain implementations of the ninth aspect, which may be generally applicable but are also particularly applicable in connection with any other implementation of the ninth aspect, the memory further stores instructions that, when executed, cause the analyte sensor system to accept connection requests from only the remote device in the second class of remote devices.

In certain implementations of the ninth aspect, which may be generally applicable but are also particularly applicable in connection with any other implementation of the ninth aspect, the memory further stores instructions that, when executed, cause the analyte sensor system to, in the first operating mode of the plurality, use input received from the remote device in the second class of remote devices via the diabetes management interface to modify timeout rules associated with the remote device in the second class of remote devices.

In certain implementations of the ninth aspect, which may be generally applicable but are also particularly applicable in connection with any other implementation of the ninth aspect, the memory further stores instructions that, when executed, cause the analyte sensor system to, in the second operating mode of the plurality, perform additional operations. One such operation is to modify a whitelist to exclude the remote device in the second class of remote devices. Another such operation is to reject connection requests received from the remote device in the second class of remote devices. Another such operation is to advertise exclusively for remote devices in the first class of remote devices.

In certain implementations of the ninth aspect, which may be generally applicable but are also particularly applicable in connection with any other implementation of the ninth aspect, the memory further stores instructions that, when executed, cause the analyte sensor system to, in the third operating mode of the plurality, receive, via the diabetes management interface, an indication from the remote device in the second class of remote devices of a level of access to the analyte sensor system that the remote device in the first class of remote devices is to be given.

In certain implementations of the ninth aspect, which may be generally applicable but are also particularly applicable in connection with any other implementation of the ninth aspect, the memory further stores instructions that, when executed, cause the analyte sensor system to: use the diabetes management interface to implement the level of access; and notify the remote device in the first class of remote devices of the level of access.

In certain implementations of the ninth aspect, which may be generally applicable but are also particularly applicable in connection with any other implementation of the ninth aspect, according to the level of access, the remote device in the first class of remote devices can receive analyte data from the analyte sensor system but cannot access accuracy or calibration parameters used by the analyte sensor system for the third operating mode.

A tenth aspect of the present disclosure includes a method of using a diabetes management interface to facilitate the exchange of wireless communications with an analyte sensor system. The method includes using the diabetes management partner interface to establish a first connection between the analyte sensor system and a first partner device. The method includes the analyte sensor system providing the first partner device with access to a set of configuration parameters via the diabetes management interface. The method further includes setting or causing a first modification to the set of configuration parameters in response to input received from the first partner device via the diabetes management partner interface. Setting or causing the first modification is done according to a system requirement of the first partner device. Additionally, the method includes using the diabetes management partner interface to establish a second connection between the analyte sensor system and a second partner device. The method also includes the analyte sensor system providing the second partner device with access to the set of configuration parameters via the diabetes management interface. The method further includes causing a second modification to the set of configuration parameters in response to input received from the second partner device via the diabetes management partner interface. The second modification is done according to a system requirement of the second partner device.

In certain implementations of the tenth aspect, which may be generally applicable but are also particularly applicable in connection with any other implementation of the tenth aspect, using the diabetes management partner interface to establish the second connection occurs after the first connection has been terminated.

In certain implementations of the tenth aspect, which may be generally applicable but are also particularly applicable in connection with any other implementation of the tenth aspect, the method further includes, responsive the analyte sensor system receiving identification information for a third partner device, using the diabetes management partner interface to attempt to establish a third connection between the analyte sensor system and the third partner device. The method also includes, responsive to establishing the third connection between the analyte sensor system and a third partner device, causing a third modification to the set of configuration parameters in response to input received via the diabetes management partner interface. The third modification is done according to a system requirement of the third partner device.

In certain implementations of the tenth aspect, which may be generally applicable but are also particularly applicable in connection with any other implementation of the tenth aspect, the identification information for the third partner device is stored in a server system. In embodiments, the identification information indicates whether the third partner device is authorized to communicate with the analyte sensor system.

In certain implementations of the tenth aspect, which may be generally applicable but are also particularly applicable in connection with any other implementation of the tenth aspect, the analyte sensor system receiving the identification information for the third partner device includes the analyte sensor system receiving the identification information for the third partner device from a display device that received the identification information for the third partner device from the server system.

In certain implementations of the tenth aspect, which may be generally applicable but are also particularly applicable in connection with any other implementation of the tenth aspect, the method includes additional operations. One such operation involves, responsive the analyte sensor system receiving the identification information for the third partner device, using the identification information for the third partner device to determine whether the third partner device is authorized to communicate with the analyte sensor system. Another such operation involves, responsive to determining that the third partner device is not authorized to communicate with the analyte sensor system, denying the attempt to establish the third connection between the analyte sensor system and the third partner device. Another such operation involves, responsive to determining that the third partner device is authorized to communicate with the analyte sensor system, using the diabetes management partner interface to establish the third connection between the analyte sensor system and the third partner device.

In certain implementations of the tenth aspect, which may be generally applicable but are also particularly applicable in connection with any other implementation of the tenth aspect, determining that the third partner device is not authorized to communicate with the analyte sensor system occurs at a first time. In embodiments, determining that the third partner device is authorized to communicate with the analyte sensor system occurs at a second time. The identification information for the third partner device may be updated at the server system between the first time and the second time.

In certain implementations of the tenth aspect, which may be generally applicable but are also particularly applicable in connection with any other implementation of the tenth aspect, the system requirement for the third partner device is stored in a server system. The method further includes causing a fourth modification to the set of configuration parameters in response to input received via the diabetes management partner interface. The fourth modification is made according to an updated version of the system requirement of the third partner device.

A eleventh aspect of the present disclosure includes an analyte sensor system that uses a diabetes management interface to facilitate the exchange of wireless communications. The analyte sensor system includes circuitry operatively coupled to a memory that stores instructions that, when executed, cause the analyte sensor system to perform a number of operations. One such operation is to use the diabetes management partner interface to establish a first connection between the analyte sensor system and a first partner device. Another such operation is to provide the first partner device with access to a set of configuration parameters via the diabetes management interface. Another such operation is to set or cause a first modification to the set of configuration parameters in response to input received from the first partner device via the diabetes management partner interface. The first modification is made according to a system requirement of the first partner device. Another such operation is to use the diabetes management partner interface to establish a second connection between the analyte sensor system and a second partner device. Another such operation is to provide the second partner device with access to the set of configuration parameters via the diabetes management interface. Yet another such operation is to cause a second modification to the set of configuration parameters in response to input received from the second partner device via the diabetes management partner interface. The second modification is made according to a system requirement of the second partner device.

In certain implementations of the eleventh aspect, which may be generally applicable but are also particularly applicable in connection with any other implementation of the eleventh aspect, the second connection is established after the first connection has been terminated.

In certain implementations of the eleventh aspect, which may be generally applicable but are also particularly applicable in connection with any other implementation of the eleventh aspect, the memory further stores instructions that, when executed, cause the analyte sensor system to perform additional operations. One such operation is to receive identification information for a third partner device. Another such operation is to, responsive to the identification information for the third partner device being received, use the diabetes management partner interface to attempt to establish a third connection between the analyte sensor system and the third partner device. Another such operation is to, responsive to the third connection between the analyte sensor system and a third partner device being established, cause a third modification to the set of configuration parameters in response to input received via the diabetes management partner interface. The third modification is made according to a system requirement of the third partner device.

In certain implementations of the eleventh aspect, which may be generally applicable but are also particularly applicable in connection with any other implementation of the eleventh aspect, the identification information for the third partner device is stored in a server system. The identification information indicates whether the third partner device is authorized to communicate with the analyte sensor system.

In certain implementations of the eleventh aspect, which may be generally applicable but are also particularly applicable in connection with any other implementation of the eleventh aspect, the memory further stores instructions that, when executed, cause the analyte sensor system to receive the identification information for the third partner device from a display device that received the identification information for the third partner device from the server system.

In certain implementations of the eleventh aspect, which may be generally applicable but are also particularly applicable in connection with any other implementation of the eleventh aspect, the memory further stores instructions that, when executed, cause the analyte sensor system to perform additional operations. One such operation is to, responsive the identification information for the third partner device being received, use the identification information for the third partner device to determine whether the third partner device is authorized to communicate with the analyte sensor system. Another such operation is to, responsive to a determination that the third partner device is not authorized to communicate with the analyte sensor system, deny the attempt to establish the third connection between the analyte sensor system and the third partner device. Another such operation is to, responsive to a determination that the third partner device is authorized to communicate with the analyte sensor system, use the diabetes management partner interface to establish the third connection between the analyte sensor system and the third partner device.

In certain implementations of the eleventh aspect, which may be generally applicable but are also particularly applicable in connection with any other implementation of the eleventh aspect, the determination that the third partner device is not authorized to communicate with the analyte sensor system is made at a first time. In embodiments, the determination that the third partner device is authorized to communicate with the analyte sensor system is made at a second time. In embodiments, the identification information for the third partner device is updated at the server system between the first time and the second time.

In certain implementations of the eleventh aspect, which may be generally applicable but are also particularly applicable in connection with any other implementation of the eleventh aspect, the system requirement for the third partner device is stored in a server system. The memory further stores instructions that, when executed, cause the analyte sensor system to cause a fourth modification to the set of configuration parameters in response to input received via the diabetes management partner interface. The fourth modification is made according to an updated version of the system requirement of the third partner device.

A twelfth aspect of the present disclosure includes a method. The method includes an analyte sensor system receiving an indication to enter an operating mode specific to use of a partner device. The method further includes establishing a connection between the analyte sensor system and the partner device. The method also includes the analyte sensor system setting or modifying configuration parameters responsive to input received from the partner device via a diabetes management partner interface. The input received from the partner device indicates corresponding operating parameters to be used by the partner device to communicate with the analyte sensor system using the operating mode. The configuration parameters are configured in accordance with a system requirement of the partner device. The method also includes implementing the operating mode specific to the use of the partner device using the operating parameters of the analyte sensor system, such that the system requirement of the partner device is accommodated.

In certain implementations of the twelfth aspect, which may be generally applicable but are also particularly applicable in connection with any other implementation of the twelfth aspect, the configuration parameters include one or more of: permission parameters for a display devices to issue a command or control signal to start, stop, calibrate, or set the length of a sensor session for the analyte sensor system; battery or power management parameters; connection model parameters; timeout parameters, wherein one or more of the timeout parameters relates to a length of time to keep the partner device on a whitelist, advertising timeout, connection establishment timeout, and authorization timeout; alert parameters; configuration settings governing operating modes for the analyte sensor system; and remote server parameters.

In certain implementations of the twelfth aspect, which may be generally applicable but are also particularly applicable in connection with any other implementation of the twelfth aspect, the method further includes the analyte sensor system receiving an indication to transition from implementing in the operating mode specific to the use of the partner device. Further, the method includes the analyte sensor system restoring the configuration parameters to a previous state that existed before setting or modifying the configuration parameters responsive to the input received from the partner device. Restoring the set of configuration parameters to the previous state may include removing the partner device from a whitelist.

A thirteenth aspect of the present disclosure includes a method. The method includes an analyte sensor system determining whether a wireless communication system includes one or more of a display device and a partner device. The method also includes, if the wireless communication system includes the display device, the analyte sensor system determining whether to connect to the display device using one of an intermittent connection model and a continuous connection model. The method further includes, if the system includes the partner device, the analyte sensor system determining whether to connect to the partner device using one of the intermittent connection model the continuous connection model. The analyte sensor system determining which of the intermittent or continuous connection models will be used for connecting to one or more of the display device and the partner device includes using configuration parameters that have been set or modified using input receiving from the partner device via a diabetes management partner interface.

In certain implementations of the thirteenth aspect, which may be generally applicable but are also particularly applicable in connection with any other implementation of the thirteenth aspect, the analyte sensor system determining to connect to the partner device according to the intermittent connection model is done using one of the configuration parameters that has been set responsive to a power requirement of the partner device.

In certain implementations of the thirteenth aspect, which may be generally applicable but are also particularly applicable in connection with any other implementation of the thirteenth aspect, the analyte sensor system determining to connect to the partner device according to the continuous connection model is done using the determination that the system includes the display device.

A fourteenth aspect of the present disclosure includes a method. The method includes an analyte sensor application of a display device receiving an interface to a partner device application associated with a partner device. The method includes the analyte sensor application using the interface to collect information gathered by the partner device application. The information includes one or more of pairing data and analyte dosage data. The method also includes the analyte sensor application using the interface to provide analyte sensor system information. The analyte sensor information is used to indicate one or more of the following: that the analyte sensor system is functioning; a connection model employed by the analyte sensor system in regards to the partner device or the display device; and configuration parameters used by the analyte sensor system to communicate with one or more of the partner device and the display device.

In certain implementations of the fourteenth aspect, which may be generally applicable but are also particularly applicable in connection with any other implementation of the fourteenth aspect, the method further includes the analyte sensor application receiving analyte data from the analyte sensor system. The method also includes the analyte sensor application providing a visual display that includes the analyte data and the information gathered by the partner device application.

In certain implementations of the fourteenth aspect, which may be generally applicable but are also particularly applicable in connection with any other implementation of the fourteenth aspect, the method also includes the analyte sensor application receiving information regarding analyte values from the analyte sensor system. The method also includes the analyte sensor application using the interface to communicate the analyte values to the partner device via the partner device application.

In certain implementations of the fourteenth aspect, which may be generally applicable but are also particularly applicable in connection with any other implementation of the fourteenth aspect, the method also includes the analyte sensor application receiving, via the interface, medicament delivery information gathered by the partner device.

In certain implementations of the fourteenth aspect, which may be generally applicable but are also particularly applicable in connection with any other implementation of the fourteenth aspect, the method also includes the analyte sensor application receiving, via the interface, an alert from the partner device. The alert relates to a problem with the functionality of the partner device.

In certain implementations of the fourteenth aspect, which may be generally applicable but are also particularly applicable in connection with any other implementation of the fourteenth aspect, the method also includes the analyte sensor application of the display device causing the alert to be provided via a user interface.

In certain implementations of the fourteenth aspect, which may be generally applicable but are also particularly applicable in connection with any other implementation of the fourteenth aspect, the method also includes the analyte sensor application of the display device causing the alert to be provided via a remote server.

A fifteenth aspect of the present disclosure includes a method. The method includes establishing a connection between an analyte sensor system and a partner device. The method further includes the analyte sensor system using a diabetes management partner interface to receive configuration parameter information from the partner device. The configuration parameter information relates to operation of the analyte sensor system in accordance with a system requirement of the partner device. The configuration parameter information may include a degree of access to be given to a remote device connectable to the analyte sensor system. The configuration parameter information may include one or more values for a set of configurability parameters used for connections established between the analyte sensor system and the partner device. The one or more values for the set of configurability parameters are selected in accordance with the system requirement of the partner device.

In certain implementations of the fifteenth aspect, which may be generally applicable but are also particularly applicable in connection with any other implementation of the fifteenth aspect, the set of configurability parameters includes one or more of the following. The set of configurability parameters may include connection information for the remote device. The set of configurability parameters may include a connection model to be used for a particular device connectable to the analyte sensor system. The set of configurability parameters may include connection command related data to be read by or sent to the remote device. The set of configurability parameters may include information related to non-use of the partner device. The set of configurability parameters may include security or privacy related parameters. The set of configurability parameters may include information related to power control or battery usage. The set of configurability parameters may include a number of devices connectable to the analyte sensor system. The set of configurability parameters may include a device type of each device connectable to the analyte sensor system. The set of configurability parameters may include a type of information related to analyte data that may be read by and sent to remote devices connectable to the analyte sensor system.

In certain implementations of the fifteenth aspect, which may be generally applicable but are also particularly applicable in connection with any other implementation of the fifteenth aspect, the connection command related data indicates one or more of the following. The connection command related data may indicate whether the partner device or the remote device is eligible for inclusion on a whitelist for the analyte sensor system. The connection command related data may indicate whether the partner device or the remote device is adapted to age off the whitelist. If the partner device or the remote device is adapted to age off the whitelist, the connection command related data may indicate an amount of time before the partner device or the remote device is set to age off the whitelist.

In certain implementations of the fifteenth aspect, which may be generally applicable but are also particularly applicable in connection with any other implementation of the fifteenth aspect, the information related to power control includes a suggestion to age off particular devices to extend battery life for the analyte sensor system.

In certain implementations of the fifteenth aspect, which may be generally applicable but are also particularly applicable in connection with any other implementation of the fifteenth aspect, the information related to power control or battery usage is gathered via a control mechanism that balances battery life of the analyte sensor system against connection reliability as between the analyte sensor system and the partner device or the remote device.

In certain implementations of the fifteenth aspect, which may be generally applicable but are also particularly applicable in connection with any other implementation of the fifteenth aspect, the information related to power control triggers a low power mode for the analyte sensor system.

In certain implementations of the fifteenth aspect, which may be generally applicable but are also particularly applicable in connection with any other implementation of the fifteenth aspect, the degree of access is received only after the analyte sensor system has received authorization for the degree of access to be modified using the parameter information received from the partner device.

A sixteenth aspect of the present disclosure includes a method. The method includes establishing a connection between a display device and an analyte sensor system. The method also includes the display device receiving an indication that the analyte sensor system is connecting to a partner device. The method also includes, after receiving authorization to provide the partner device with access to a set of configuration parameters via a diabetes management partner interface, receiving, via the diabetes management partner interface, configuration parameters for alerts originating from the partner device. The method also includes the display device providing a user interface to configure alerts originating from the analyte sensor system and the alerts originating from the partner device. The method further includes using input received via the user interface to cause a modification to the configuration parameters for the alerts originating from the partner device. The modification is made in accordance with a system requirement of the partner device.

In certain implementations of the sixteenth aspect, which may be generally applicable but are also particularly applicable in connection with any other implementation of the sixteenth aspect, the method also includes receiving, via the user interface, a selection of the partner device or a remote device of a plurality of remote devices that includes the display device, to be used as a primary device for providing one or more of the alerts originating from the analyte sensor system and the alerts originating from the partner device.

In certain implementations of the sixteenth aspect, which may be generally applicable but are also particularly applicable in connection with any other implementation of the sixteenth aspect, the method also includes providing the alerts on a device other than the primary device in the event a battery capacity of the primary device falls below a threshold.

In certain implementations of the sixteenth aspect, which may be generally applicable but are also particularly applicable in connection with any other implementation of the sixteenth aspect, the method also includes the display device receiving, via the user interface, a selection of respective alerts types to be provided for the alerts originating from the partner device and for the alerts originating from the analyte sensor system.

In certain implementations of the sixteenth aspect, which may be generally applicable but are also particularly applicable in connection with any other implementation of the sixteenth aspect, the method also includes providing the alerts via a primary notification device. The method also includes, if no acknowledgment is received in response to providing the alerts via the primary notification device, providing the alerts via a secondary notification device. The primary and secondary notification devices are the partner device, the analyte sensor system, and/or at least one of the plurality of remote devices.

A sixteenth aspect of the present disclosure includes a method for monitoring an operability status of a medicament delivery device. The method includes receiving, from the medicament delivery device, medicament delivery device information related to one or more of the following. The medicament delivery device information may be related to reservoir changes. The medicament delivery device information may be related to pump rewind. The medicament delivery device information may be related to pump prime. The medicament delivery device information may be related to cannula fill. The medicament delivery device information may be related to fluid pressure. The medicament delivery device information may be related to determining a combination of the medicament delivery device information with analyte data generated using the analyte sensor system. The medicament delivery device information may be related to the analyte sensor system using the combination to determine the operability status of the medicament delivery device.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

FIG. 9B is an operational flow diagram illustrating various operations that may be performed in accordance with embodiments of the disclosure.

FIG. 9C is an operational flow diagram illustrating various operations that may be performed in accordance with embodiments of the disclosure.

FIG. 9D is an operational flow diagram illustrating various operations that may be performed in accordance with embodiments of the disclosure.

FIG. 9E is an operational flow diagram illustrating various operations that may be performed in accordance with embodiments of the disclosure.

FIG. 9F is an operational flow diagram illustrating various operations that may be performed in accordance with embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Embodiments of the present disclosure are directed to systems, methods, and devices for wireless communication of analyte data, as well as an interface for the wireless communication of analyte data gathered using an analyte sensor system. In various deployments described herein, the analyte data is glucose data generated by an analyte sensor system configured to connect to display devices, partner devices (e.g., medical devices such as an insulin pump), and the like. Implementing aspects of the present disclosure, including more particularly, the systems, methods, apparatuses, and devices described herein that use a diabetes management partner interface, may improve the flexibility of the analyte sensor system in wireless communications with a display device, one or more partner devices, and/or other (e.g., electronic) devices.

Moreover, implementing aspects of the present disclosure may also allow for improving performance with respect to the reliability, speed, and accuracy of wireless communications, including vis-à-vis partner devices and display devices (e.g., where the foregoing devices may be manufactured by various third-parties), as well as the connection protocols and configurations associated therewith. Additionally, in some cases, system requirements such as those related to accuracy, power consumption, or reliability may be less critical, and in such cases, different configurations and modes of connection may be employed to optimize or adapt system performance. In particular, some aspects of the disclosure relate to, for example, setting or modifying connection parameters of an analyte sensor system based on, among other factors, system requirements of a partner device.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

A. System Overview & Example Configurations

Figure 1:
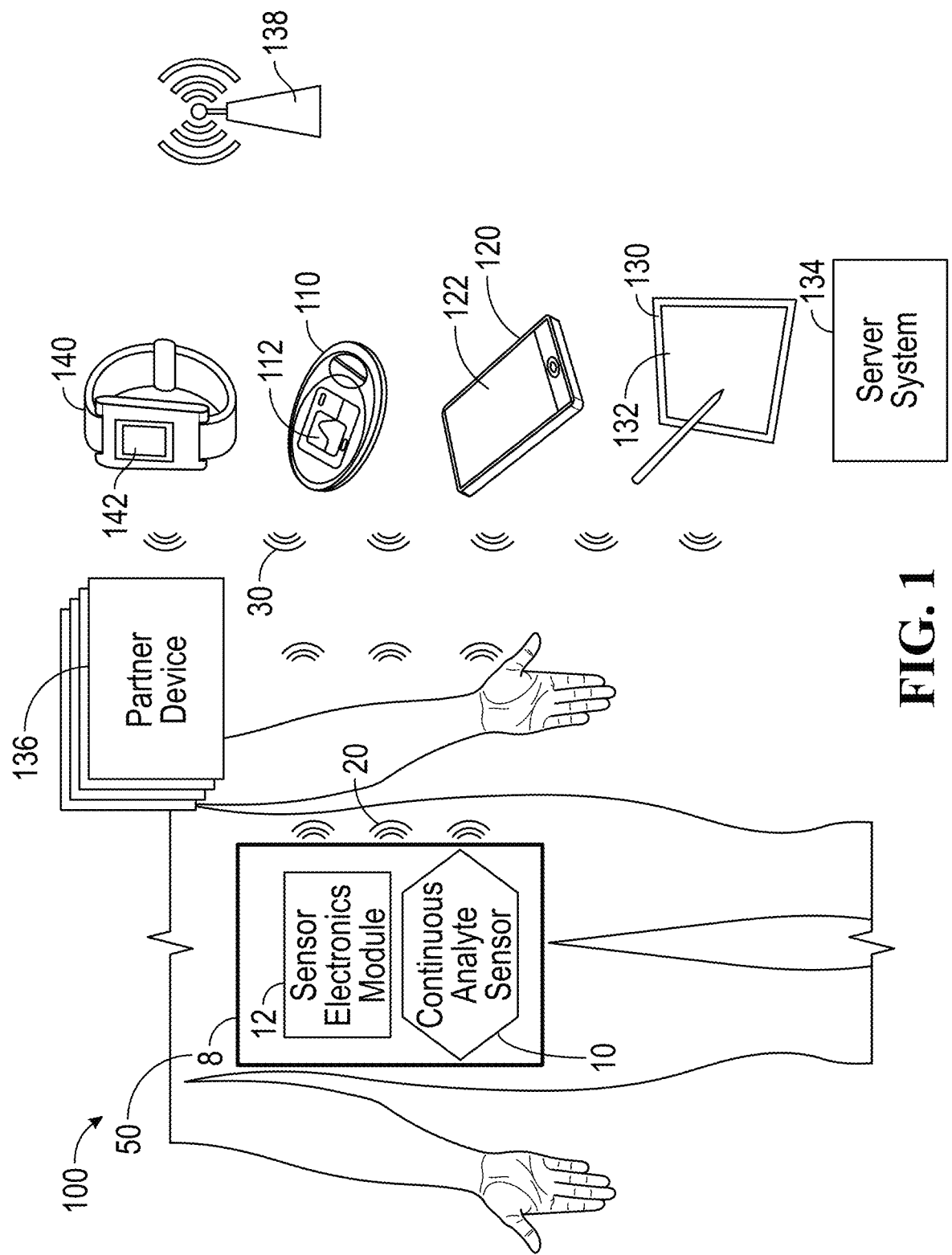
FIG. 1 illustrates aspects of an example system that may be used in connection with implementing embodiments of the disclosure.

FIG. 1 depicts system 100 that may be used in connection with embodiments of the present disclosure that involve gathering, monitoring, and/or providing information regarding analyte values present in a user's body, including for example the user's blood glucose values. System 100 depicts aspects of analyte sensor system 8 that may be communicatively coupled to display devices 110, 120, 130, and 140, partner devices 136, and/or server system 134.

Analyte sensor system 8 in the illustrated embodiment includes sensor electronics module 12 and continuous analyte sensor 10 associated with sensor electronics module 12. Sensor electronics module 12 may be in wireless communication (e.g., directly or indirectly) with one or more of display devices 110, 120, 130, and 140. In addition or alternatively to display devices 110, 120, 130, and 140, sensor electronics module 12 may be in wireless communication (e.g., directly or indirectly) with partner devices 136 and/or server system 134. Likewise, in some examples, display devices 110-140 may additionally or alternatively be in wireless communication (e.g., directly or indirectly) with partner devices 136 and/or server system 134. Various couplings shown in FIG. 1 can be facilitated with wireless access point 138, as also mentioned below.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 may include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

With further reference to FIG. 1, display devices 110, 120, 130, and/or 140 can be configured for displaying (and/or alarming) the displayable sensor information that may be transmitted by sensor electronics module 12 (e.g., in a customized data package that is transmitted to the display devices based on their respective preferences). Each of display devices 110, 120, 130, or 140 can (respectively) include a display such as touchscreen display 112, 122, 132, or 142 for displaying sensor information and/or analyte data to a user and/or receiving inputs from the user. For example, a graphical user interface may be presented to the user for such purposes. In embodiments, the display devices may include other types of user interfaces such as voice user interface instead of or in addition to a touchscreen display for communicating sensor information to the user of the display device and/or receiving user inputs. In embodiments, one, some, or all of display devices 110, 120, 130, 140 may be configured to display or otherwise communicate the sensor information as it is communicated from sensor electronics module 12 (e.g., in a data package that is transmitted to respective display devices), without any additional prospective processing required for calibration and real-time display of the sensor data.

The plurality of display devices 110, 120, 130, 140 depicted in FIG. 1 may include a custom display device, for example, analyte display device 110, specially designed for displaying certain types of displayable sensor information associated with analyte data received from sensor electronics module 12 (e.g., a numerical value and/or an arrow, in embodiments). In embodiments, one of the plurality of display devices 110, 120, 130, 140 includes a smartphone, such as mobile phone 120, based on an Android, iOS, or other operating system, and configured to display a graphical representation of the continuous sensor data (e.g., including current and/or historic data). Other display devices 110, 120, 130, 140 can include other hand-held devices, such as tablet 130, smart watch 140, partner devices 136 (e.g., an insulin delivery device, whether automatic or manual, or a blood glucose meter), a smart fridge, a vehicle, a smart mirror, a smart clock, a smart drink, an implantable insulin delivery device, and/or a desktop or laptop computer.

Because different display devices 110, 120, 130, 140 etc. and partner device(s) 136 can provide different user interfaces, content of the data packages (e.g., amount, format, and/or type of data to be displayed, alarms, and the like) can be customized (e.g., programmed differently by the manufacture and/or by an end user) for each particular display device 110, 120, 130, 140 etc. and/or partner device(s) 136. Accordingly, in embodiments, a plurality of different display devices 110, 120, 130, 140 can be in direct wireless communication with sensor electronics module 12 (e.g., such as an on-skin sensor electronics module that is physically connected to continuous analyte sensor 10) during a sensor session to enable a plurality of different types and/or levels of display and/or functionality associated with the displayable sensor information, which is described in more detail elsewhere herein.

As further illustrated in FIG. 1 and mentioned above, system 100 may also include wireless access point (WAP) 138 that may be used to couple one or more of analyte sensor system 8, the plurality display devices 110, 120, 130, 140 etc., server system 134, and medical device 136 to one another. For example, WAP 138 may provide WiFi and/or cellular or other wireless connectivity within system 100. Near Field Communication (NFC) may also be used among devices of system 100. Server system 134 may be used to collect analyte data from analyte sensor system 8 and/or the plurality of display devices, for example, to perform analytics thereon, generate universal or individualized models for glucose levels and profiles, provide services or feedback, including from individuals or systems remotely monitoring the analyte data, and so on.

Figure 2A:
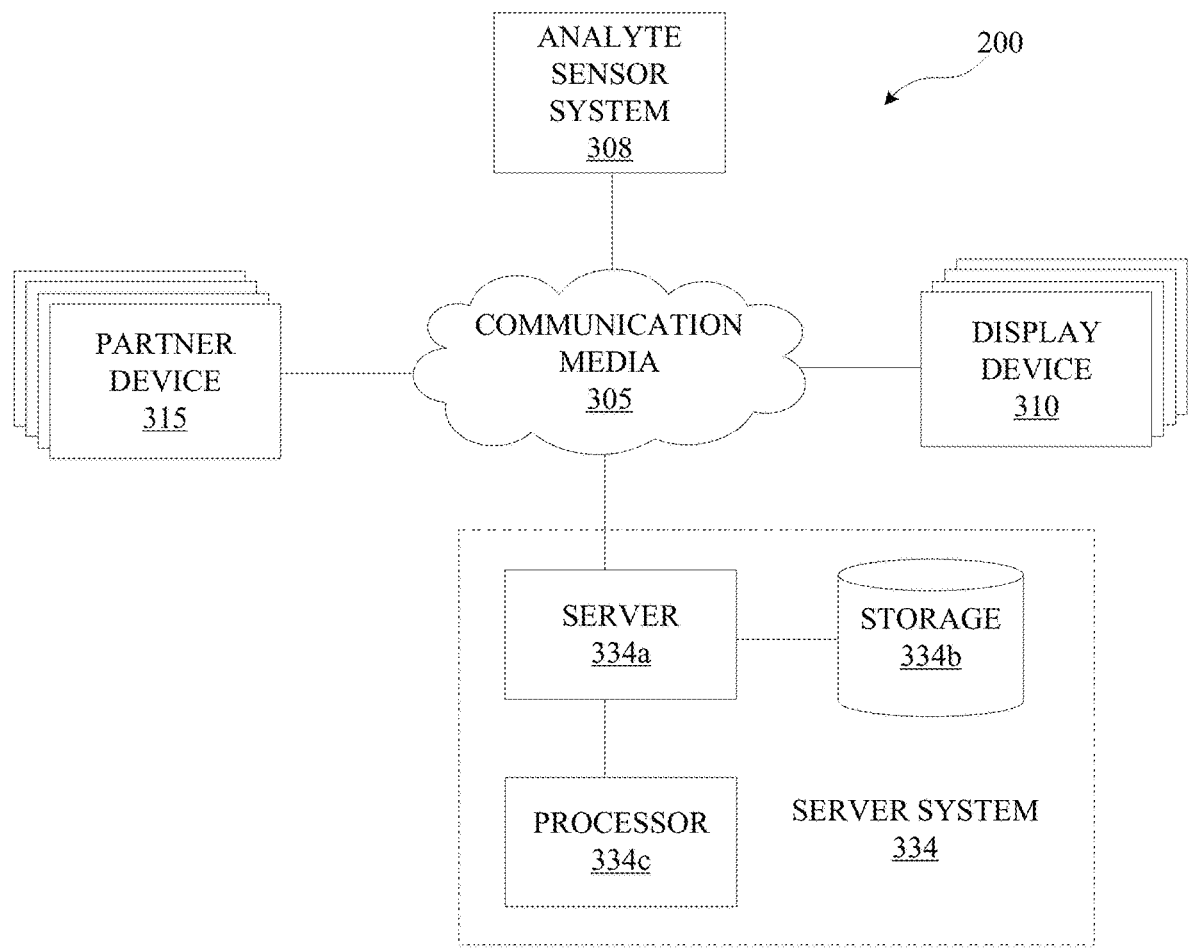
FIG. 2A illustrates aspects of an example system that may be used in connection with implementing embodiments of the disclosure.

Referring now to FIG. 2A, system 200 is depicted. System 200 may be used in connection with implementing embodiments of the disclosed systems, methods, apparatuses, and/or devices, including for example aspects described above in connection with FIG. 1. By way of example, various below-described components of FIG. 2A may be used to provide wireless communication of analyte (e.g., glucose) data, for example among/between analyte sensor system 308, display devices 310, partner devices 315, and/or one or more server systems 334, and so on.

As shown in FIG. 2A, system 200 may include analyte sensor system 308, one or more display devices 310, and/or one or more partner devices 315. Additionally, in the illustrated embodiment, system 200 includes server system 334, which in turn includes server 334a coupled to processor 334c and storage 334b. Analyte sensor system 308 may be coupled to display devices 310, partner devices 315, and/or server system 334 via communication media 305. Many details of the processing, gathering, and exchanging of data, and/or executing actions (e.g., providing medicaments or related instructions) by analyte sensor system 308, partner devices 315, and/or display device 310, etc., are provided below.

As will be described in detail herein, analyte sensor system 308, display devices 310, and/or partner devices 315 may exchange messaging (e.g., control signaling) via communication media 305, and communication media 305 may also be used to deliver analyte data to display devices 310, partner devices 315, and/or server system 334. As alluded to above, display devices 310 may include a variety of electronic computing devices, such as, for example, a smartphone, tablet, laptop, wearable device, etc. Display devices 310 may also include analyte display device 110 customized for the display and conveyance of analyte data and related notifications etc. Partner devices 315 may include medical devices, such as an insulin pump or pen, connectable devices, such as a smart fridge or mirror, key fob, and other devices.

In embodiments, communication media 305 may be based on one or more wireless communication protocols, such as for example Bluetooth, Bluetooth Low Energy (BLE), Zig-Bee, WiFi, IEEE 802.11 protocols, Infrared (IR), Radio Frequency (RF), 2G, 3G, 4G, 5G, etc., and/or wired protocols and media. It will also be appreciated upon studying the present disclosure that communication media can be implemented as one or more communication links, including in some cases, separate links, between the components of system 200, whether or not such links are explicitly shown in FIG. 2A or referred to in connection therewith. By way of illustration, analyte sensor system 308 may be coupled to display device 310 via a first link of communication media 305 using BLE, while display device 310 may be coupled to server system 334 by a second link of communication media 305 using a cellular communication protocol (e.g., 4G LTE).

In embodiments, the elements of system 200 may be used to perform operations of various processes described herein and/or may be used to execute various operations and/or features described herein with regard to one or more disclosed systems and/or methods. Upon studying the present disclosure, one of skill in the art will appreciate that system 200 may include single or multiple analyte sensor systems 308, communication media 305, and/or server systems 334.

As mentioned, communication media 305 may be used to connect or communicatively couple analyte sensor system 308, display devices 310, partner devices 315, and/or server system 334 to one another or to a network. Communication media 305 may be implemented in a variety of forms. For example, communication media 305 may include one or more of an Internet connection, such as a local area network (LAN), a person area network (PAN), a wide area network (WAN), a fiber optic network, internet over power lines, a hard-wired connection (e.g., a bus), DSL, and the like, or any other kind of network connection or communicative coupling. Communication media 305 may be implemented using any combination of routers, cables, modems, switches, fiber optics, wires, radio (e.g., microwave/RF, AM, FM links etc.), and the like. Further, communication media 305 may be implemented using various wireless standards, such as Bluetooth®, BLE, Wi-Fi, IEEE 802.11, 3GPP standards (e.g., 2G GSM/GPRS/EDGE, 3G UMTS/CDMA2000, or 4G LTE/LTE-A/LTE-U, 5G, or subsequent generation), etc. Upon reading the present disclosure, one of skill in the art will recognize other ways to implement communication media 305 for communications purposes, and will also recognize that communication media 305 may be used to implement features of the present disclosure using as of yet undeveloped communications protocols that may be deployed in the future.

Figure 4:
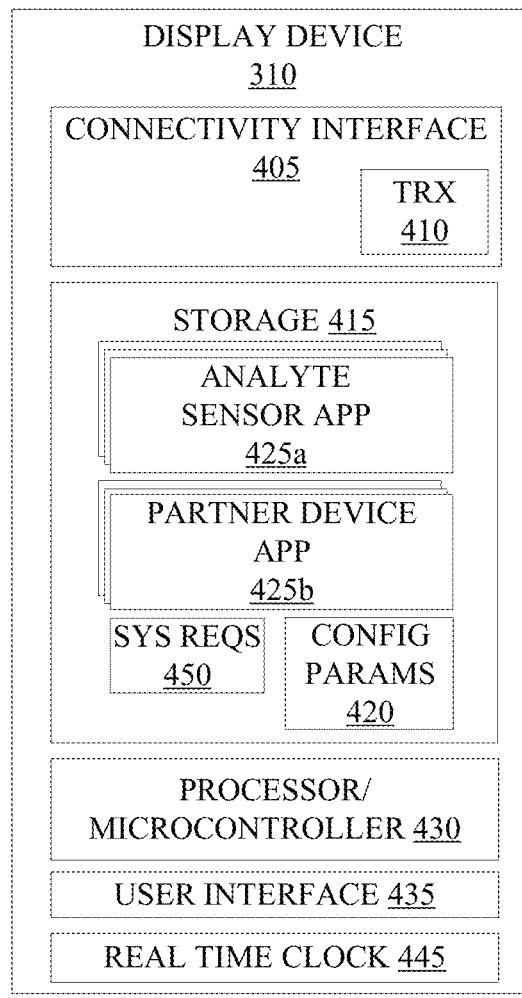
FIG. 4 illustrates aspects of an example display device according to embodiments of the disclosure.
Figure 5A:
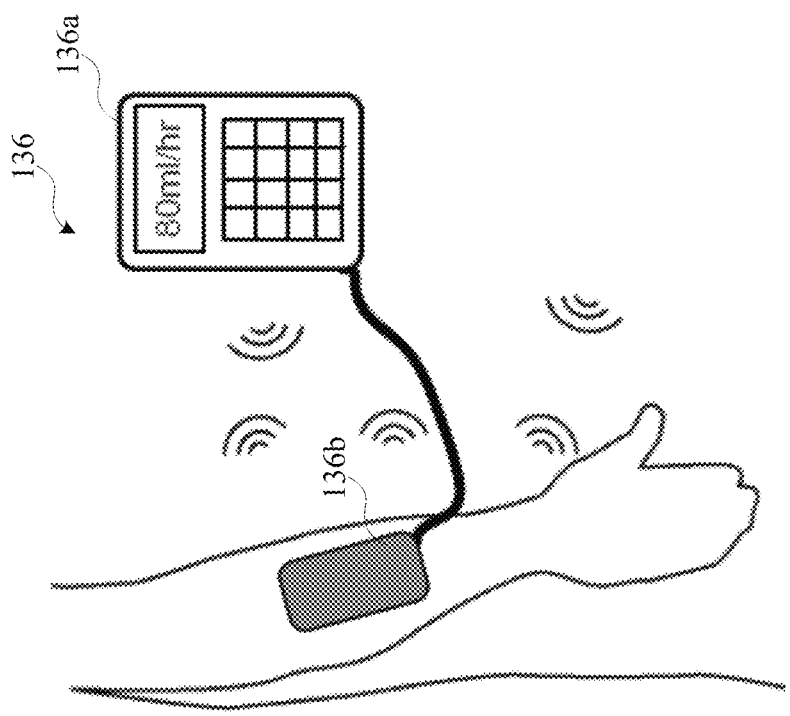
FIG. 5A illustrates aspects of an example partner device according to embodiments of the disclosure.
Figure 5B:
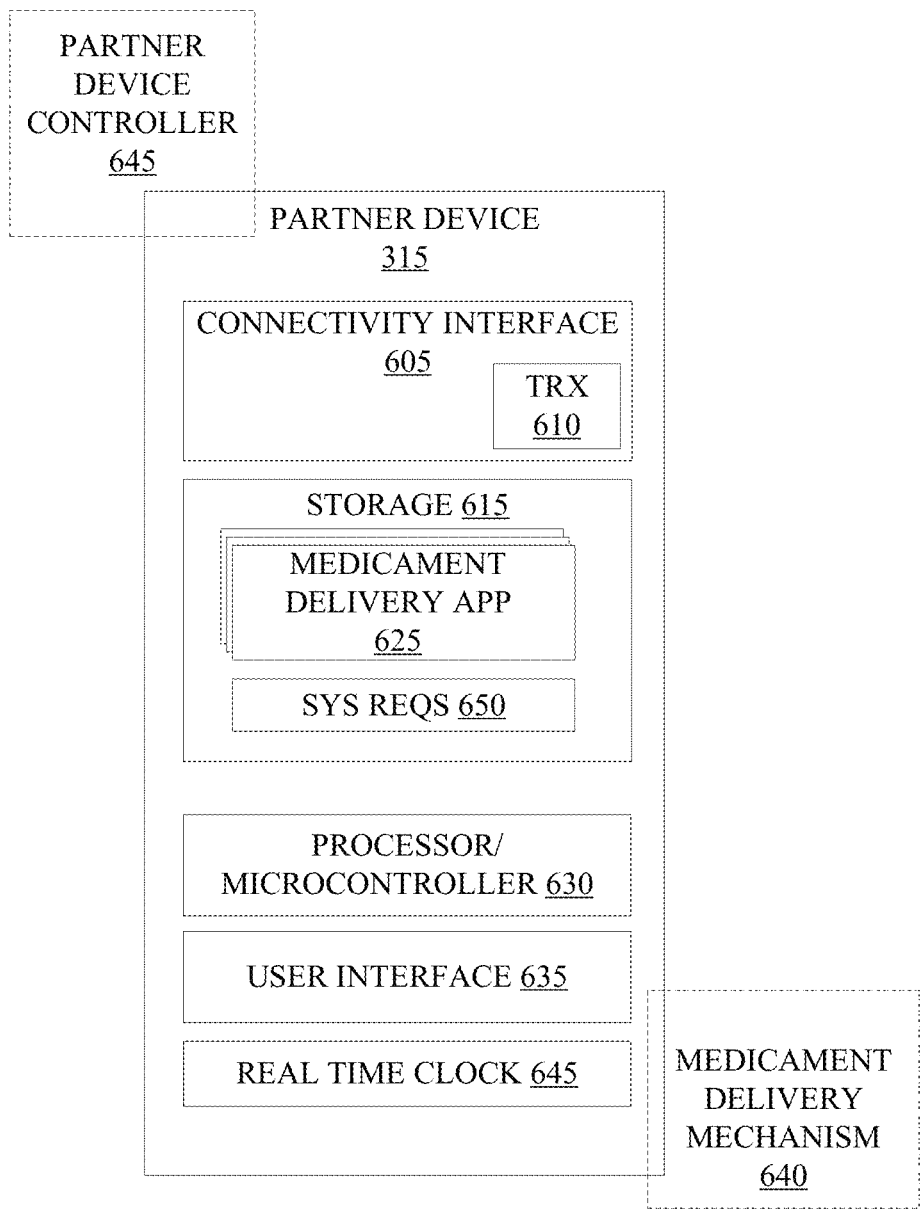
FIG. 5B illustrates aspects of an example partner device according to embodiments of the disclosure.

Further referencing FIG. 2A, server 334a may receive, collect, and/or monitor information, including analyte data, medicament data, and related information, from analyte sensor system 308, partner devices 315 and/or display devices 310, such as input responsive to the analyte data or medicament data, or input received in connection with an analyte monitoring application running on analyte sensor system 308 or display device 310 (e.g., analyte application sensor application 425a, with reference to FIG. 4), or a medicament delivery application running on display device 310 or partner device 315 (e.g., medicament delivery application 625, with reference to FIG. 5B). As such, server 334a may receive, collect, and/or monitor information from partner devices 315, such as for example information related to the provision of medicaments to a user and/or information regarding the operation of one or more partner devices 315. Server 334a also may receive, collect, and/or monitor information regarding a user of analyte sensor system 308, display devices 310, and/or partner devices 315.

In embodiments, server 334a may be adapted to receive such information via communication media 305. This information may be stored in storage 334b and may be processed by processor 334c. For example, processor 334c may include an analytics engine capable of performing analytics on information that server 334a has collected, received, etc. via communication media 305. In embodiments, server 334a, storage 334b, and/or processor 334c may be implemented as a distributed computing network, such as a Hadoop® network, or as a relational database or the like. The aforementioned information may then be processed at server 334a such that services may be provided to analyte sensor system 308, display devices 310, and/or partner devices 315, and/or a user(s) thereof. For example, such services may include diabetes management feedback for the user.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In embodiments, server 334a at least partially directs communications made over communication media 305. Such communications may include the delivery of analyte data, medicament data, and/or messaging related thereto (e.g., advertisement, authentication, command, or other messaging). For example, server 334a may process and exchange messages between and/or among analyte sensor system 308, display devices 310, and/or partner devices 315 related to frequency bands, timing of transmissions, security/encryption, alarms, alerts, notifications, and so on. Server 334a may update information stored on analyte sensor system 308, partner devices 315, and/or display devices 310, for example, by delivering applications thereto or updating the same, and/or by reconfiguring system parameters or other settings of analyte sensor system 308, partner devices 315, and/or display devices 310. Server 334a may send/receive information to/from analyte sensor system 308, partner devices 315, and/or display devices 310 in real time, periodically, sporadically, or on an event-drive basis. Further, server 334a may implement cloud computing capabilities for analyte sensor system 308, partner devices 315, and/or display devices 310.

Figure 2B:
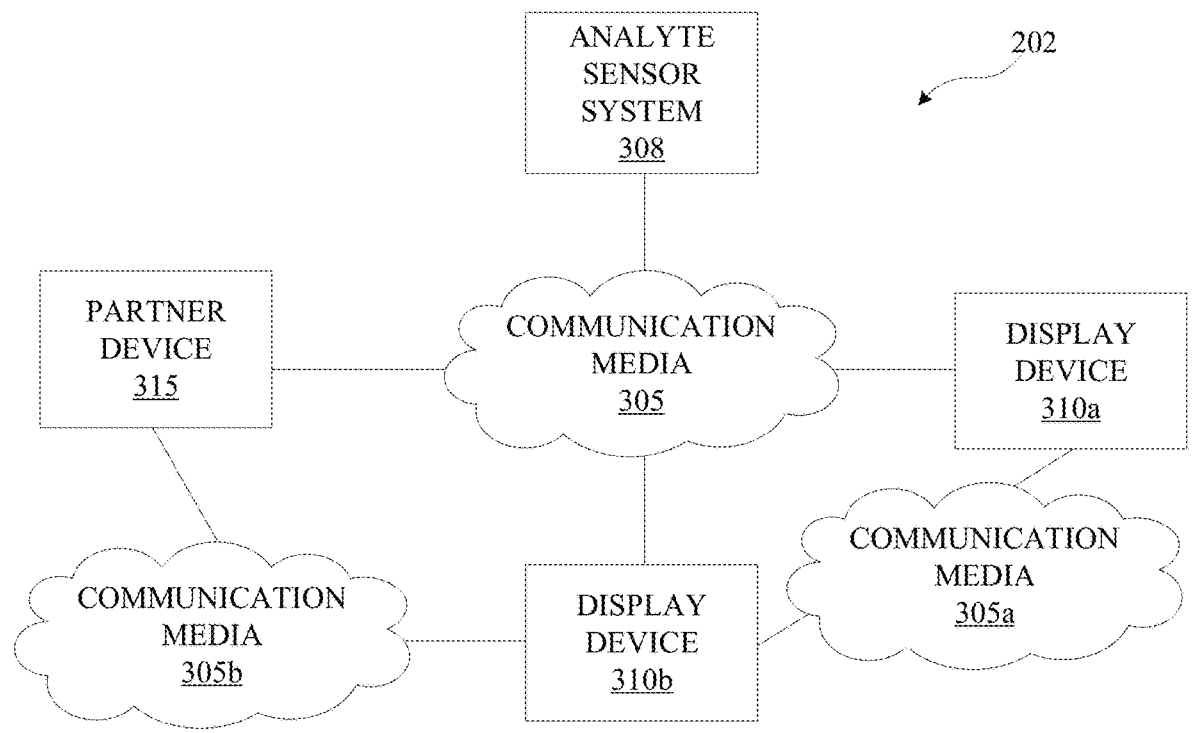
FIG. 2B illustrates aspects of an example system that may be used in connection with implementing embodiments of the disclosure.

Turning now to FIG. 2B, system 202 is depicted in accordance with embodiments of the present disclosure, some of which involve configuring and/or setting up a kind of mesh network for connecting various devices described herein. As shown, embodiments of system 202 include analyte sensor system 308 communicatively coupled to one or more of display devices 310a, 310b and/or partner device 315 via communication media 305. Display device 310a may also be communicatively coupled to display device 310b via communication media 305a. By way of example, FIG. 2B illustrates that in example implementations of the disclosure, display device 310a may connect to analyte sensor system 308 via communication media 305 using a first connection scheme and a first wireless protocol (e.g., BLE). In turn, display device 310a may also connect to display device 310b via communication media 305a using a second connection scheme and a second wireless protocol (e.g., Wi-Fi, NFC, etc.). In embodiments, the connection between display device 310a and analyte sensor system 308 may subsequently be closed, and display device 310b may establish a connection with analyte sensor system 308 while maintaining the connection with display device 310a. Further, for example, display devices 310a and 310b may exchange analyte data with one another via communication media 305a, where either or each display device 310a, 310b received the analyte data via communication medium 305, that is, from analyte sensor system 308.

Partner device 315 may also connect to display device 310b via communication media 305 and/or communication media 305b. Partner device 315 may also connect to analyte sensor system 308 via communication media 305. It will be appreciated that any number of different connection schemes/protocols may be employed for communicatively coupling the components of system 202. For example, some network connections may be available intermittently, and/or may not be available or preferable in some cases (due to device capabilities, geography, time, system conditions such as battery life or interference requirements, etc.). Thus, in some cases, partner device 315 may not directly connect to analyte sensor system 308, but rather may connect thereto indirectly via display device 310b that may be connected to analyte sensor system 308 via communication media 305. In some cases, display device 310b may not directly connect to analyte sensor system 308, but rather may connect thereto indirectly via partner device 315 that may be connected to analyte sensor system 308 via communication media 305. Additional aspects and features represented by FIG. 2B will become apparent upon studying the entirety of the present disclosure.

In embodiments, partner device 315 may not support a communication protocol utilized by analyte sensor system 308, and/or it may otherwise not be preferable for partner device 315 to directly connect to analyte sensor system 308. Thus, display device 310 (which in examples supports a communication protocol utilized by analyte sensor system 308 and/or may otherwise be more preferable for connection with analyte sensor system 308) may connect to analyte sensor system 308 and essentially act as a gateway device for partner device 315. As such, partner device 315 may receive analyte data and the like indirectly from analyte sensor system 308, and/or may exchange or information therewith. In some cases, this may be referred to as tethering. It will also be appreciated that in some cases partner device 315 may act as a gateway device for display devices 310a, 310b such that display device 310a, 310b can be tethered and can receive analyte data from analyte sensor system 308 via partner device 315. It will also be appreciated that in example implementations of system 304, one or more display devices 310a, 310b can be connected to analyte sensor system 308 in parallel with one another and/or in parallel or in series with one or more partner devices 315. Each display device 310a, 310b and/or partner device 315 may also have connected thereto a chain of display devices 310a, 310b and/or partner devices 315.

As alluded to above, wireless communication protocols may be used to transmit and receive analyte-related data, medicament-related data, and other messaging or information (e.g., control signaling and the like) among analyte sensor system 308, display device 310, partner device 315, and/or server system 334 via communication media 305. In embodiments, such wireless protocols may be designed for use in a wireless network that is optimized for periodic and small data transmissions (that may be transmitted at low rates if necessary) to and from multiple devices in a close range (e.g., a personal area network). For example, one such protocol may be optimized for periodic data transfers where transceivers may be configured to transmit data for shorter intervals and then enter low power modes for longer intervals. The protocol may have low overhead requirements both for normal data transmissions and for initially setting up communication channels (e.g., by reducing overhead) to reduce power consumption. In some embodiments, burst broadcasting schemes (e.g., one way communication) may be used. This may eliminate overhead required for acknowledgement signals and allow for periodic transmissions that consume little power. In other embodiments, passive or active proximity-based protocols may be employed to reduce overhead (e.g., overhead associated with typical pairing operations) and/or increase security, with NFC being one specific example.

The protocols may further be configured to establish communication channels with multiple devices while implementing interference avoidance schemes. In some embodiments, the example protocol mentioned above may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA/FDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies, such as WiFi, Bluetooth, and BLE. The wireless protocol may operate in various frequency bands, such as for example an open ISM band such as 2.4 GHz. Furthermore, to reduce power usage, the wireless protocol may adaptively configure data rates according to power consumption.

In embodiments relating to the configurations shown in FIG. 2B, a user interface, such as a GUI provided by user interface 435 in FIG. 4, can present to the user information regarding the mesh network, such that the user may maintain some level of control and/or input into the configuration thereof. For example, the topography/topology of the mesh network might be provided, and the user may be enabled to access connection links to alter the connection model employed, the connection parameters used, and/or the advertisement characteristics, etc. associated with the various connections. Moreover, the user may be able to switch among display devices 310 and/or partner devices 315 in terms of which device can act as a gateway to other devices. Additionally, the user, analyte sensor system 308, display device 315, and/or partner device 315 may send control signaling to other networked elements in order to manage the permissions/capabilities of other connected devices, and/or to manage the number/type of devices that can connect to analyte sensor system 308 etc. In embodiments, display device 310 and/or partner device 315 may be capable of managing the network topography/configuration in an automated fashion based on, for example, system requirements of partner device 315. In order to facilitate such automated or semi-automated management, partner device 315 may have access to mesh network configuration information via a diabetes management partner interface, as described herein.

With the above description of aspects of the presently disclosed systems and methods for wireless communication of analyte data, examples of some specific features of the present disclosure will now be provided. It will be appreciated by one of skill in the art upon studying the present disclosure that these features may be implemented using aspects and/or combinations of aspects of the example configurations described above, whether or not explicit reference is made to the same.

B. Analyte Data

Referring back to FIG. 1, as mentioned above, in embodiments, analyte sensor system 8 is provided for continuous measurement of an analyte in a host or user. By way of an overview and an example, analyte sensor system 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices (e.g., display devices 110, 120, 130, 140, partner devices 136, and/or server system 134).

Analyte sensor system 8 may include: continuous analyte sensor 10 configured to continuously measure a concentration of the analyte in the host, and sensor electronics module 12 that is typically physically connected to continuous analyte sensor 10 during sensor use. In embodiments, sensor electronics module 12 includes electronics configured to process a data stream associated with an analyte concentration measured by continuous analyte sensor 10, in order to generate sensor information that includes raw sensor data, transformed sensor data, and/or any other sensor data, for example. Sensor electronics module 12 may further be configured to generate sensor information that is customized for respective display devices 110, 120, 130, 140, partner devices 136, and/or server system 134. Sensor electronics module 12 may further be configured such that different devices may receive different sensor information, and may further be configured to wirelessly transmit sensor information to such display devices 110, 120, 130, 140, partner devices 136, and/or server system 134.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyro sine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-13 hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

C. Analyte Sensor System

As alluded to above with reference to FIG. 1, in embodiments, analyte sensor 10 includes a continuous glucose sensor, for example, a subcutaneous, transdermal (e.g., transcutaneous), or intravascular device. In embodiments, such a sensor or device can analyze a plurality of intermittent blood samples. Analyte sensor 10 can use any method of analyte measurement, including for example glucose-measurement, including enzymatic, chemical, physical, electrochemical, spectrophotometric, polarimetric, calorimetric, iontophoretic, radiometric, immunochemical, and the like.

In embodiments where analyte sensor 10 is a glucose sensor, analyte sensor 10 can use any method, including invasive, minimally invasive, and non-invasive sensing techniques (e.g., fluorescent monitoring), to provide a data stream indicative of the concentration of glucose in a host. The data stream is typically a raw data signal, which may be converted into a calibrated and/or filtered data stream that can be used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of an analyte, glucose for example, and providing an output signal that represents the concentration of the analyte, again glucose for example (e.g., as a form of analyte data).

In embodiments, analyte sensor 10 is an implantable glucose sensor, such as described with reference to U.S. Pat. No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 3A:
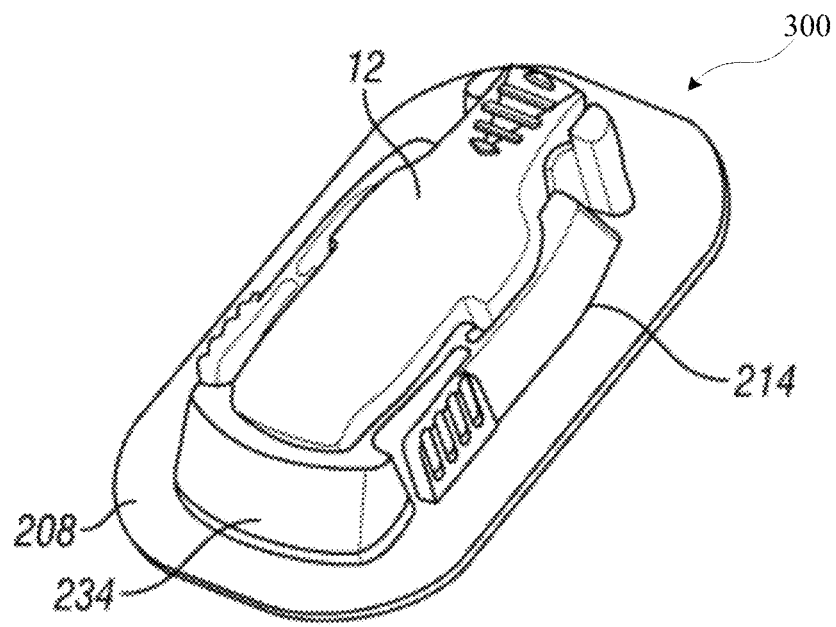
FIG. 3A is a perspective view of an example enclosure that may be used in connection with implementing embodiments of an analyte sensor system.
Figure 3B:
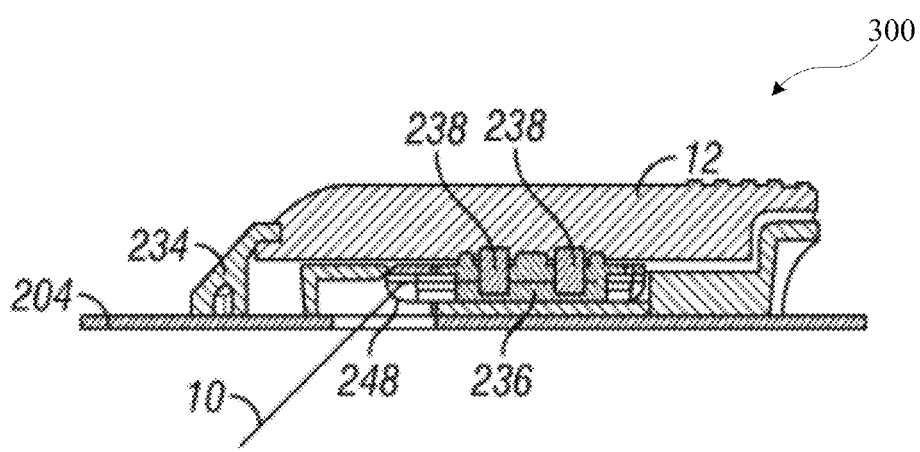
FIG. 3B is a side view of an example enclosure that may be used in connection with implementing embodiments of an analyte sensor system.

FIGS. 3A and 3B depict perspective and side views of enclosure 200 that may be used in connection with implementing embodiments of analyte sensor system 8, according certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In embodiments, mounting unit 214, also referred to as a housing or sensor pod, includes base 234 adapted for fastening to a host's or user's skin. Base 234 can be formed from a variety of hard or soft materials, and can include a low profile for minimizing protrusion of the device from the host during use. In embodiments, base 234 is formed at least partially from a flexible material, which may provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In embodiments, a detachable connection between mounting unit 214 and sensor electronics module 12 is provided, which may enable improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In embodiments, sensor electronics module 12 is configured with signal processing (programming), for example, configured to filter, calibrate, and/or execute other algorithms useful for calibration and/or display of sensor information. However, an integral (non-detachable) sensor electronics module can be similarly configured.

In embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In embodiments, contacts 238 are formed from a conductive elastomeric material, such as a carbon black elastomer, through which sensor 10 extends.

With further reference to FIGS. 3A and 3B, in embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). Certain embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of embodiments described herein are disclosed in U.S. Patent Publication No. US-2009-0240120-A1, which is incorporated herein by reference in its entirety.

Figure 3C:
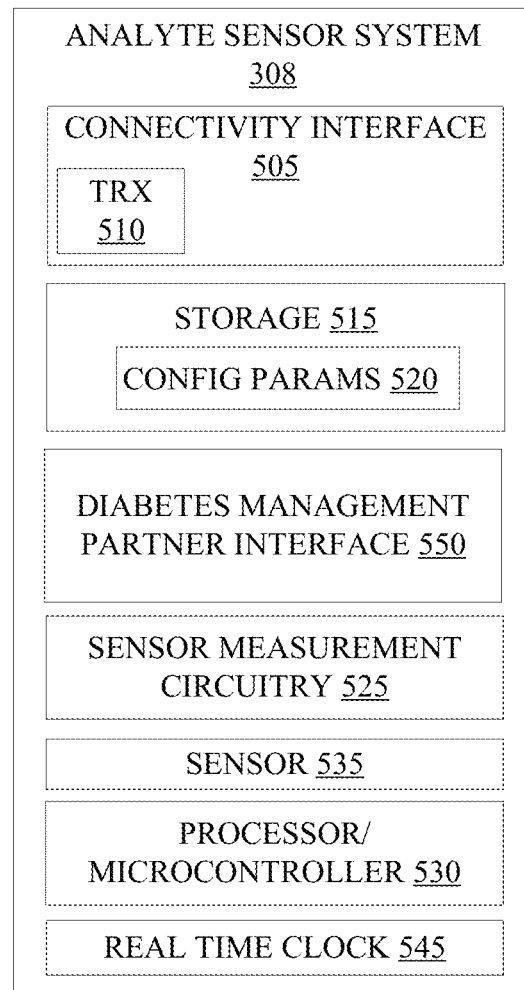
FIG. 3C illustrates aspects of an example analyte sensor system according to embodiments of the disclosure.

Turning now to FIG. 3C, a more detailed functional block diagram of analyte sensor system 308 (discussed above for example in connection with FIGS. 2A, 2B) is provided. As shown in FIG. 3C, analyte sensor system 308 may include analyte sensor 535 (e.g., which may also be designated with the numeral 10 in FIG. 1) coupled to sensor measurement circuitry 525 for processing and managing sensor data. Sensor measurement circuitry 525 may be coupled to processor/microprocessor 530 (e.g., which may be part of item 12 in FIG. 1). In some embodiments, processor 530 may perform part or all of the functions of sensor measurement circuitry 525 for obtaining and processing sensor measurement values from sensor 535.

Processor 530 may be further coupled to a radio unit or transceiver 510 (e.g., which may be part of item 12 in FIG. 1) for sending sensor and other data and receiving requests and commands and other signaling from an external device, such as display device 310, which may be used to display or otherwise provide the sensor data (or analyte data) or data derived therefrom to a user, server system 334, and/or partner device 315, which may utilize sensor data or a derivative data derived therefrom in the administration of medicaments (e.g., insulin) and/or diabetes management guidance to the user. As used herein, the terms "radio unit" and "transceiver" may be used interchangeably and generally refer to a device that can wirelessly transmit and receive data.

Analyte sensor system 308 may further include storage 515 (e.g., which may be part of item 12 in FIG. 1) and real time clock (RTC) 545 (e.g., which may be part of item 12 in FIG. 1), for storing and tracking sensor and other data. For example, storage 515 may store configuration parameters 520. In general, configuration parameters 520 relate to the operation of analyte sensor system 308, and in embodiments particularly relate to the operation of analyte sensor system 308 vis-à-vis partner device 315 and/or display device 315. In embodiments, configuration parameters 520 may be accessed by partner device 315 (directly or indirectly) using diabetes management partner interface 550. In this manner, configuration parameters 520 may be set and/or modified according to system requirements 650 (referencing FIG. 5B) of partner device 315. For example, configuration parameters 520 may be modified such that analyte sensor system 308, display device 310, and/or partner device 315 operate in such a way that one or more system requirements 650 of partner device 315 are met.

As mentioned above, with further reference to FIG. 3C, embodiments of analyte sensor system 308 include diabetes management partner interface (DMPI) 550. Diabetes management partner interface 550 may allow partner device 315 that is connected to analyte sensor system 308 to set and/or configure/modify configuration parameters 520 so that system requirements 650 of partner device 315 may be met in the operation of analyte sensor system 308, display device 310, and/or partner device 315. DMPI 550 may provide partner device 315 access to configuration parameters 520 for the configuration of the same. Where partner devices 315 and/or display devices 310 are offered by different manufacturers and have different design goals/constraints, DMPI 550 enables a flexible system wherein configuration parameters 520 of analyte sensor system 308 may be accessed, set, and/or modified according to the respective system requirements and/or design constraints of partner devices 315 and/or display devices 310. This flexibility can improve the integration and interoperability of such devices, resulting in a more usable and versatile ecosystem. Additional aspects of DMPI 550 will be discussed further below.

Although not expressly shown in FIG. 3C, embodiments of analyte sensor system 308 also include an interface specifically for display devices 310 (as differentiated from partner device 315). This interface may be a wireless interface that allows display device 310 to connect to analyte sensor system 308 and access, set, and/or modify/configure configuration parameters 520 thereof in order to facilitate communications with analyte sensor system 308. As will be discussed further in connection with FIGS. 10A and 10B, this interface may be part of or implemented within DMPI 550 (e.g., as DMPI 750a) or may be separately implemented. In embodiments, the DMPI 550 is reconfigurable for accommodation of characteristics of display devices 310 and/or partner devices 315 that may connect to analyte sensor system 308, as well as accommodation of system-wide requirements and dynamics of, for example, system 200 (referencing FIG. 2A).

Some components of analyte sensor system 308 may require replacement periodically. For example, analyte sensor system 308 may include an implantable sensor 535 that may be attached to a sensor electronics module that includes sensor measurement circuitry 525. Additionally, analyte sensor system 308 may include processor 530, storage 515, and transceiver 510, and a battery (not shown). Sensor 535 may require periodic replacement (e.g., every 7 to 30 days). The sensor electronics module may be configured to be powered and active for much longer than sensor 535 (e.g., for 3 to 6 months or more) until the battery needs replacement. Replacing these components may be difficult and may require the assistance of trained personnel. Reducing the need to replace such components, particularly the battery, can significantly improve the convenience and cost of using analyte sensor system 308, including to the user. In embodiments, when a sensor electronics module is used for the first time (or reactivated once a battery has been replaced in some cases), it may be connected to sensor 535 and a sensor session may be established. As will be further described below, there may be a process for initially establishing communication between display device 310 and the sensor electronics module when the module is first used or reactivated (e.g., after the battery is replaced). Once display device 310 and the sensor electronics module have established communication, display device 310 and the sensor electronics module may periodically and/or continuously be in communication over the life of several sensors 535 until, for example, the battery needs to be replaced. Each time sensor 535 is replaced, a new sensor session may be established. The new sensor session may be initiated through a process completed using display device 310 and the process may be triggered by notifications of a new sensor 535 via the communication between the sensor electronics module and display device 310 that may be persistent across sensor sessions.

Analyte sensor system 308 in example implementations gathers analyte data using sensor 535 and transmits the same or a derivative thereof to display device 310, partner device 315, and/or server system 334. Data points regarding analyte values may be gathered and transmitted over the life of sensor 535. New measurements and/or related information may be transmitted often enough for a remote device/individual to adequately monitor analyte (e.g., glucose) levels.

It is to be appreciated that many details of the processing, gathering, and exchanging data by analyte sensor system 308, partner devices 315, and/or display device 310 etc. are provided elsewhere herein. It will be appreciated upon studying the present disclosure that analyte sensor system 308 may contain several like components that are described with respect to FIGS. 4 and 5B, at least for some embodiments herein. The details and uses of such like components may therefore be understood vis-à-vis analyte sensor system 308 even if not expressly described here with reference to FIG. 3C.

D. Display Devices

Referring by way of example again to FIG. 1, aspects of display devices 110, 120, 130, and 140 that may be used in system 100 will now be described. In embodiments of the present disclosure, sensor electronics module 12 is configured to search for and/or attempt wireless communication with a display device from a list of display devices. By way of an overview and an example, a typical display device 110, 120, 130, 140 can communicate wirelessly with analyte sensor system 8, including for authentication of display devices 110, 120, 130, 140 and/or analyte sensor system 8, as well as the exchange of analyte data and control signaling.

In embodiments, sensor electronics module 12 is configured to search for and/or attempt wireless communication with a list of display devices 110, 120, 130, 140 in a predetermined and/or programmable order (e.g., grading and/or escalating), for example, wherein a failed attempt at communication with and/or alarming with a first one of display devices 110, 120, 130, 140 triggers an attempt at communication with and/or alarming with a second one of display devices 110, 120, 130, 140, and so on. In example embodiments, sensor electronics module 12 is configured to search for and attempt to alarm a host or care provider sequentially using a list of display devices 110, 120, 130, 140, such as: (1) a default display device (e.g., one of display devices 110, 120, 130, 140) or a custom analyte monitoring device (e.g., display device 110); (2) a mobile phone (e.g., display device 120) via auditory, haptic, and/or visual methods, such as text message to the host and/or care provider, voice message to the host and/or care provider, and/or 911; (3) a tablet (e.g., display device 130); (4) a smart watch (e.g., display device 140). Of course, other types of display devices are encompassed and/or described herein, and alarms may additionally or alternatively be sent to partner devices 136 and/or server system 334.

Depending on the embodiment, one or more display devices 110, 120, 130, 140 that receive data packages from sensor electronics module 12 can be adapted to be "dummy displays," wherein they display the displayable sensor information received from sensor electronics module 12 without additional processing (e.g., prospective algorithmic processing that may be necessary for real-time display of sensor information). In embodiments, the displayable sensor information comprises transformed sensor data that does not require processing by the display device prior to display of the displayable sensor information. Some display devices 110, 120, 130, 140 may include software including display instructions (software programming that includes instructions configured to display the displayable sensor information and optionally query sensor electronics module 12 to obtain the displayable sensor information) configured to enable display of the displayable sensor information thereon. In embodiments, display device 110, 120, 130, 140 is programmed with the display instructions at the manufacturer and can include security and/or authentication to avoid plagiarism of display device 110, 120, 130, 140 and/or unauthorized access thereof. In embodiments, display device 110, 120, 130, 140 is configured to display the displayable sensor information via a downloadable program (for example, a downloadable Java Script via the Internet), such that any display device 110, 120, 130, 140 that supports downloading of a program (for example, any display device 110, 120, 130, 140, such as, e.g., mobile phones, tablets, PDAs, PCs, and the like, that supports Java applets) therefore can be configured to display displayable sensor information.

In embodiments, certain display devices 110, 120, 130, 140 may be in direct wireless communication with sensor electronics module 12, but intermediate network hardware, firmware, and/or software can be included within the direct wireless communication path. In embodiments, a repeater (e.g., a Bluetooth repeater) can be used to re-transmit the transmitted displayable sensor information to a location farther away than the immediate range of the telemetry module of sensor electronics module 12, wherein the repeater enables direct wireless communication when substantive processing of the displayable sensor information does not occur. In embodiments, a receiver/transmitter (e.g., Bluetooth receiver/transmitter) can be used to re-transmit the transmitted displayable sensor information, possibly in a different format, such as in a text message onto a TV screen, wherein the receiver/transmitter enables direct wireless communication when substantive processing of the sensor information does not occur. In embodiments, sensor electronics module 12 directly wirelessly transmits displayable sensor information to one or a plurality of display devices 110, 120, 130, 140, such that the displayable sensor information transmitted from sensor electronics module 12 is received by one or more of display devices 110, 120, 130, 140 without intermediate processing of the displayable sensor information.

In embodiments, one or more display devices 110, 120, 130, 140 include built-in authentication mechanisms, wherein authentication may be required for communication between sensor electronics module 12 and display device 110, 120, 130, 140. In embodiments, to authenticate the data communication between sensor electronics module 12 and display devices 110, 120, 130, 140, a challenge-response protocol, such as key authentication is provided, where the challenge is a request for the key or a hash or other value based on or derived from the key, and the valid response is the correct key or a hash or other value based on or derived from the key, such that pairing of sensor electronics module 12 with display devices 110, 120, 130, 140 can be accomplished by the user and/or manufacturer via the key. This may be referred to in some cases as two-way authentication. The key may be a software or hardware level key. Additionally, the key may be a password (e.g., randomly generated or set by a user or other entity), and/or may be derived from uniquely identifying features (e.g., finger print, facial, or retinal information) or information, etc.

In embodiments, one or more display devices 110, 120, 130, 140 are configured to query sensor electronics module 12 for displayable sensor information, wherein display device 110, 120, 130, 140 acts as a master device requesting sensor information from sensor electronics module 12 (e.g., a slave device) on-demand, for example, in response to a query. Although in some cases display device 110, 120, 130, 140 acts as a master and sensor electronics module 12 acts as a slave, in other cases, these roles may be reversed. For example, the roles can reverse depending on the nature of the communication and so on.

In embodiments, sensor electronics module 12 is configured for periodic, systematic, and/or regular transmission of sensor information to one or more display devices 110, 120, 130, 140 (for example, every 1, 2, 5, or 10 minutes or more or less). In embodiments, sensor electronics module 12 is configured to transmit data packages associated with a triggered alert (e.g., triggered by one or more alert conditions). However, any combination of the above described statuses of data transmission can be implemented with any combination of paired sensor electronics module 12 and display device(s) 110, 120, 130, 140. For example, one or more display devices 110, 120, 130, 140 can be configured for querying sensor electronics module 12 (directly or indirectly) and for receiving alarm information triggered by one or more alarm conditions being met. Additionally, sensor electronics module 12 can be configured for periodic transmission of sensor information to one or more display devices 110, 120, 130, 140 (the same or different display devices as described in the previous example), whereby a system can include display devices 110, 120, 130, 140 that function differently with regard to how sensor information is obtained.

In embodiments, a display device 110, 120, 130, 140 is configured to query the data storage memory in sensor electronics module 12 (e.g., storage 515 with reference to FIG. 3C) for certain types of data content, including direct queries into a database in a memory or storage of sensor electronics module 12 and/or requests for configured or configurable packages of data content therefrom; namely, the data stored in sensor electronics module 12 can be configurable, queryable, predetermined, and/or pre-packaged, based on characteristics and/or requests of display device 110, 120, 130, 140 with which sensor electronics module 12 is communicating. In additional or alternative embodiments, sensor electronics module 12 generates the displayable sensor information based on information known to sensor electronics module 12 regarding which display device 110, 120, 130, 140 is to receive a particular transmission. Additionally, some display devices 110, 120, 130, 140 may be capable of obtaining calibration information and wirelessly transmitting the calibration information to sensor electronics module 12, such as through manual entry of the calibration information, automatic delivery of the calibration information, and/or an integral reference analyte monitor incorporated into display device 110, 120, 130, 140. U.S. Patent Publication Nos. 2006/0222566, 2007/0203966, 2007/0208245, and 2005/0154271, all of which are incorporated herein by reference in their entireties, describe systems and methods for providing an integral reference analyte monitor incorporated into a display device (e.g., display device 110, 120, 130, 140) and/or other calibration methods that can be implemented with embodiments disclosed herein. In embodiments, some display devices 110, 120, 130, 140 are capable of transmitting the calibration information to partner device(s) 136.

In general, a plurality of display devices (e.g., a custom analyte monitoring device, which may also be referred to in some instances analyte display device 110, mobile phone 120, tablet 130, smart watch 140, a reference analyte monitor, a drug delivery or medicament device, a medical device, and a personal computer etc.) may be configured to wirelessly communicate with sensor electronics module 12. The plurality of display devices 110, 120, 130, 140 may be configured to display at least some of the displayable sensor information wirelessly communicated from sensor electronics module 12. The displayable sensor information may include sensor data, such as raw data and/or transformed sensor data, such as analyte concentration values, rate of change information, trend information, alert information, sensor diagnostic information and/or calibration information, for example. In embodiments, display device 110, 120, 130, 140 may receive analyte data from analyte sensor system 8 indirectly via another device (e.g., partner device 136 and/or server system 134). In embodiments, display device 110, 120, 130, 140 may send commands or other control/configuration signaling to analyte sensor system 8 indirectly via another device (e.g., partner device 136 and/or server system 134). Alerts, alarms, and/or notifications related to the analyte data may also be provided (whether visually, audibly, and/or haptically) using display devices 110, 120, 130, 140. Additional types of information that may be received at display devices 110, 120, 130, 140 may include information related to battery life or power consumption, other diagnostics, timing, and so forth.

In some instances, display device 110, 120, 130, 140 that has successfully communicated with analyte sensor system 8 and successfully completed an authentication process can be considered as an approved display device 110, 120, 130, 140. In some instances, display device 110, 120, 130, 140 may be configured in a display only state, where display device 110, 120, 130, 140 can access analyte data in a read and display manner. In this state, display device 110, 120, 130, 140 typically does not send to analyte sensor system 8 commands related to continuous glucose monitoring (CGM). Nevertheless, other commands may be sent in this state. Example CGM commands include commands to start, stop, or calibrate a CGM sensor session in which the analyte sensor system 8 is used to generate analyte data. Examples of non-CGM commands include commands that do not affect the calculation of CGM data. Such non-CGM commands include, for example, a command to change advertising parameters, to modify whitelist criteria, and to add an additional display device 110, 120, 130, 140 in read only mode. Examples of display devices 110, 120, 130, 140 that may typically operate in the display only state include a small device such as a key fob, where the key fob displays analyte data and alerts/alarms/notifications related thereto. In some circumstances, however, any display device 110, 120, 130, 140 may operate in the display only state, as will be described herein.

In some instances, display device 110, 120, 130, 140 may be configured in a display and control state, where in addition to accessing analyte data in a read and display manner, display device 110, 120, 130, 140 can send commands related to CGM, as well as other commands. In this state, other types of data may be readable/displayable, and as mentioned, display device 110, 120, 130, 140 can send various types of commands to analyte sensor system 12 in addition to CGM commands.

FIG. 4 depicts example aspects of the present disclosure that may be used in connection with implementing display device 310 that is connectable to, for example, analyte sensor system 308 and/or partner device 315. It is to be appreciated that many details of the processing, gathering, and exchanging data by analyte sensor system 308, partner devices 315, and/or display device 310 etc. are provided elsewhere herein. It will be appreciated upon studying the present disclosure that display device 310 may contain several like components that may have are described with respect to FIG. 3C and/or FIG. 5B, at least for embodiments. The details and uses of such like components may therefore be understood vis-à-vis display device 310 even if not expressly described here with reference to FIG. 4.

As illustrated in FIG. 4, display device 310 may include a number of components for communicatively coupling with analyte sensor system 308 and/or partner device 315 via communication media 305. Display device 310 may be used for alerting a user and/or for providing sensor information or analyte data, control signaling, and/or other information (e.g., relating to partner device 315 and/or the delivery of medicaments) to the user and/or analyte sensor system 308, another display device 310, and/or partner device 315. Display device 310 may include one or more of connectivity interface 405 (which in turn includes transceiver 320), storage 415 (which in turn stores analyte sensor application 425*a*, partner device application 425*b*, and/or additional applications), processor/microprocessor 430 for processing and managing sensor and/or other data, user interface 435 (e.g., a man-machine interface, audio or visual interface (display, LEDs, speakers, microphone, and the like), haptic feedback, etc.) that may be used to provide/present information to a user and/or receive input from the user, and real time clock (RTC) 445. A bus (not shown here) may be used to interconnect the various elements of display device 310 and transfer data between these elements.

Transceiver 410 may be used for receiving sensor and/or other data and for sending/receiving requests, instructions, other signaling, and/or data to/from analyte sensor system 308, partner device 315, and/or server system 334. Transceiver 410 may employ a communication protocol for sending and receiving the aforementioned information. In embodiments, when a standardized communication protocol is used for communications with (to/from) display device 310, commercially available transceiver circuits may be utilized in transceiver 410 that incorporate processing circuitry to handle low level data communication functions such as the management of data encoding, transmission frequencies, handshake protocols, and the like. In these embodiments, processor 430 may but does not necessarily need to manage these activities, but rather can provide desired data values for transmission, and manage high level functions such as power up or down, setting a rate at which messages are transmitted, and the like. Instructions and data values for performing these high level functions can be stored in storage 415 and provided to the transceiver circuits via a data bus and transfer protocol established by the manufacturer of the transceiver 410.

Connectivity interface 405 can be used to interface display device 310 to communication media 305, such that display device 310 may be communicatively coupled (directly or indirectly) to analyte sensor system 308, another display device 310, and/or partner device 315 via communication media 305 (for example with reference to FIG. 2A). Transceiver 410 of connectivity interface 405 may include multiple transceiver modules operable on different wireless standards and/or frequency bands. Transceiver 410 may be used to send/receive analyte or medicament delivery data and/or associated commands and messages to/from analyte sensor system 308, as well as to wirelessly communicate with partner device 315. Additionally, connectivity interface 405 may in some cases include additional components for controlling radio and/or wired connections, such as baseband and/or Ethernet modems, audio/video codecs, and so on.

Storage 415 may be used for storing an operating system for display device 310 and/or a custom (e.g., proprietary) application designed for wireless data communication between a remote transceiver and display device 310. Storage 415 may be a single memory device or multiple memory devices and may be a volatile or non-volatile memory for storing data and/or instructions for software programs and applications. The instructions may be executed by processor/microprocessor 430, for example to control and manage transceiver 410, user interface 435, applications 425*a*, 425*b*, and/or other components of display device 310. Storage 415 may include volatile memory (e.g., RAM) and/or non-volatile memory (e.g., flash storage), may include any of EPROM, EEPROM, cache, and/or may include some combination/variation thereof. In various embodiments, storage 415 may store user input data and/or other data collected by display device 310 (e.g., input from other users gathered via analyte sensor application 425*a* and/or partner device application 425*b*, and/or information related to partner device 315, including medicament delivery data and associated information). Storage 415 may also be used to store volumes of analyte-related data received from analyte sensor system 308 and/or volumes of medicament-related data received from partner device 315, for later retrieval and use, e.g., for determining trends and/or triggering alerts. Additionally, storage 415 may store analyte sensor application 425*a* and/or partner device application 425*b* that, when executed using processor 430, for example, receive input (e.g., by a conventional hard/soft key or a touch screen, voice detection, or other input mechanism or user interface 435), and allows a user to interact with the analyte-related data and related content, and/or medicament-related data and related content, and/or other information (e.g., related to system configurations), for example via a GUI.

In embodiments, a user may interact with analyte sensor application 425*a* and/or partner device application 425*b* via a GUI, which may be provided by a display of user interface 435 of display device 310. The GUI of display device 310 may perform such functions as accepting user input and displaying menus as well as information derived from analyte data or medicament data, for example. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. By way of example, the display may be a touchscreen display that accepts various hand gestures as inputs.

In embodiments, application 425*a* may process and/or present analyte-related data received by display device 310, according to various operations described herein, and present such data via the display of user interface 435. Additionally, application 425*a* may be used to obtain, access, display, control, and/or interface with analyte data and related messaging and processes associated with analyte sensor system 308, as is described in further detail herein.

Application 425*a* may be downloaded, installed, and initially configured/setup on display device 310. For example, display device 310 may obtain application 425*a* from server system 334, or from another source accessed via communication media 305, such as an application store or the like. Following installation and setup, application 425*a* may be used to access and/or interface with analyte data (e.g., whether stored on server system 334, locally from storage 415, or from analyte sensor system 308). By way of illustration, application 425*a* may present a menu that includes various controls or commands that may be executed in connection with the operating of analyte sensor system 308 and one or more display devices 310. Application 425*a* may also be used to interface with or control other display devices 310, and/or with partner device 315, for example, to deliver or make available thereto analyte-related data, including for example by receiving/sending analyte data directly to the other display device 310 and/or partner device 315, and/or by sending an instruction for analyte sensor system 308 and the other display device 310 and/or partner device 315 to be connected, etc., as will be described herein. Additionally, application 425*a* in some implementations may interact with one or more additional applications supported by display device 310, for example to retrieve or supply relevant data. Such applications may include, by way of example, fitness/lifestyle monitoring applications, social media applications, and so on. Such applications may also include applications associated with partner device 315, including partner device application 425b, which will be described in detail below.

Analyte sensor application 425a may involve various code/functional modules, such as, for example, a display module, a menu module, a list module, and so on as will become clear in light of the description of various functionalities herein (e.g., in connection with disclosed methods). These modules may be implemented separately or in combination. Each module may include (non-transitory) computer-readable media and have computer-executable code stored thereon, such that the code may be operatively coupled to and/or executed by processor 430 (which, e.g., may include a circuitry for such execution) to perform specific functions (e.g., as described herein with regard to various operations and flow charts etc.) with respect to interfacing with analyte-related data and performing tasks related thereto, as well as to interface with other applications/devices.

As will be further described below, a display module may present (e.g., via a display of user interface 435) various screens to a user, with the screens containing graphical representations of information provided by application 425a. In further embodiments, application 425a may be used to display to the user an environment for viewing and interacting with various display devices 310 that may be connectable to analyte sensor system 308, as well as with analyte sensor system 308 itself, and/or with partner device 315. Sensor application 425a may include a native application modified with a software design kit (e.g., depending on the operating system) in order to carry out the functionalities/features described herein.

With further reference to FIG. 4, partner device application 425b may also be included in storage 415 and, when executed using processor 430 for example, application 425b may be used to receive input (e.g., by a conventional hard/soft key or a touch screen, voice detection, or other input mechanism or user interface 435), and can allow a user to interact with the medicament-related data and related content, for example via a GUI of user interface 435. Application 425b may process and/or present medicament-related and other partner device or system data received by or sent from display device 310, according to various operations described herein, and present such data via the display of user interface 435. Additionally, application 425b may be used to obtain, access, display, control, and/or interface with medicament, analyte, and/or other data and related messaging and processes associated with partner device 315, display device 310, and/or server system 334, as is described in further detail herein.

In embodiments, application 425b may be downloaded, installed, and initially configured/setup on display device 310. For example, display device 310 may obtain application 425b from server system 334, where application 425b may be provided by a manufacturer of partner device 315 in some cases, or from another source accessed via communication media 305, such as an application store or the like. Following installation and setup, application 425b may be used to access and/or interface with partner device 315, including medicament-related data (e.g., whether stored on server system 334, locally from storage 415, or from partner device 315 and/or analyte sensor system 308). By way of illustration, application 425b may cause user interface 435 to present a menu that includes various controls or commands that may be executed in connection with the operating of partner device 315, analyte sensor system 308, and/or one or more display devices 310.

Application 425b may also be used to interface with or control other display devices 310, and/or with partner device 315 vis-à-vis the operation of partner device 315 in the systems/ecosystems described herein, for example, to receive/deliver or make available medicament-related data, including for example by receiving medicament-related data from partner device 315 and/or analyte sensor system 308, and/or by sending an instruction for analyte sensor system 308 and/or partner device 315 to be connected or operate in a particular manner, etc., as will be described herein. Additionally, application 425b in some implementations may interact with one or more additional applications supported by display device 310, for example to retrieve or supply relevant data. Such applications may include, by way of example, fitness/lifestyle monitoring applications, social media applications, and so on. Such applications may also include applications associated with analyte sensor system 308 and/or display device 310, including analyte sensor application 425a. By way of example, communication between analyte sensor application 425a and partner device application 425b may facilitate the sharing and coordination of alert information originating from analyte sensor system 308 and/or partner device 315.

Partner device application 425b may include various code/functional modules, such as, for example, a display module, a menu module, a list module, and so on as will become clear in light of the description of various functionalities herein (e.g., in connection with disclosed methods). These modules may be implemented separately or in combination. Each module may include (non-transitory) computer-readable media and have computer-executable code stored thereon, such that the code may be operatively coupled to and/or executed by processor 430 to perform specific functions with respect to interfacing with partner device 315, display device 310, server system 334, and/or medicament-related or analyte-related data or other information, and/or performing tasks related thereto, as well as to interface with other applications/devices.

As will be further described below, a display module may present (e.g., via a display of user interface 435) various screens to a user, with the screens containing graphical representations of information provided by application 425b. In further embodiments, application 425b may be used to display to the user an environment for viewing and interacting with various partner devices 315 that may be connectable to analyte sensor system 308 and/or display device 310. Sensor application 425b may include a native application modified with a software design kit (e.g., depending on the operating system) in order to carry out the functionalities/features described herein. Such software design kits may be provided by the manufacturer of partner device 315, or by other entities.

As illustrated in FIG. 4, storage 415 of display device 310 may also include configuration parameters 420. Configuration parameters 420, in embodiments, govern aspects of wireless communication between/among display device 310, analyte sensor system 308, and/or partner device 315. Configuration parameters 420 will be described in further detail below, for example with reference to FIGS. 5B, 8, 9A-9S, 10A, and 10B, etc. System requirements 450 may also be stored in storage 415. System requirements 450 may pertain to partner device 315, and will be described in further detail with reference to FIGS. 5B, 8, 9A-9S, 10A, and 10B, by way of example.

Referring again to FIG. 4, as discussed above, display device 310 also includes processor/microcontroller 430. Processor 430 may include processor sub-modules, including, by way of example, an applications processor that interfaces with and/or controls other elements of display device 310 (e.g., connectivity interface 405, applications 425a, 425b, user interface 435 and components thereof, RTC 445, etc.). Processor 430 may include a controller and/or microcontroller that provides various controls (e.g., interfaces with virtual buttons/inputs and switches etc.) related to device management, such as, for example, lists of available or previously paired devices, information related to measurement values, including analytes and medicaments, information related to network conditions (e.g., link quality and the like), information related to the timing, type, and/or structure of messaging exchanged among analyte sensor system 308, display device 310, and/or partner device 315, information related to diagnostics of various systems, information related to power management of analyte sensor system 308, display device 310, and/or partner device 315, and so on. Additionally, the controller may include various controls related to the gathering of user input, such as, for example, a user's finger print (e.g., to authorize the user's access to data or to be used for authorization/encryption of data, including analyte data) or other identifying information, as well as analyte data and/or medicament delivery data and/or related information.

Processor 430 may include circuitry such as logic circuits, memory, a battery and power and related management circuitry, and other circuitry drivers for periphery components and audio/video and other components of display device 310. Display device 310 may include other peripheral components not shown in detail in FIG. 4, and processor 430 may be adapted to drive such peripheral components. Processor 430 and any sub-processors thereof may include logic circuits for receiving, processing, and/or storing data received and/or input to display device 310, and data to be transmitted or delivered by display device 310. Processor 430 may be coupled (e.g., by a bus) to user interface 435 as well as connectivity interface 405 and storage 415 (including applications 425a, 425b). Hence, processor 430 may receive and process electrical signals generated by these respective elements and thus perform various functions. By way of example, processor 430 may access stored content from storage 415 at the direction of application 425a and/or 425b, and process the stored content for display and/or output by a display or other mechanism of user interface 435. Additionally, processor 430 may process the stored content for transmission via connectivity interface 405 and communication media 305 to other display devices 310, analyte sensor system 308, server system 334, and/or partner device 315.

In embodiments, processor 430 may further obtain, detect, calculate, and/or store data input by a user via user interface 435, or data received from analyte sensor system 308 (e.g., analyte sensor data and related messaging) and/or partner device 315 (e.g., medicament delivery data and related data/messaging), over a period of time. Processor 430 may use this input to gauge the user's physical and/or mental response to the analyte, medicament, or data, as well as other factors (e.g., time of day, location, etc.). In various embodiments, the user's response or other factors may indicate preferences with respect to the use of certain display devices 310 and/or partner devices 315 under certain conditions, preferred dosages under certain conditions, and/or the use of certain connection/transmission schemes under various conditions, as will be described in further detail herein.

E. Partner Devices

Referring again to FIG. 1, in embodiments of the present disclosure, the above-described sensor electronics module 12 is configured to search for and/or attempt wireless communication with partner device 136. By way of an overview and an example, a typical partner device 136 can communicate wirelessly with analyte sensor system 8, including for authentication of partner device 136 and/or analyte sensor system 8, as well as the exchange of analyte data, medicament data, other data, and/or control signaling. Partner devices 136 may include a passive device in example embodiments of the disclosure.

FIG. 5A illustrates one example of partner device 136, which as shown may be an insulin pump for administering insulin to a user. For a variety of reasons, it may be desirable for such an insulin pump to receive and track glucose values transmitted from analyte sensor system 8 (with reference to FIG. 1 for example). One reason for this is to provide the insulin pump a capability to suspend/activate insulin administration based on a glucose value being below/above a threshold value. One example solution that allows a passive device (e.g., partner device 136) to receive analyte data (e.g., glucose values) without being bonded to analyte sensor system 8, is to include the analyte data in the advertisement messages transmitted from analyte sensor system 8 (as discussed by way of example with reference to FIG. 7C). The data included in the advertisement messages can be encoded so that only a device that has the identification information associated with analyte sensor system 8 can decode the analyte data.

Partner device 136 may include input/output portion 136a, in which, for example, glucose and other values may be displayed and input may be received via buttons, wireless connection, or other mechanisms, including a variety of user interface features. Partner device 136 may also include attachment portion 136b that interfaces with the user to, for example, administrate insulin responsive to the input received at input/output portion 136a. In some cases, attachment portion 136b may provide sensory alerts or other notifications to the user based on, for example, the input received and/or values calculated at input/output portion 136a. It should be understood that insulin pumps can be implemented in many additional or alternative configurations of partner device 136.

More generally, partner devices 136 may include medical and other devices configured to use analyte data received from analyte sensor system 8 for patient treatment and/or guidance. Partner devices 136 may generally include medicament delivery devices, where the delivery of medicaments to patients is conditioned on, among other factors, characteristics of analyte data received from analyte sensor system 8. One example of partner device 136 is an insulin pump. Another example of partner device 136 is an insulin pen. Partner device 136 may be adapted to run a medicament delivery application using code or instructions stored in a memory or storage of partner device 136, as will be described in more detail herein (e.g., with reference to FIG. 5B).

Partner device 136, such as for example an insulin pump that delivers medicaments to a patient automatically, may impose requirements on the quality and/or nature of the wireless connection/link over which partner device 136 receives analyte data used to make decisions regarding the medicament delivery, as well as on the configuration of the ecosystem in which partner device 136 is being used. Additional types of partner devices 136 may likewise impose similar or other requirements. For example, some partner devices 136 may require a more dedicated, robust connection so that, e.g., the user or patient relying on the pump for insulin delivery does not miss an insulin dose. In such examples, the connection via which the insulin pump receives analyte data should be relatively secure and reliable, and interference from other devices (e.g., display devices 110, 120, 130, 140) should be reduced. As another example, partner devices 136 may have certain constraints on battery life, accuracy with respect to the calculation of CGM data, and so forth. Partner devices 136 may be able to send CGM commands as well as other types of commands to analyte sensor system 8, and also to control the mode of operation of the analyte sensor system 8 according to system requirements 650 of partner device 136, as will be described herein (for example, referencing FIG. 5B).

In example implementations where partner device 136 is an insulin pump, the insulin pump receiving analyte data from analyte sensor system 8 and engaging in automatic insulin delivery may for example seek to prevent other display devices 110, 120, 130, 140 from sending CGM control commands to analyte sensor system 8. Such CGM control commands could affect the algorithm used to calculate CGM data, and as a result affect the amount of insulin delivered by the insulin pump, which may not be desirable/expected. In order to maintain control over the amount of insulin delivered, it may be desirable for the insulin pump to be able to prevent display devices 110, 120, 130, 140 from sending such CGM control commands. This may be done using various techniques described herein.

Other types of partner devices 136, for example, insulin pens, smart fridges, smart mirrors, vehicles, and any other connected device, may impose different or similar requirements, and/or may have more relaxed requirements for wireless communication and other performance aspects. Injection devices such as an insulin pen may receive analyte data from analyte sensor system 8 and use the analyte data to provide an instruction or guidance (e.g., whether graphical, audible, haptic, etc.) to a user that the user should (or should not) administer medicaments (e.g., inject insulin), and may also include a dosage or injection timing suggestion. That is, unlike the insulin pump implementations of partner devices 136, an insulin pen may rely upon user action/intervention. A smart fridge implementation of partner device 136 may connect to analyte sensor system 8, monitor analyte data as well as a user's food/drink consumption, and provide feedback to the user relating to the user's expected or resulting blood glucose levels as related to the food/drink consumption. A smart mirror implementation of partner device 136 may connect to analyte sensor system 8 and/or display device 110, 120, 130, 140 and provide the user with a head-up display of analyte information and/or other guidance cues for diabetes management or other kinds of healthcare suggestions.

As will be appreciated, just as many different types of partner devices 136 are contemplated, there is also a large number of manufacturers that may provide partner devices 136 for operation with analyte sensor system 8 and/or display devices 110, 120, 130, 140. Across the spectrum of device types and manufacturers, etc., there exists a need for flexibility and adaptability in the system so that interoperability, predictability, and expanded use can be maintained and fostered, and so that the interaction and performance of the various devices can be controlled and/or optimized.

Turning now to FIG. 5B, a more detailed example functional block diagram of partner device 315 is provided. It will be appreciated upon studying the present disclosure that with respect to partner device 315, several like components are described with respect to FIGS. 4 and 5 and display device 310 and analyte sensor system 308, at least for some embodiments, and the details and uses of the applicability of such like components will be understood vis-à-vis partner device 315 even if not expressly described with reference to FIG. 5B.

As shown in FIG. 5B, embodiments of partner device 315 may include medicament delivery mechanism 640 that may be used to deliver medicaments (e.g., insulin) to a user, including based on analyte data generated using analyte sensor system 308 and received at partner device 315 via communication media 305. For example, where partner device 315 is an insulin pump, medicament delivery mechanism 640 may in embodiments include an infusion set that can deliver insulin from a cannula or other type of reservoir within or external to partner device 315. Or, for example, where partner device 315 is an insulin pen, medicament delivery mechanism 640 may include a needle that may be used to inject insulin into the user.

Partner device 315 may also include processor/microcontroller 630 that may be coupled to a radio unit or transceiver 610 for sending/receiving sensor data and requests and commands and other signaling to/from an external device, such as display device 310 and/or analyte sensor system 308 and/or another partner device 315. Transceiver 610 may be part of connectivity interface 605 within partner device 315 and may also be used to send medicament-related information, including dosage, bolus information, alerts/alarms/notifications, etc. to analyte sensor system 308, display device 310, other partner devices 315, and/or server system 334 (referencing FIG. 2A).

Partner device 315 may further include storage 615 and real time clock (RTC) 645, for storing and tracking medicament delivery data, sensor data, and/or other information (e.g., command/control signaling, link characteristics, user input, etc.). Storage 615 may store, among other information/items, medicament delivery application 625 and/or other applications, and/or system requirements 650. System requirements 650 of partner device 315 may be imposed to address safety, regulatory, user experience, power consumption, reliability, and/or accuracy requirements on the operation and/or performance of partner device 315, as well as in some cases other requirements that apply to the ecosystem in which partner device 315 is used.

Medicament delivery application 625 may process and/or present analyte, medicament, and/or other data received by or sent from partner device 315 (e.g., received from analyte sensor system 308, display device 310, another partner device 315, and/or server system 334), according to various operations described herein, and may present aspects of some such data via user interface 635. Additionally, application 625 may be used in connection with user interface 635 to obtain, access, display, control, and/or interface with medicament, analyte, and/or other data and related messaging and processes associated with partner device 315, display device 310, analyte sensor system 308, and/or server system 334. For example, user interface 635 may allow a user to enter user or other information into partner device 315 to assist in administering medicaments to the user, to authenticate the user (e.g., by fingerprint, facial, voice, or security code etc.), and/or to enter user preferences or plans for operation of partner device 315 (e.g., planned use or non-use, mode control, etc.), and/or analyte sensor system 308 (e.g., sensor replacement, expected operation time, etc.), and/or display device 310 (e.g., permissions for accessing data from partner device 315). It will also be appreciated that application 625 may run on partner device 315 but may not be user-visible thereon. For example, while application 625 may be used to execute instructions for controlling the operation of partner device 315, a user's interfacing with application 625 may be done via display device 310 (or in some cases not at all).

Application 625 may be downloaded, installed, and initially configured/setup on partner device 315. For example, partner device 315 may obtain application 625 from server system 334, where application 625 may be provided by a manufacturer of partner device 315 in some cases, or from another source accessed via communication media 305, such as an application store or the like. Following installation and setup, application 625 may be used to access and/or interface with partner device 315, including medicament-related data (e.g., whether stored on server system 334, locally from storage 615, or from display device 310 and/or analyte sensor system 308). By way of illustration, application 625 may be used to present a menu (whether on display device 310, analyte sensor system 308, and/or partner device 315) that includes various controls or commands that may be executed in connection with the operating of partner device 315, analyte sensor system 308, and/or one or more display devices 310.

Figure 8:
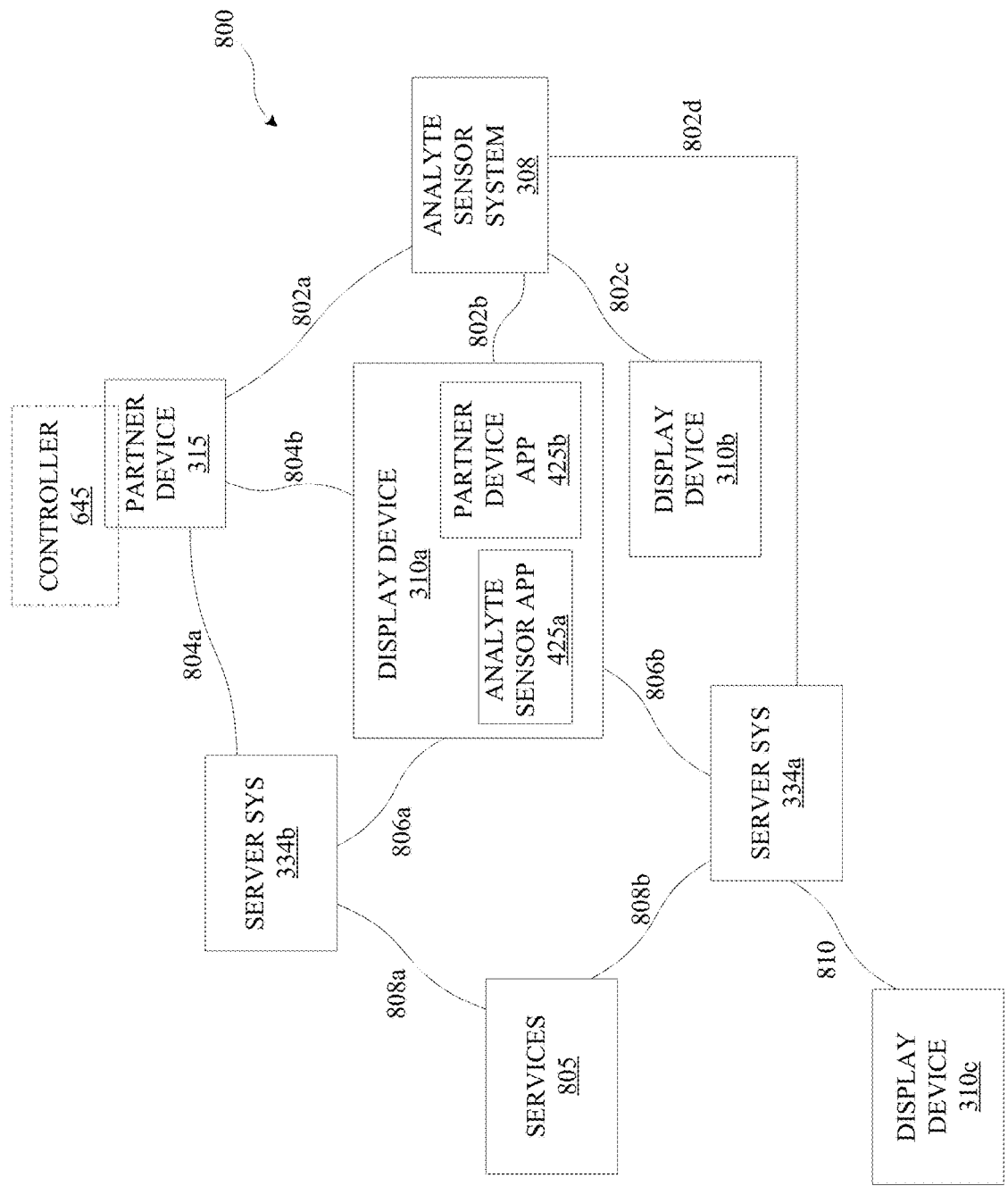
FIG. 8 illustrates aspects of an example system that may be used in connection with implementing embodiments of the disclosure.
Figure 9A:
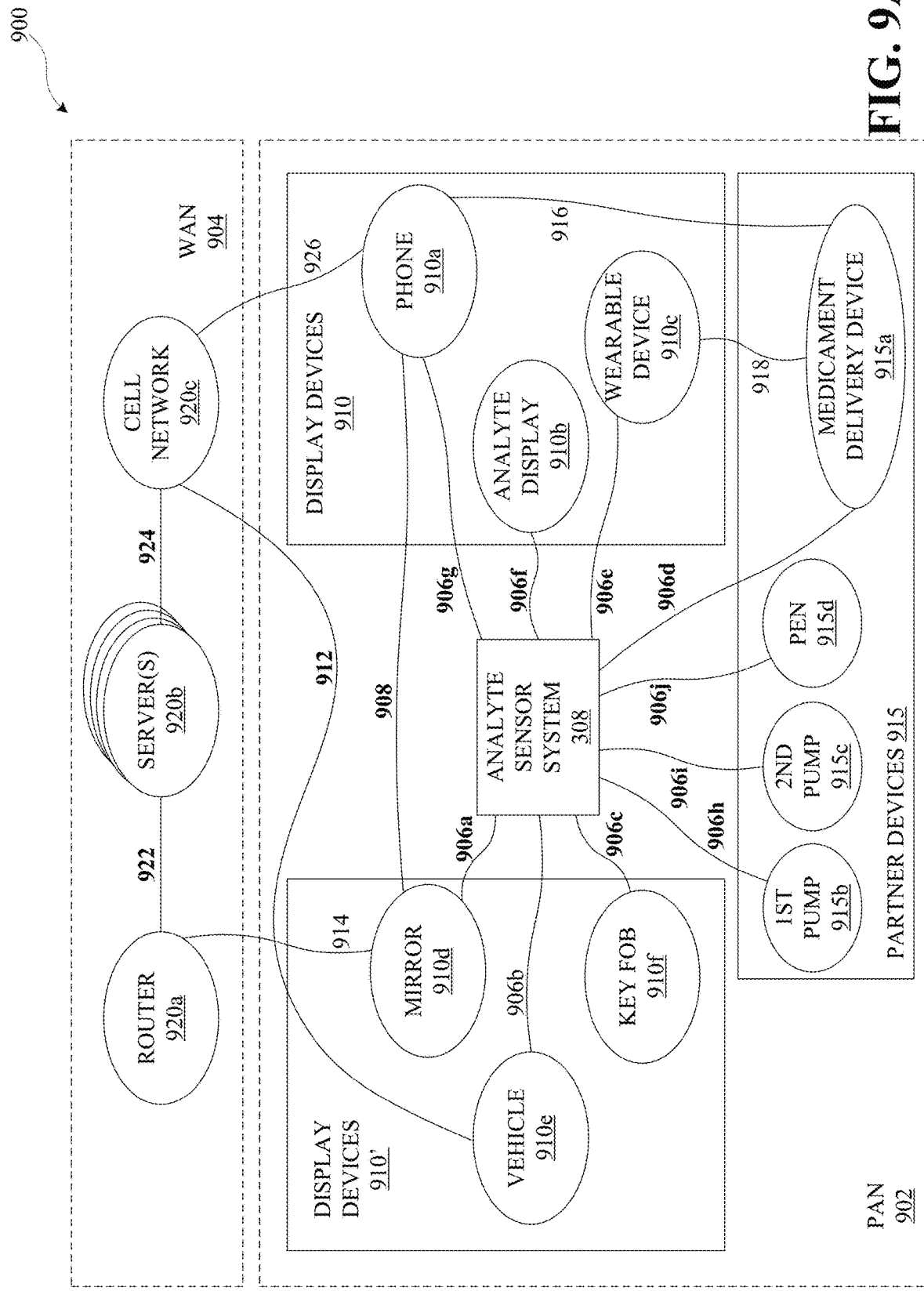
FIG. 9A illustrates aspects of an example system that may be used in connection with implementing embodiments of the disclosure.
Figure 9G:
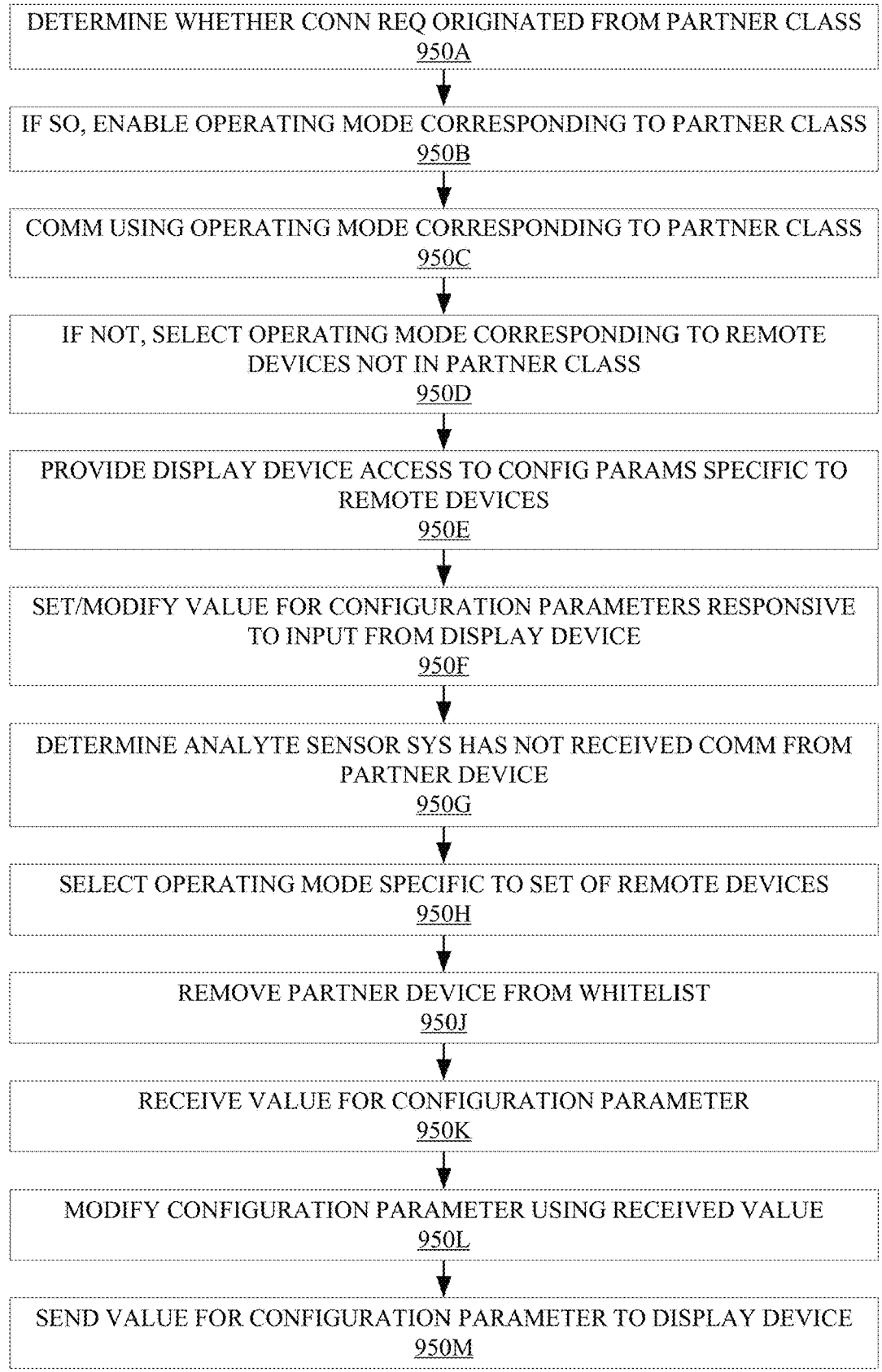
FIG. 9G is an operational flow diagram illustrating various operations that may be performed in accordance with embodiments of the disclosure.
Figure 9H:
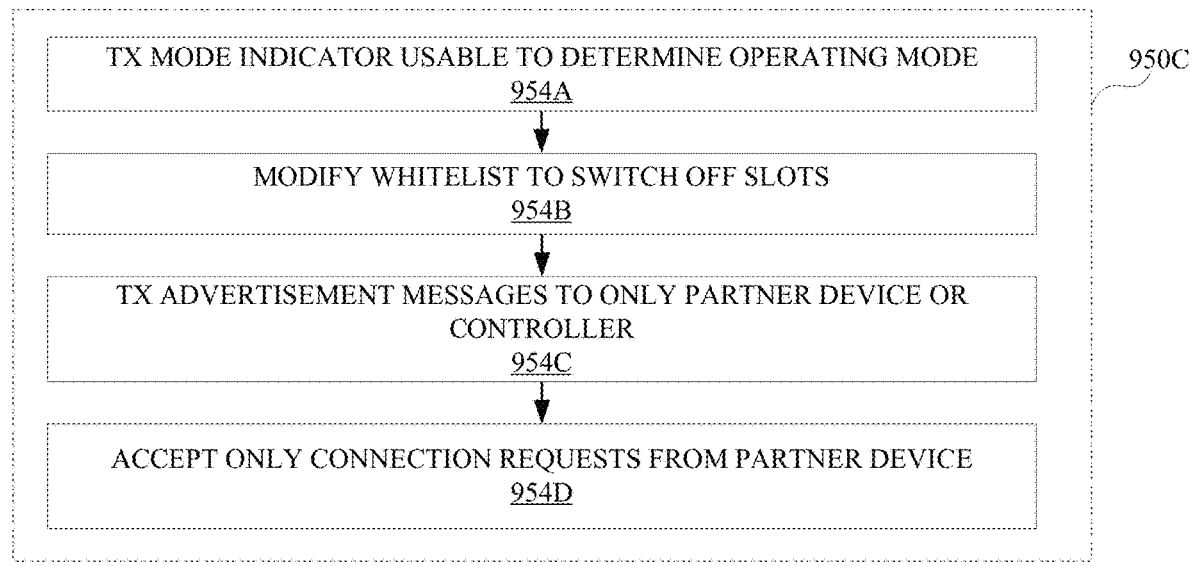
FIG. 9H is an operational flow diagram illustrating various operations that may be performed in accordance with embodiments of the disclosure.
Figure 9J:
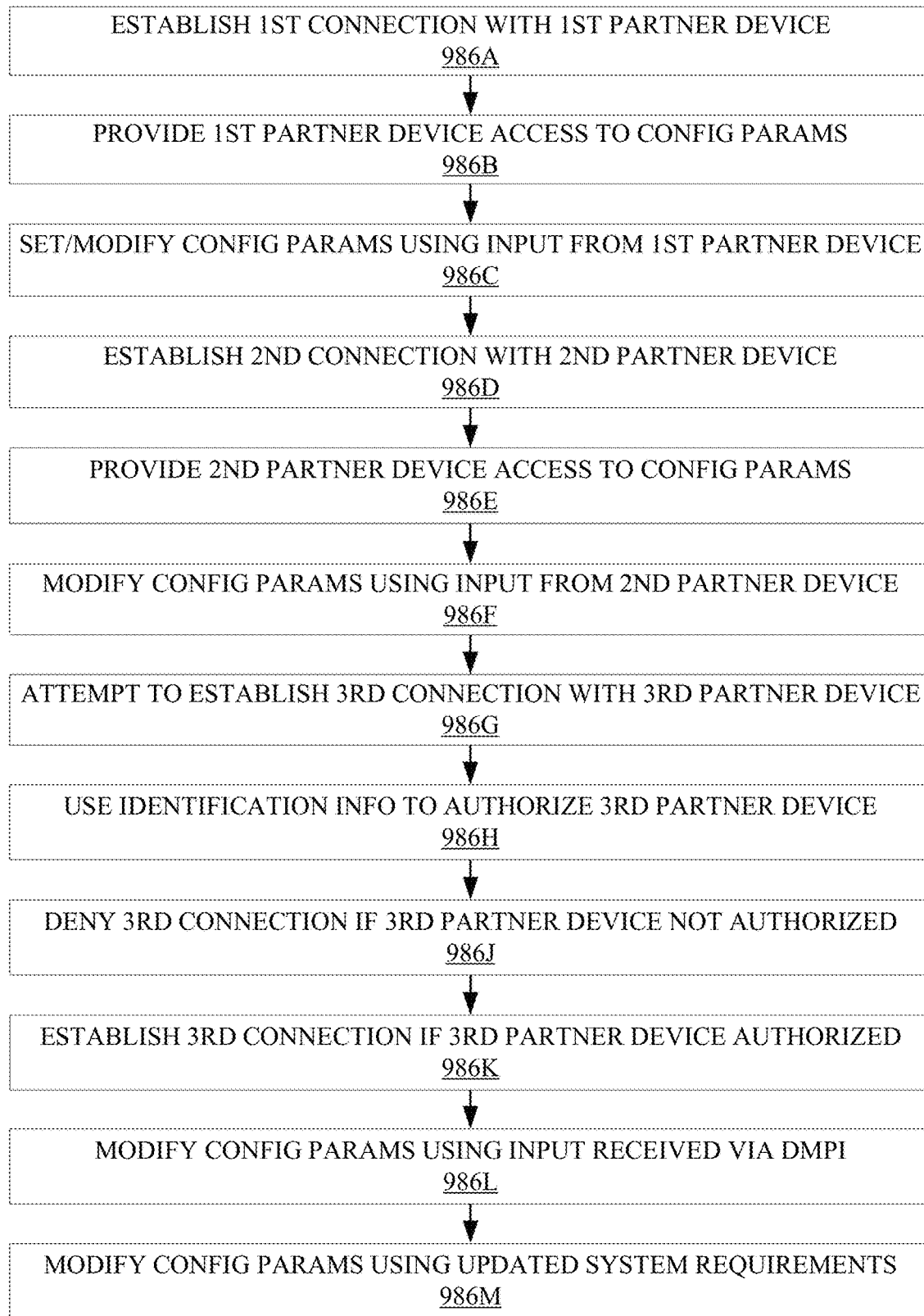
FIG. 9J is an operational flow diagram illustrating various operations that may be performed in accordance with embodiments of the disclosure.
Figure 9K:
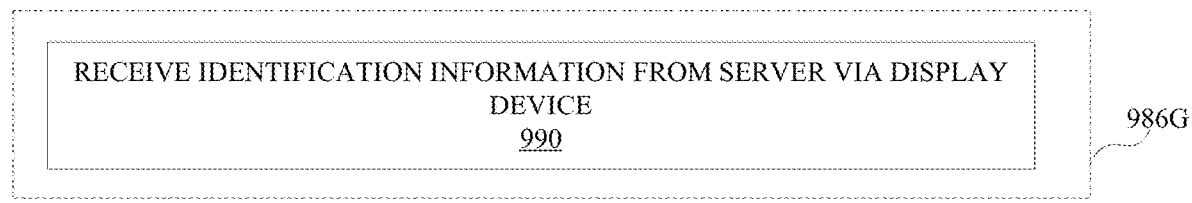
FIG. 9K is an operational flow diagram illustrating various operations that may be performed in accordance with embodiments of the disclosure.
Figure 9L:
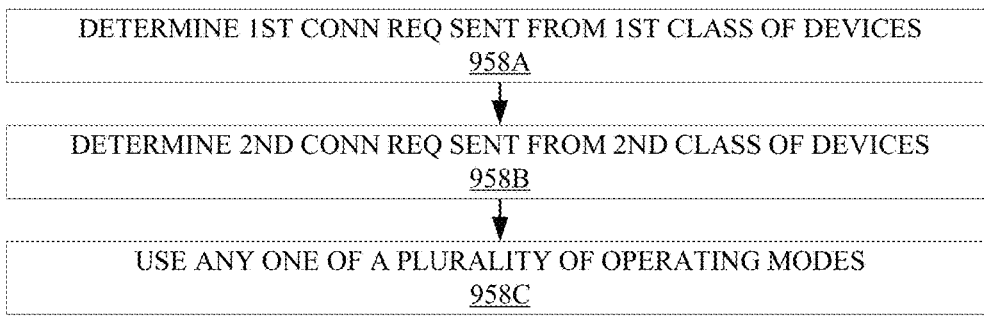
FIG. 9L is an operational flow diagram illustrating various operations that may be performed in accordance with embodiments of the disclosure.
Figure 9M:
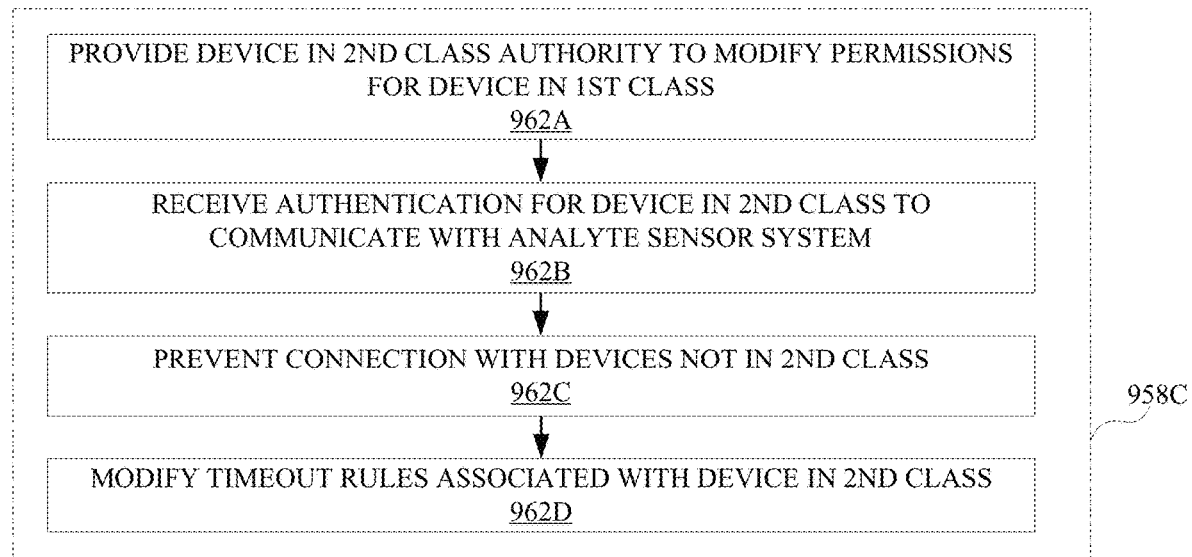
FIG. 9M is an operational flow diagram illustrating various operations that may be performed in accordance with embodiments of the disclosure.
Figure 9N:
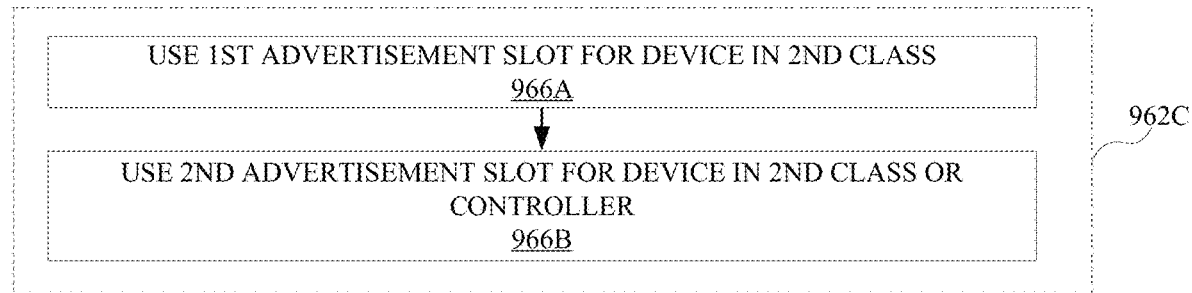
FIG. 9N is an operational flow diagram illustrating various operations that may be performed in accordance with embodiments of the disclosure.
Figure 9P:
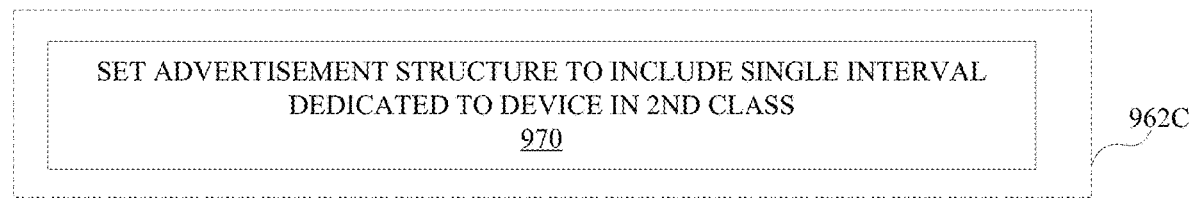
FIG. 9P is an operational flow diagram illustrating various operations that may be performed in accordance with embodiments of the disclosure.
Figure 9Q:
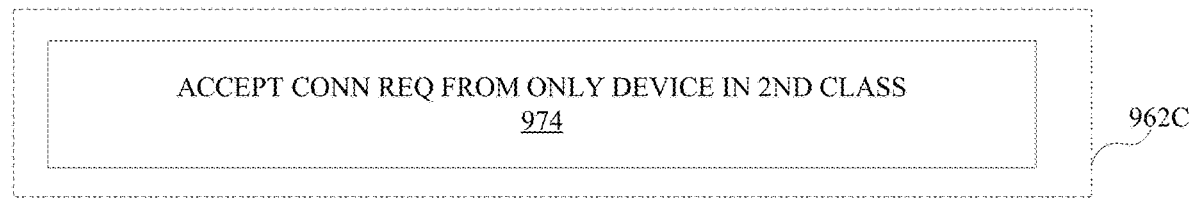
FIG. 9Q is an operational flow diagram illustrating various operations that may be performed in accordance with embodiments of the disclosure.
Figure 9R:
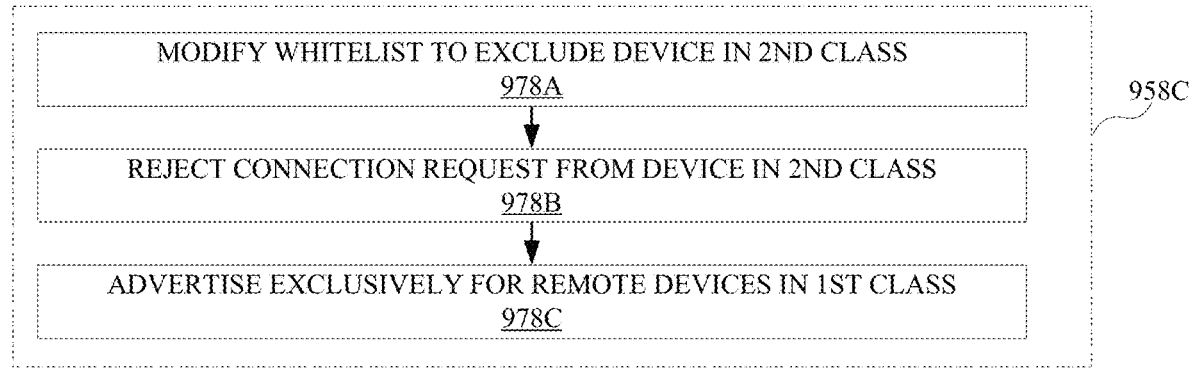
FIG. 9R is an operational flow diagram illustrating various operations that may be performed in accordance with embodiments of the disclosure.
Figure 9S:
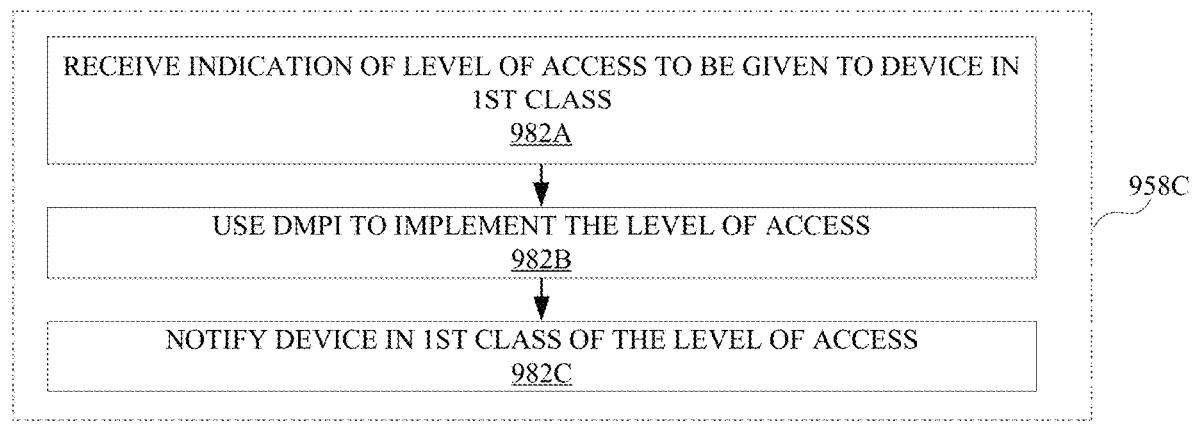
FIG. 9S is an operational flow diagram illustrating various operations that may be performed in accordance with embodiments of the disclosure.

Application 625 may also be used to interface with or control display devices 310, and/or with other partner device 315 vis-à-vis the operation of partner device 315 in the systems/ecosystems described herein, for example, to receive/deliver or make available medicament or data, including for example by receiving medicament-related or analyte-relate data from partner device 315, display device 310, and/or analyte sensor system 308, and/or by sending an instruction for analyte sensor system 308, display device 310, and/or partner device 315 to be connected in a particular manner, mode, etc., as will be described herein (e.g., with reference to FIGS. 8 and 9A-9S). Additionally, application 625 in some implementations may interact with one or more additional applications supported by display device 310, for example to retrieve or supply relevant data. Such applications may include, by way of example, fitness/lifestyle monitoring applications, social media applications, and so on. Such applications may also include applications associated with analyte sensor system 308 and/or display device 310, including analyte sensor application 425a and partner device application 425b.

Medicament delivery application 625 may include various code/functional modules, such as, for example, a medicament delivery module, an authentication module, a system configuration module, and so on as will become clear in light of the description of various functionalities herein (e.g., in connection with disclosed methods). These modules may be implemented separately and/or in combination. Each module may include (non-transitory) computer-readable media and have computer-executable code stored thereon, such that the code may be operatively coupled to and/or executed by processor 630 to perform specific functions with respect to interfacing with partner device 315 and/or medicament-related data, and/or performing tasks related thereto, as well as to interface with other applications/devices (e.g., display device 310, analyte sensor system 308, etc.).

As will be further described below, a display module of display device 310 or of partner device 615 may present (e.g., via a display of user interface 435, with reference to FIG. 4, and/or of user interface 635, with reference to FIG. 5B) various screens to a user, with the screens containing graphical representations of information provided by application 625 (e.g., insulin dosage information). In further embodiments, application 625 may be used to display to the user of display device 310 an environment for viewing and interacting with partner device 315. In embodiments, partner device 315 may include a display as part of user interface 635, in which case application 625 may provide information for display directly on partner device 315 (as opposed to using display device 310). Medicament delivery application 625 may include a native application modified with a software design kit (e.g., depending on the operating system) in order to carry out the functionalities/features described herein. Such software design kits may be provided by the manufacturer of partner device 315, or by other entities.

As shown in FIG. 5B, partner device 315 optionally includes partner device controller 645. Partner device controller 645 may be used in conjunction with partner device 315 to add capabilities thereto. For example, in embodiments, partner device 315 may not be equipped with radio connectivity hardware/software. In such embodiments, partner device controller 645 may be a "bolt-on" piece of hardware that can couple to partner device 315 via connectivity interface 605 and augment the operational capability of partner device 315, for example by providing or adding a transceiver, memory, and/or processing capabilities (including, e.g., software code/instructions supporting the same). Thus, in example implementations, partner device controller 645 may include a BLE or other radio for communicatively coupling partner device 315 to analyte sensor system 308 and/or display device 310. In embodiments, medicament delivery application 625 may reside at least partially on partner device controller 645. In embodiments, user interface 635 may reside at least partially on partner device controller 645. For example, if partner device lacks a user interface such as a display, partner device controller may be used to add display capabilities to partner device 315.

It should be noted at this juncture that like-named elements as between display device 310, analyte sensor system 308, and/or partner device 315 as described in FIGS. 3C, 4, 5A, may in some cases include similar features, structures, and/or capabilities. Therefore, with respect to such elements, the description of such elements with reference to any one of display device 310, analyte sensor system 308, and partner device 315 above may in some cases be applied to the corresponding or analogous element within any one of display device 310, analyte sensor system 308, and partner device 315.

F. Advertising Timing and Structure

An additional aspect of the present disclosure involves the order and manner in which various devices (e.g., display devices 310 and partner devices 315) connect to analyte sensor system 308, which can depend upon the order, timing, structure, and manner of advertisement messages transmitted to such display devices 310 and/or partner devices 315. One potential scheme for the ordering of connection for various devices may be described as follows.

In embodiments, analyte sensor system 308 advertises to and establishes connections with display devices 310 and/or partner devices 315 that are available for connection (e.g., that are in-range and/or otherwise available). This may be done, for example, by transmitting advertisement messages. By way of example, reference is made to operation 1005a shown in FIG. 7A. On the display device 310/partner device 315 side, display devices 310 and/or partner devices 315 seeking a connection with analyte sensor system 308 may in example embodiments scan for analyte sensor system 308 or another like sensor system to enter into a connection therewith. This generally entails receiving and processing advertisement messages that are being broadcast by analyte sensor system 308 etc., in order to determine whether any such messages are being transmitted by a compatible/desirable analyte sensor system 308.

Display device 310 and/or partner device 315 may then respond to the advertisement message by sending a connection request back to analyte sensor system 308. By way of example, reference is made to operation 1005b shown in FIG. 7A. Upon receiving the connection request, analyte sensor system 308 may accept, deny, or simply ignore the request. In example implementations, analyte sensor system 308 serves only one display device 310 or partner device 315 connection at a time. Therefore, one ground for denying or ignoring a connection request is that analyte sensor system 308 is already connected to a display device 310 or a partner device 315. If there are no grounds for denying or ignoring a connection request, analyte sensor system 308 may accept the request and connect to the display device 310 or partner device 310 that sent the request. For example, operation 1005b shows analyte sensor system 308 accepting the request by sending signaling to display device 310 or partner device 315 to indicate that the connection request is granted. Aspects of advertisement and related contexts are also illustrated by way of example with reference to FIGS. 6, 7A-7C. (See, e.g., operations 1065a, 1095a.) Detailed discussions of these FIGS. are included further below.

Figure 7A:
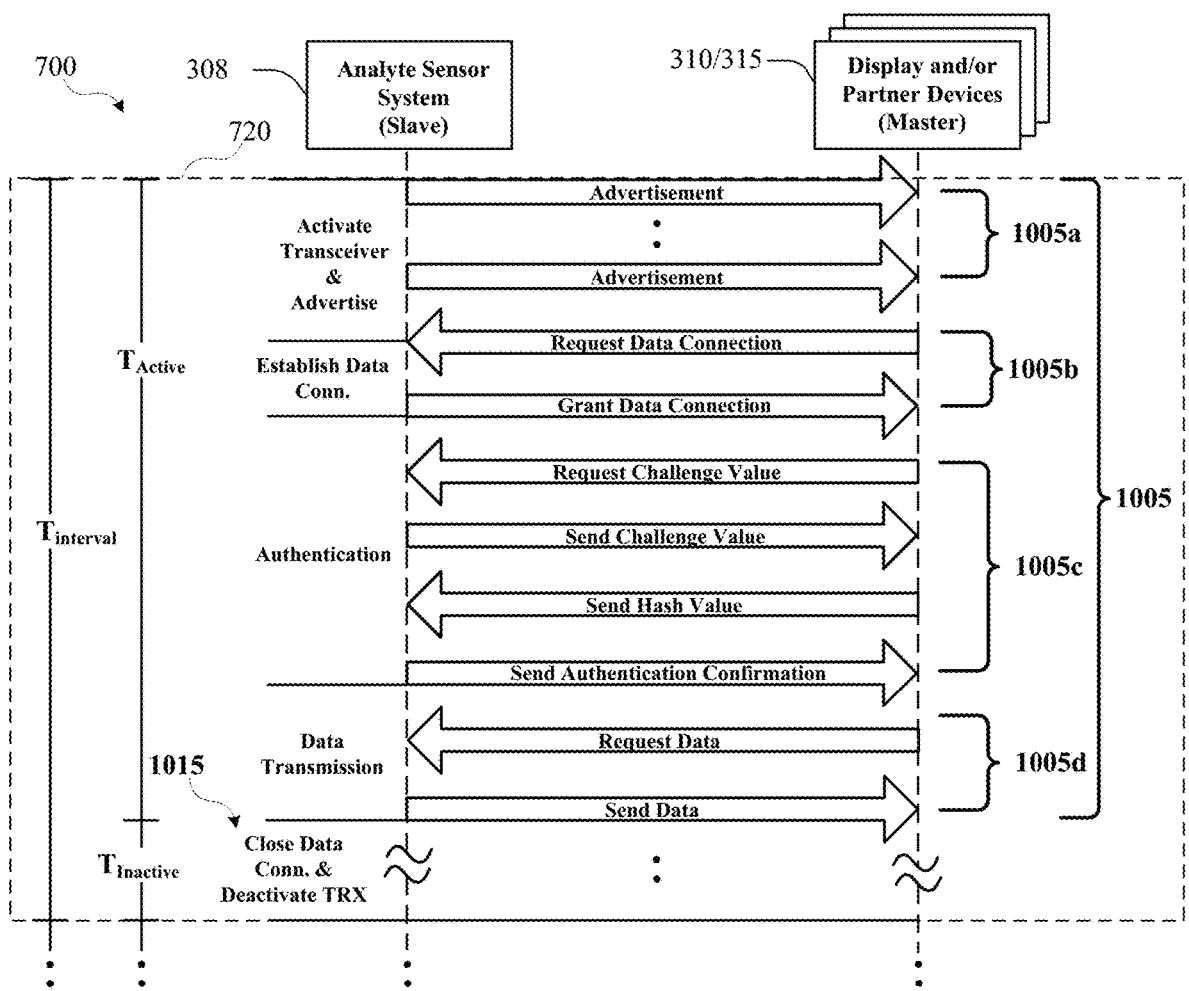
FIG. 7A is an operational flow diagram illustrating various operations that may be performed in accordance with embodiments of the disclosure.

Referring further to FIG. 7A, once display device 310 (or partner device 315) and analyte sensor system 308 are connected, messaging may be exchanged, including for example, analyte sensor system 308 transmitting analyte data to display device 310 or partner device 315. By way of example, reference is made to operation 1005d shown in FIG. 7A. In embodiments, in order to prevent display device 310 or partner device 315 from staying connected to analyte sensor system 308 longer than is expected or desired, analyte sensor system 308 may enforce timeouts, and/or may cause timeouts to be enforced. That is, for example, there may be a predetermined limit set with respect to the duration of the connection, and upon the expiry of the same, the connection to analyte sensor system 308 may be terminated. By way of example, reference is made to operation 1015 shown in FIG. 7A, at which a data connection is closed and, optionally, transceiver 410 is deactivated. Terminating the connection may allow a connection or at least a connection attempt to be made vis-à-vis analyte sensor system 308 and other display devices 310 and/or partner devices 315. Analyte sensor system 308 may maintain a list of display devices 310 and/or partner devices 315 that have recently connected to analyte sensor system 308. In some cases, this may be known as a whitelist. Analyte sensor system 308 may use this list to permit only listed display devices 310 and/or partner devices 315 (i.e., that have recently connected, or that are otherwise listed) to connect to analyte sensor system 308.

Figure 6:
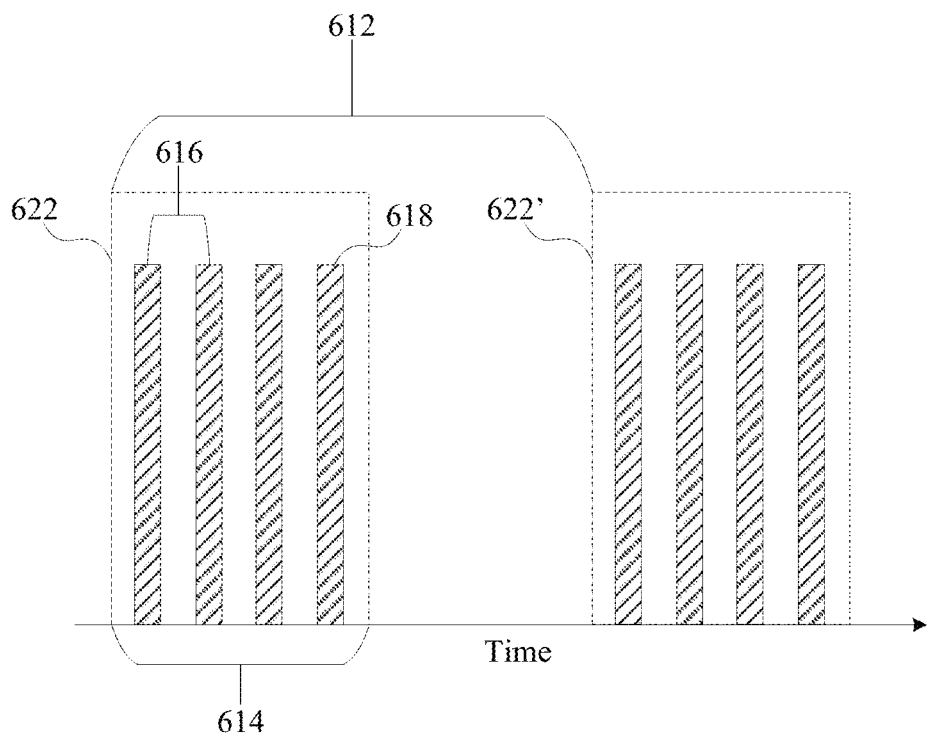
FIG. 6 is a timing diagram illustrating aspects of advertisement messages that may be transmitted in accordance with embodiments of the present disclosure.

FIG. 6 is a timing diagram illustrating an example of the transmission of advertisement messages in accordance with embodiments of the present disclosure. More specifically, FIG. 6 provides an example of advertisement duration structure 622 that may be used in connection with pairing or establishing a connection among/between analyte sensor system 308, display devices 310, and/or partner devices 315. In connection with the above and in accordance with embodiments of advertisement duration structure 622, advertisement messages 618 may be sent according to a time interval that occurs periodically based on a schedule. This may be referred to herein in some cases as an advertisement window interval 612. The period of repetition of the occurrence of advertisement window interval 612 may be any length of time.

In embodiments, advertisement window interval 612 may be configured or set to vary depending upon the nature of the operation of analyte sensor system 308 with respect to gathering and processing analyte data and/or depending upon the nature of operation of partner device 315 vis-à-vis the administration of medicaments, and/or based on other considerations. In example implementations, advertisement window interval 612 may be configured or set to vary based upon whether partner device 315 is connectable to analyte display device 308. In example implementations, advertisement window interval 612 may be configured or set to vary based upon system requirements 650 of partner device 315. In example implementations, advertisement window interval 612 may be configured or set to vary based upon the network topology of a system wherein analyte sensor system 308 is in communication with one or more of partner devices 315, display devices 310, and server system 334 (e.g., system 200, with reference to FIG. 2A, system 800, with reference to FIG. 8, and/or system 900, with reference to FIG. 9A). For example, advertisement window interval 1012 may be configured or set to vary based upon a number of display devices 310 connectable to analyte sensor system 308, based upon whether partner device 315 is an automatic insulin delivery device, and/or based upon system requirements 650 of a partner device 315 that is an automatic insulin delivery device. In one specific example, advertisement window interval 612 is approximately 5 minutes. Thus, in this specific example, every 5 minutes, there will be a time window for advertisement messages 618 to be transmitted.

The time window for advertisement messages 618 may be considered a duration of time during which advertisement messages 618 may actually be transmitted. This may also be referred to in some cases as advertisement duration 614. By way of example, in some example implementations, advertisement duration 614 may range from 7 to 22 seconds in length. It will be appreciated by one of ordinary skill in the art upon studying the present disclosure, however, that the length of advertisement duration 614 (in time) may range from 0 to any reasonable amount of time. In some cases, advertisement duration 1014 is shorter than advertisement window interval 612. This may change, however, based upon system configurations/requirements discussed in detail elsewhere herein.

During advertisement duration 614, advertisement messages 618 may be transmitted, in some cases periodically, though not necessarily so, according to advertisement message interval 616. Advertisement message interval 616 may be thought of as a time interval between sequential or successive transmissions of advertisement messages 618. One specific example range for advertisement message interval 616 is between 20 and 90 msec, though it will be appreciated upon studying the present disclosure that advertisement message interval 616 may be shorter or longer, and/or may be adaptively variable, programmable, and/or configurable in length, depending on the relevant circumstances, including adapting or (re)configuring advertisement message interval 616 during advertisement duration 614.

In embodiments, advertisement message interval 616 may be configured or set to vary depending upon the nature of the operation of analyte sensor system 308 with respect to gathering and processing analyte data and/or depending upon the nature of operation of partner device 315 vis-à-vis the administration of medicaments, and/or based on other considerations. In example implementations, advertisement message interval 616 may be configured or set to vary based upon whether partner device 315 is connectable to analyte display device 308. In example implementations, advertisement message interval 616 may be configured or set to vary based upon system requirements 650 of partner device 315. In example implementations, advertisement message interval 616 may be configured or set to vary based upon the network topology of a system wherein analyte sensor system 308 is in communication with one or more of partner devices 315, display devices 310, and server system 334 (e.g., system 200, with reference to FIG. 2A, system 800, with reference to FIG. 8, and/or system 900, with reference to FIG. 9A). For example, advertisement window interval 612 may be configured or set to vary based upon a number of display devices 310 connectable to analyte sensor system 308, based upon whether partner device 315 is an automatic insulin delivery device, and/or based upon system requirements 650 of a partner device 315 that is an automatic insulin delivery device.

After advertisement window interval 612 has elapsed, advertisement messages 1018 may resume transmission, and advertisement duration structure 622 may be repeated (e.g., as advertisement duration structure 622'). It should also be noted that one or more of the advertisement message interval 616, advertisement duration 1014, and advertisement window interval 612 can be reconfigured as between advertisement duration structures 622 and 622' and/or within the respective advertisement durations of advertisement duration structures 622, 622' (e.g., 614, etc.).

The above-mentioned features of advertisement duration structure 622, including advertisement window interval 612, advertisement duration 614, and advertisement message interval 616, can each vary based on a variety of factors. For example, the values of these parameters may vary based on the type and/or number of display devices 310 present, as well as based on the system requirements of such display devices 310, and/or on how recently such display devices 310 have connected to analyte sensor system 308. As another example, the values of these parameters may vary based on the type and/or number of partner devices 315 present, as well as based on system requirements 650 and/or other characteristics of such partner devices 315 (e.g., whether automatic insulin delivery is being provided). The values of these parameters can also vary in order to optimize connection reliability, accuracy, battery life, to speed up connection time, etc. of display device 310 and/or partner device 315. Any one of a decreased advertisement window interval 612, an increased advertisement duration 614, and a decreased advertisement message interval 616, may increase the likelihood that a connection can be successfully established as between a particular display device 310 and/or partner device 315, and analyte sensor system 308 or other device. In examples, however, there may be a concomitant increase in power consumption with changing the parameters in this manner.

It should also be appreciated that one or more advertisement durations 614 may be specifically allocated to a particular display device 310 or partner device 315 for connection. Accordingly, by revoking the allocation of advertisement durations 614 from specific devices, or by not allocating advertisement durations 614 to such devices in the first place, it is possible to prevent a connection from being established as between such devices and analyte sensor system 308. This may be done where, for example, a dedicated connection is desired between partner device 315 and analyte sensor system 308, where such dedicated connection may be substantially free from potential interference introduced by devices other than partner 315 responding to advertisements send by analyte sensor system 308.

Accordingly, aspects of the present disclosure include configuring advertisement duration structure 622, including configuring advertisement window interval 612, advertisement duration 1014, and/or advertisement message interval 616, and other features associated with advertisement messaging and/or related thereto. Aspects of the present disclosure also include controlling the allocation of advertisement durations 614 to specific devices (e.g., display device 310 and/or partner device 315), in order to create dedicated advertisement slots for such specific devices.

The foregoing aspects of the present disclosure may be used to increase the likelihood of successfully establishing a connecting with analyte sensor system 308. In addition, configuring advertisement duration 612 and/or controlling the allocation of advertisement durations 614 may also reduce power consumption involved with connection establishment, due to increased efficiency of the connection protocol. In this manner, the overall reliability of communications related to analyte data and/or medicament delivery can be increased, while the power consumption can be decreased. In embodiments, the above-described aspects of advertisement messaging can be configured to effect intelligent tradeoffs among reliability, speed, power consumption/efficiency, and so forth, including where such tradeoffs may be implemented dynamically based on, for example, system requirements 650 of partner devices 315 that may be unknown prior to partner devices 315 attempting to establish connections with analyte sensor system 308.

It should also be appreciated here that with respect to the above features of connection establishment and/or advertisement messaging, in addition to analyte sensor system 308 transmitting advertisement messages to display devices 310 and/or partner devices 315 for connection establishment purposes, display devices 310 and/or partner devices 315 may send advertisement messages for connection establishment purposes as well. In such instances, it will be understood upon studying the present disclosure that the above features may be similarly employed.

G. Connection Models

As alluded to above, aspects of the present disclosure also include various connection models for communications between or among analyte sensor system 308, display devices 310, server system 334, and/or partner device 315. One connection model for communications may be referred to as an intermittent connection model (or in some cases a connect/disconnect model). In accordance with an intermittent connection model, communications between/among analyte sensor system 308, display device 310, server system 334, and/or partner device 315 may be periodic or intermittent in nature, following a defined or event-based/asynchronous schedule. For example, display device 310 and/or partner device 315 may establish connection with analyte sensor system 308 periodically (e.g., once every five minutes) in order to exchange analyte and/or other data with analyte sensor system 308.

In example implementations, rather than having the transmission and receiving circuitry of analyte sensor system 308, display device 310, and/or partner device 315 continuously communicating, analyte sensor system 308, display device 310, and/or partner device 315 may intermittently, regularly, and/or periodically establish a communication channel between/among them. Thus, for example, analyte sensor system 308 can in some cases communicate via wireless transmission with display device 310 and/or partner device 315 at predetermined time intervals. The duration of the predetermined time interval can be selected to be long enough so that analyte sensor system 308 does not consume too much power by transmitting data more frequently than needed, yet frequent enough to provide substantially real-time sensor information (e.g., measured glucose values or analyte data) to display device 310 for output (e.g., via a display as part of user interface 435) to a user and/or to partner device 315 for example for use in the administration of medicaments. While the predetermined time interval may be for example every five minutes in some embodiments, it should be appreciated that this time interval can be varied to be any desired length of time (e.g., as discussed above in connection with FIG. 6).

In embodiments, the intermittent connection model may result in power savings relative to other connection models. Accordingly, if battery power is a primary concern relative to packet loss and/or latency etc., then the intermittent connection model may be preferable to the continuous connection model. Additionally, it will be appreciated that according to the intermittent connection model, display devices 310 and/or partner devices 315 in example implementations are not connected to analyte sensor system 308 at the same time. Rather, different display devices 310 and/or partner devices 315 in some cases connect for different, limited amounts of time. Which display devices 310 and/or partner device 315 may connect and when such devices can connect to analyte sensor system 308 may be controlled, for example, using a list such as a whitelist and/or by modifying the advertising structure employed, as described above with reference to FIG. 6. Accordingly, in some situations, the intermittent model may be suitable and/or preferable. One such situation may be if a user prefers to monitor an analyte value using multiple display devices 310. For example, if the user has Type 1 diabetes, monitoring of analyte (e.g., glucose) data may be relatively more critical, and hence, multiple display devices 310 may be employed for greater coverage/redundancy.

FIG. 7A is an operational flow diagram illustrating various operations that may be performed in connection with embodiments of method 700 for wireless communication of analyte data between/among analyte sensor system 308, display device 310, server system 334, and/or partner device 315, according to the intermittent connection model described above. Features of method 700 can also be applied in connection with embodiments of related systems, apparatuses, and devices. More specifically, as shown in FIG. 7A, communication session 720 may involve operations 1005a through 1015, though in embodiments, not all of these operations are necessarily performed.

The various tasks performed in connection with the procedure illustrated in FIG. 7A may be performed, for example, by processors 430, 530, and/or 630 executing instructions embodied respectively in storage 415, 515, and/or 615 (which may include, e.g., non-transitory computer-readable media). The tasks or operations performed in connection with the procedure may be performed by hardware, software, firmware, and/or any combination thereof incorporated into one or more computing devices, such as one or more of analyte sensor system 308, display device 310, server system 334, and/or partner device 315.

It will be appreciated upon studying the present disclosure that the procedure may include any number of additional or alternative tasks or operations. This is generally but not necessarily always true for all the procedures and/or methods described herein. The operations shown by way of example in FIG. 7A need not necessarily be performed in the illustrated order, and the procedure may be incorporated into a more comprehensive procedure or process having additional functionality not described in detail herein with specific reference to FIG. 7A. Again, this is generally but not necessarily always true for all the procedures and/or methods described herein.

In some examples described below, the analyte values are glucose values based on one or more measurements made by analyte sensor system 308 and/or sensor 535 (with reference to FIG. 3C). Nevertheless, it should be understood upon studying the present disclosure that in embodiments the analyte values can be any other analyte value described herein or known in the art. The wireless data communication between analyte sensor system 308, display devices 310, server system 334, and/or partner devices 315 may happen periodically, at times separated by an update interval denoted "T interval" that may correspond to a time duration between consecutive wireless communication sessions between the transceiver 510 of analyte sensor system 308 (referencing FIG. 3C), transceiver 410 of display device 310 (referencing FIG. 4), and/or transceiver 610 of partner device (referencing FIG. 5B). Alternatively or additionally, the update interval may be thought of as a period of obtaining and sending a recently measured or generated glucose value, medicament-related, or other data. Transmitting advertisement signals or messages, establishing a data connection (e.g., a communication channel) and requesting and sending data may occur during wireless communication sessions each lasting an active time or period denoted "$T_{Active}$" within an update interval $T_{interval}$. One caveat here is that $T_{interval}$ and/or $T_{Active}$ can vary as between sessions. In between consecutive wireless communication sessions, components of analyte sensor system 308 (e.g., transceiver 510), of display device 310 (e.g., transceiver 410), and/or of partner device 315 (e.g., transceiver 610) may enter a low power mode or a like mode, such as an inactive or sleep mode, for an inactive period denoted as "$T_{Inactive}$". This may enable the conservation of battery life and/or reduce peak voltage requirements, for example.

Accordingly, in some connection schemes used for the communication of analyte data, medicament data, and/or other data and control signaling, a connection may be periodically established between/among analyte sensor system 308, display device 310, server system 334, and/or partner device 315. For example, with further reference to FIG. 7A, communication session 720 may implement one such connection scheme (that optionally includes authentication). More specifically, communication session 720 may be implemented during a time interval $T_{interval}$. As alluded to above, $T_{interval}$ may include an active portion corresponding to $T_{Active}$ and an inactive portion corresponding to $T_{Inactive}$. Generally speaking, during $T_{Active}$, analyte sensor system 308 and display device 310 and/or partner device 315 are connected and actively exchanging messaging (e.g., pursuant to operation 1005 and/or sub-operations thereof), though there may be periods during $T_{Active}$ during which analyte sensor system 308, display device 310, and/or partner device 315 enters a low power mode or the like, as described above.

In terms of connecting, in example implementations, analyte sensor system 308 may transmit one or more advertisement messages at operation 1005 during communication session 720. An advertisement message may be considered as an invitation for display device 310 and/or partner device 315 to establish a data connection with analyte sensor system 308 (e.g., via transceiver 510). Example structures for advertisement messages that in some cases may be transmitted for purposes of establishing a connection between two devices, according to various aspects of the present disclosure are above in connection with FIG. 6, and in U.S. Provisional Application Nos. 62/364,771 and 62/409,677, which are incorporated herein by reference in their entireties. The transmitted advertisement messages may then be received at display devices 310 (e.g., via transceiver 410) and/or partner devices 315 (e.g., via transceiver 610).

As alluded to above, during communication session 720, an authentication procedure may optionally be performed in connection with a data connection process corresponding to operation 1005b and/or a data transmission process corresponding to operation 1005d. To establish a data connection with analyte sensor system 308, display device 310 and/or partner device 315 may listen or scan until an advertisement message transmitted by analyte sensor system 308 is received. Accordingly, operation 1005b may involve analyte sensor system 308 receiving a connection request from display device 310 and/or partner device 315 and responding thereto by granting or denying the request. If analyte sensor system 308 grants the connection request, an acknowledgement or other message may be transmitted to display device 310 and/or partner device 315 as part of operation 1005b. Then, a data connection between analyte sensor system 308 and display device 310 and/or partner device 315 may be established.

According to operation 1005c, an authentication procedure may be employed before data is actually exchanged at operation 1005d. Authentication may involve the exchange of various messages, including challenge and hash values and signaling related thereto, between analyte sensor system 308 and display device 310 and/or partner device 315, in accordance with a one-way or two-way handshake process per operation 1005c. Once authenticated, analyte sensor system 308 and display device 310 and/or partner device 315 may exchange information to determine how data will be exchanged (e.g., a specific frequency, time slot assignment, encryption, etc.). Further, communication session 720 may also include exchanging an application key between analyte sensor system 308 and display device 310 and/or partner device 315. By the exchange of challenge and hash values described in connection with operation 1005c, such an application key may effectively be shared between analyte sensor system 308 and display device 310 and/or partner device 315. Thus, in embodiments, the application key may be used for both authentication and encryption purposes.

With further reference to FIG. 7A, after completion of the optional authentication process according to operation 1005c, analyte sensor system 308 and connected display device 310 and/or partner device 315 may engage in data communication at operation 1005d, during which connected display device 310 and/or partner device 315 may request and receive desired information (e.g., analyte data, control information, identification information, and/or instruction) from analyte sensor system 308 and/or may send information including command and control signaling or other information, such as for example medicament-related information. When data communication at operation 1005d is completed, the data connection may be terminated at operation 1015 (e.g., by closing the established communication channel).

In other circumstances, however, a continuous connection model may be suitable and/or preferable relative to the intermittent connection model described above. At a high level, the continuous connection model can involve an initial pairing between analyte sensor system 308 and display device 310 and/or partner device 315, after which analyte sensor system 308 and display device 310 and/or partner device 315 remain connected, essentially not closing the connection or disconnecting. That is, connection and the exchange of data in example implementations is not done periodically or intermittently as with the intermittent connection model (e.g., as discussed with reference to FIG. 7A), but instead, the connected devices periodically exchange messaging to maintain the connection. Once data is available at analyte sensor system 308, the data can be transmitted to display device 310 and/or partner device 315 in near or at least near real time. In this manner, the overall accuracy and responsiveness of communications related to analyte data may be increased. An additional advantage associated with the continuous connection model is that analyte sensor system 308 may be enabled to better mitigate against interferences caused by undesired devices (e.g., in some cases, undesired display devices 310) seeking to connect with analyte sensor system 308. Hence, reliability of data exchange and robustness of connection may be increased, which may be particularly important where a user is relying upon partner device 315 for the administration of medicaments such as insulin.

By way of example, the potential increase in reliability of data exchange may be beneficial, for example, where partner device 315 is an insulin pump used to automatically deliver insulin to a user based on analyte data generated using analyte sensor system 308 and transmitted to partner device 315. In some such cases, connection reliability/robustness between analyte sensor system 308 and partner device 315 may be more critical relative to the ability to establish connections with multiple display devices 310, and as mentioned above, connection requests from display devices 310 may cause interference with a connection, or the establishment of a connection, between partner device 315 and analyte sensor system 308. The continuous connection model as employed, for example, between analyte sensor system 308 and partner device 315 may serve as a means for increasing connection reliability/robustness and may thus be preferable for certain embodiments involving partner device 315, as well as in other situations described and/or alluded to herein.

Accordingly, embodiments of the present disclosure include employing a continuous connection model between certain devices. Such a connection model may in some cases reduce latency between the collection and/or generation of analyte data at analyte sensor system 308 and the transmission of such data and related data and control signaling to display devices 310 and/or partner devices 315 connecting thereto, as well as exchange of medicament-related data and control signaling, while maintaining a sufficiently low power consumption for analyte sensor system 308. Furthermore, as mentioned above, the continuous connection model may increase reliability/robustness and predictability of the connection between analyte sensor system 308 and display device 310 and/or partner device 315.

Figure 7B:
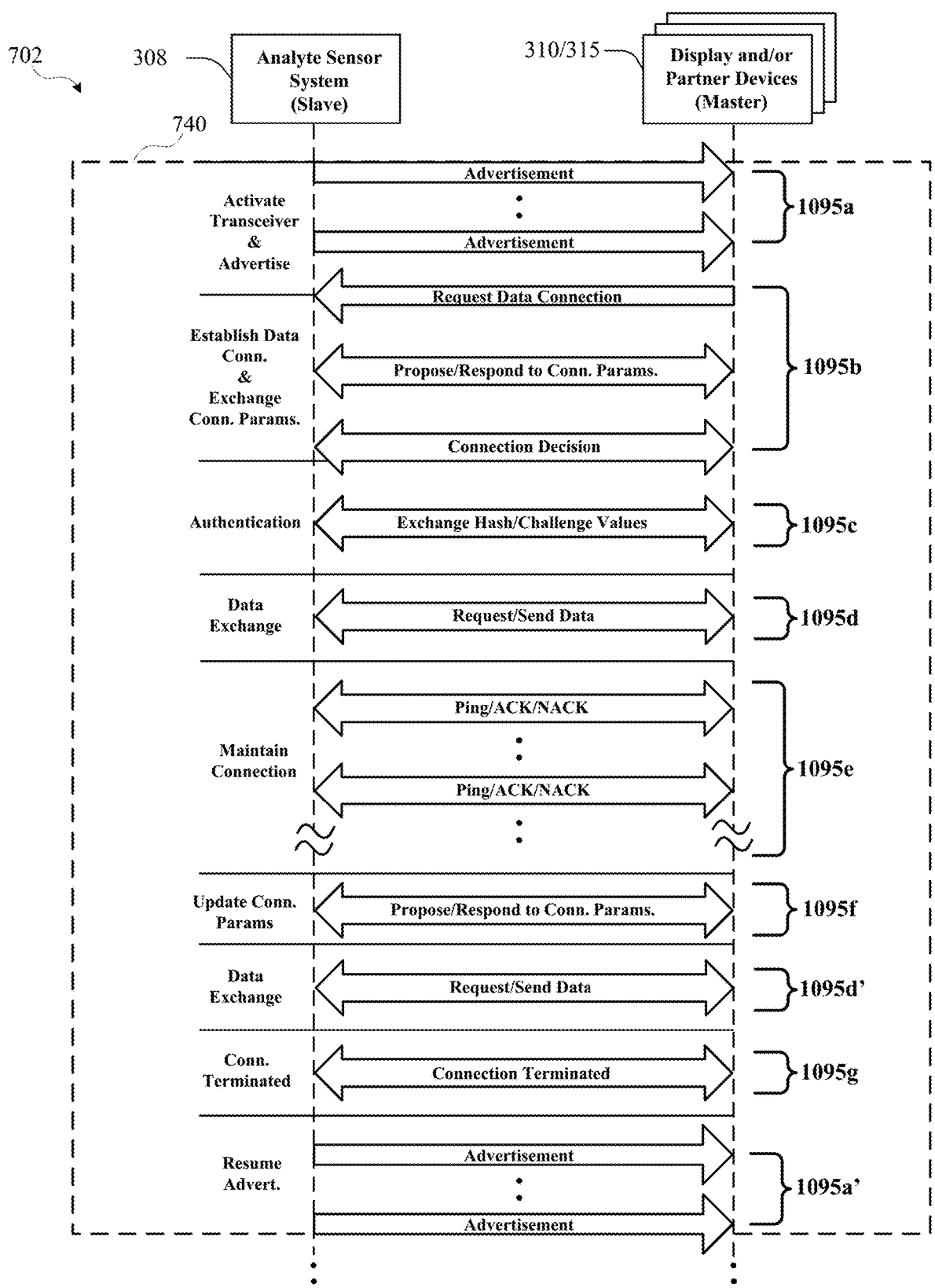
FIG. 7B is an operational flow diagram illustrating various operations that may be performed in accordance with embodiments of the disclosure.

In this connection, FIG. 7B illustrates example implementations of method 702 for wireless communication of analyte data among/between analyte sensor system 308 and display device 310 and/or partner device 315 according to example implementations of the continuous connection model alluded to above. Communication session 740 can be initiated in connection with method 702. More specifically, as shown in FIG. 7B, communication session 740 may involve operations 1095a through 1095g and/or 1095a', though in embodiments, not all of these operations are necessarily performed.

As with FIG. 7A, the various tasks performed in connection with the procedure illustrated in FIG. 7B may be performed, for example, by processors 430, 530, and/or 630 executing instructions embodied respectively in storage 415, 515, and/or 615 (which may include, e.g., non-transitory computer-readable media). The tasks or operations performed in connection with the procedure, an in general but not necessarily always in connection with all procedures, operations, and methods described herein, may be performed by hardware, software, firmware, and/or any combination thereof incorporated into one or more computing devices, such as one or more of analyte sensor system 308, display device 310, server system 334, and/or partner device 315. It will be appreciated upon studying the present disclosure that the procedure may include any number of additional or alternative tasks or operations. The operations shown by way of example in FIG. 7B need not necessarily be performed in the illustrated order, and the procedure may be incorporated into a more comprehensive procedure or process having additional functionality not described in detail herein with specific reference to FIG. 7B.

With respect to the continuous connection model, analyte data may be dropped or lost if the connection between/among analyte sensor system 308 and display device 310 and/or partner device 315 is not maintained. This may in turn lead to improper or inaccurate representation of analyte information, such as estimated glucose values, and in some cases, may lead to administration of medicaments that is not as accurate or precise as desired. Thus, embodiments herein related to the continuous connection model involve sustaining and/or maintaining a connection established between/among analyte sensor system 308 and display device 310 and/or partner device 315. Further, with respect to maintaining the connection, it may at times be useful to monitor the connection status to derive and/or provide an indication regarding the same. One way this may be done is using connection parameters.

At operation 1095a, method 702 may involve activating a transmitter of analyte sensor system 308 and/or transmitting advertisement messages. This transmission of advertisement messages may be substantially similar to operation 1005a described above. The advertisement messages transmitted at operation 1095a may be received by one or more display devices 310 and/or partner devices 315, for example.

At operation 1095b, a connection may be established between analyte sensor system 308 and display device 310 and/or partner device 315 responding to the advertisement messages. As part of operation 1095b, connection parameters can be exchanged between analyte sensor system 308 and display device 310 and/or partner device 315. In this regard, analyte sensor system 308, display device 310, and/or partner device 315 may propose and set up a set of connection parameters upon which aspects of a connection with analyte sensor system 308 may be based.

Examples of connection parameters include a connection interval (in some cases referred to herein as a pinging interval), slave latency, and supervision timeout. Analyte sensor system 308 and/or display device 310 and/or partner device 315 can use one or more of such connection parameters to maintain a connection continuously exchanging data, for example related to analyte levels, medicament delivery, related control signaling, system configuration signaling, etc. Additional connection parameters may relate to control signaling, such as mode control for display devices 310 and/or partner devices 315, and/or control signaling related to network topologies that may be implemented in accordance with embodiments described herein.

Following a connection decision that results in establishing a connection, at operation 1095c, method 702 may optionally involve authentication. At operation 1095d, embodiments of method 702 include exchanging data between/among analyte sensor system 308, display device 310, and/or partner device 315. With respect to the continuous connection model, operation 1095d may be repeated periodically, as data becomes available for transmission (e.g., in some cases aperiodically), and/or whenever data is requested to be exchanged (e.g., on-demand). The exchange of data according to operation 1095d may be interspersed with the exchange of other messaging, such as, for example, ping messaging or other control-related messaging exchanged with analyte sensor system 308. In FIG. 7B, this may be represented by way of example using the operations intervening operation 1095d and 1095d' (i.e., operations 1095e and 10950, though certain types of control signaling may not be explicitly illustrated.

In embodiments, connection parameters agreed upon in conjunction with connection establishment (e.g., as part of operation 1095b), as well as other configuration aspects, can be updated/modified subsequently, for example, after a connection decision is made. Accordingly, at operation 1095f, method 702 may involve updating one or more of the connection parameters. As shown at operation 1095g, in some cases, the connection with analyte sensor system 308 may be terminated or lost. There may be various causes for this. In response to connection being lost at operation 1095g, analyte sensor system 308 may send advertisement messages according to operation 1095a'. In accordance with example embodiments of the continuous connection model, upon analyte sensor system 308 and display device 310 and/or partner device 315 becoming disconnected, analyte sensor system 308 may resume sending advertisement messages in some cases at least almost immediately.

A user of display device 310 and/or partner device 315 may not be aware that there has been a disconnection according to operation 1095g. This may in some cases lead to packet drop or data loss. Thus, in some cases, analyte sensor system 308 may resume advertisement automatically without user intervention. Alternatively or in addition, the user may receive a notification via analyte sensor system 308, display device 310, and/or partner device 315 that the connection has been lost.

Figure 7C:
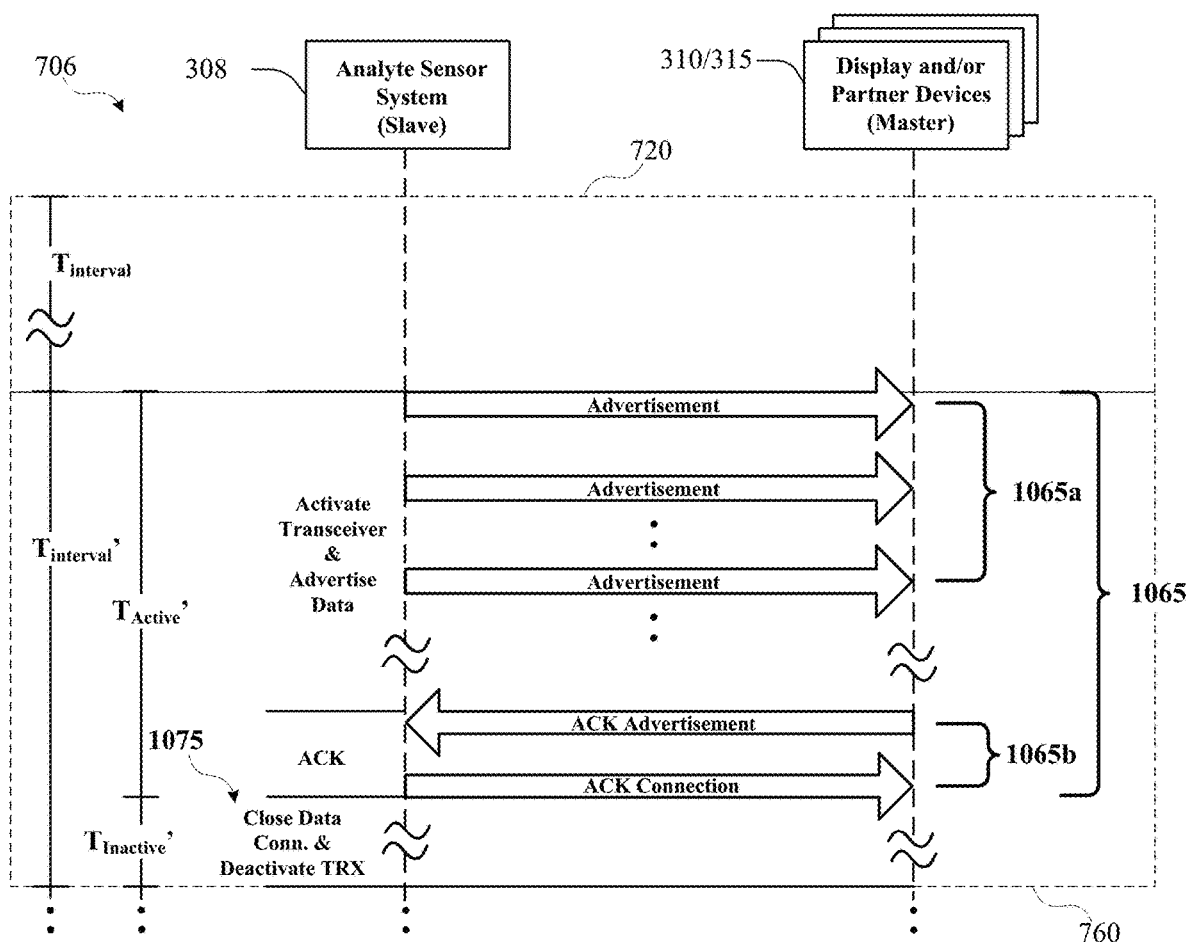
FIG. 7C is an operational flow diagram illustrating various operations that may be performed in accordance with embodiments of the disclosure.

FIG. 7C shows that, in addition to the intermittent connection model and the continuous connection model, embodiments of the present disclosure also involve communications of data through broadcasting of packets, where no connection establishment as such is necessary. The broadcast of data packets, as will be described more fully herein, can be particularly useful where certain devices connectable to analyte sensor system 308, e.g., display devices 310, are set in a display only state while another connectable device(s), e.g., partner device 315, is has established a connection to and is exchanging data and command/control messaging with analyte sensor system 308.

In FIG. 7C, method 706 for wireless communication of analyte-related data, medicament-related data, and/or other information between/among analyte sensor system 308, display device 310, and/or partner device 315 is illustrated in connection with implementations of the present disclosure. Example embodiments of method 706 involve establishing a first connection between, for example, analyte sensor system 308 and display device 310 and/or partner device 315. This is optional and may occur in connection with communication session 720 corresponding to $T_{interval}$. As such, establishing the first connection can optionally include authentication between analyte sensor system 308 and display device 310 and/or partner device 315.

Method 706 also includes establishing communication session 760 that may be implemented during a time interval $T_{interval}'$, which may be the same as or different from $T_{interval}$. $T_{interval}'$ may include an active portion corresponding to $T_{Active}'$ and an inactive portion corresponding to $T_{Inactive}'$. During $T_{Active}'$, communication session 760 may involve operation 1065 and sub-operations thereof.

Here it should be noted that, as mentioned above, communication session 760 may not include establishment of a connection between/among analyte sensor system 308, display device 310, and/or partner device. For example, communication session 760 as illustrated does not include the data connection aspects of operation 1005b shown in FIG. 7A in connection with communication session 720. Nor does communication session 760 as illustrated include the authentication process that may be included in communication session 720 (e.g., at operation 1005c). Rather, at operation 1065a, method 706 involves sending one or more advertisement messages to display device 310 and/or partner device 315.

As such, as part of communication session 760, analyte sensor system 308 may transmit a first advertisement message (e.g., operation 1065a). The first advertisement message may include at least a first portion of an analyte value. The analyte value may but need not have been encrypted (e.g., using an application key) prior to transmission. In other words, with regard to communication session 760, analyte sensor system 308 may use one or more advertisement messages to transmit encrypted or non-encrypted analyte values or analyte data and/or other signaling (such as, e.g., timing and control information) in addition to other information that may be included in advertisement messages.

In some cases, an advertisement message may take the form of a packet. By way of example, the analyte value (whether encrypted or not) may be included in a reserved or other field in the advertisement message packet, and/or may be encoded into the packet. The advertisement message may also or additionally include other information, such as for example a time stamp associated with the analyte value. In example implementations, method 706 may involve breaking the payload, which may include the (encrypted) analyte value and associated data, into multiple parts. The first advertisement message may then indicate that a second advertisement message includes a second portion of the analyte value and/or associated data. The first advertisement may so indicate by tagging the first portion of the payload, where the tag represents that a subsequent advertisement message may include a second portion of the payload.

In other words, according to communication session 760, advertisement messages may be transmitted in connection with operation 1065a for the purposes of communicating analyte and/or other data to display devices 310 and/or partner devices 315. With the payload encrypted using an application key, privacy/security can be maintained even in the absence of authentication procedures being performed during communication session 760. Likewise, because the payload is included in the advertisement messages, the data connection request and data transmission processes (e.g., operations 1005b and 1005d, respectively, with reference to FIG. 7A) can also be bypassed or avoided. In this manner, the number of messages exchanged in pursuant to communication session 760 (and hence the power consumption) may be reduced relative to other communication sessions. Additionally, for example, analyte and other data may be provided to display devices 310 even while partner device 315 maintains a dedicated connection to analyte sensor system 308 and acts as the only device with permission to send command and control signaling to analyte sensor system 308 (e.g., calibration commands related to a sensor session).

With further reference to FIG. 7C, communication session 760 may also include, at operation 1065b, display device 310 and/or partner device 315 acknowledging receipt of the advertisement message(s) sent during operation 1065a, by sending an acknowledgement (ACK) message. In some cases, this acknowledgement may trigger a data connection process between analyte sensor system 308 and the acknowledging display device 310 and/or partner device 315. For example, analyte sensor system 308 may in turn send an ACK to display device 310 and/or partner device 315 and thus establish a connection therewith. This data connection process, in example deployments, may be used for renewing the application and/or encryption key(s) and/or for exchanging other data, such as, for example, calibration data, timing information, exchange of permissions, mode control signaling, and the like. When communications at operation 1065 are completed, data transmission may be terminated at operation 1075. At this point, transceiver 510 and/or processor 530 of analyte sensor system 308 can be deactivated. In FIG. 7C, this generally corresponds to operation 1075 and is denoted as $T_{Inactive}'$.

As mentioned above, there may be various tradeoffs as between the intermittent connection model and the continuous connection model. For example, battery power may in some cases be more rapidly consumed if the continuous connection model is employed, though reliability/robustness may in some cases be increased. Thus, it may be preferable in some cases to switch to the intermittent connection model. In another example, due to multiple connection requests/ acknowledgments, operating in the intermittent connection model may lead to an increased chance of dropped/lost data. Thus, it may be preferable in some cases to switch to the continuous connection model. In additional examples, the control/command signaling permissions for a particular device may be changed, for example due to network topology and/or operating mode changes, and in such cases the connection model may be changed (including, e.g., to from the advertisement broadcast scheme described with reference to FIG. 7C).

Accordingly, embodiments of the present disclosure involve switching between these connection models in order to provide a flexible and adaptable system that may be optimized for a variety of uses, operating conditions, and user/system preferences. Switching adaptively (whether in an automated fashion or based on user input, both of which are contemplated herein) may allow for optimization of battery power usage as well as transmission efficiency and data accuracy and connection reliability/robustness. In addition, device performance and behavior can, in accordance with example embodiments, be tracked over time and be used to develop an optimization profile with respect to circumstances in which various connection models may be preferable.

In some cases, the connection model may be switched on an automated basis depending on various criteria. For example, the connection model may be set depending upon the type of display device 310 and/or partner device 315 being connected to analyte sensor system 308. For example, the connection model may be set based on the number of display devices 310 being used—e.g., if a single, dedicated device is being used (e.g., for a predetermined amount of time), then the system may switch to the continuous connection model. Or, if many display devices 310 are being used, a number of the display devices 310 may utilize communication session 740. In another example, the connection model may be switched based upon current or projected battery life of analyte sensor system 308, display device 310, and/or partner device 315. The quality of exchanged signals may also be used to determine whether a switch between connection models is appropriate. Further, a switch in connection models may be based on the time of day and/or the location of analyte sensor system 308, partner device 315, and/or display device 310. The switch could be initiated by display device 310, partner device 315, and/or analyte sensor system 308 (e.g., using mode control signaling).

In embodiments, the switch may be based on user input or may be semi-automatic. For example, a user may navigate a GUI provided by user interface 435 of display device 310 to implement the switch. In another example, the switch may be triggered automatically or without user intervention (e.g., by or in response to partner device 315), in turn triggering a prompt being presented to the user on display device 310 via the GUI of user interface 435. The user may then approve or deny the switch (thus, the switch can be made semi-automatic). The prompt may provide the user with information regarding the connection model currently employed, the reason for the proposed switch, and in some cases the consequences of rejecting and/or accepting the proposed switch, including tradeoffs related to the same. In other examples, no prompt may be provided to the user.

Figure 7D:
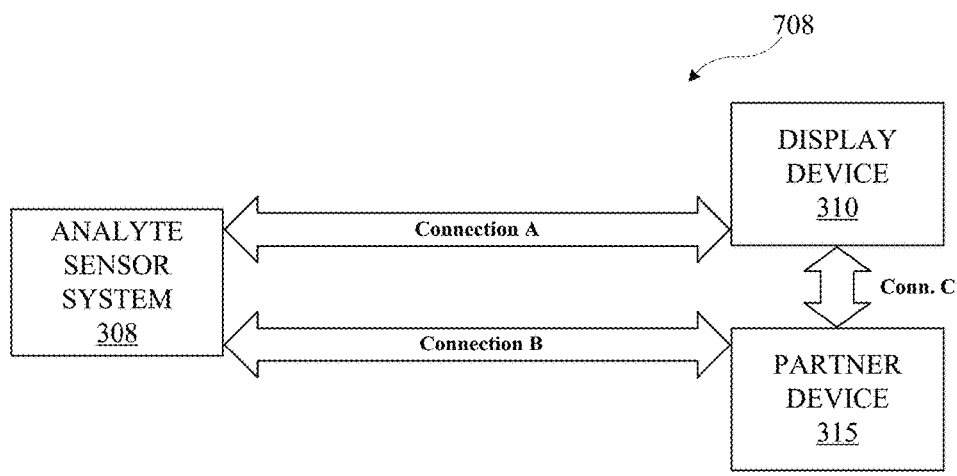
FIG. 7D illustrates aspects of an example system that may be used in connection with implementing embodiments of the disclosure.

Turning now to FIG. 7D, embodiments of the present disclosure involve configuring and/or setting up a kind of mesh network using various of the connection models described herein (e.g., with reference to FIGS. 7A-7C). For example, display devices 310 and/or partner device 315 (and/or a plurality of either device) can be in connection with analyte sensor system 308 using different connection models. With reference to FIG. 7D and the illustrated example of system 304, analyte sensor system 308 may be connectable to display device 310 and/or partner device 315 via communication media 305 (referencing FIG. 2B). Further, display device 310 and partner device 315 may be connectable to one another via communication media 305 (again referencing FIG. 2B). It will be appreciated that although reference is made here to communication media 305, additional communication media and/or links may be included in the mesh-like networks described herein, and/or using various connection models (e.g., communication media 305a, 305b, etc., referencing FIG. 2B).

Referring again to FIG. 7D, for example, communication session 740 can be employed as between analyte sensor system 308 and partner device 315, while at the same time a different communication session (e.g., 720, 760, etc.) can be employed as between display devices 310, on the one hand, and analyte sensor system 308 on the other hand. Further still, yet another communication session can be employed between display devices 310 and partner devices 315. FIG. 7D shows that in connection with system 304, analyte sensor system 308 may be connectable to display device 310 and/or partner device 315 using various communication media (e.g., communication media 305) and/or connection models (e.g., intermittent connection model, continuous connection model, etc., as discussed in further detail with reference to FIGS. 7A-7C), represented by way of illustration as Connections A and B. Additionally, display device 310 and partner device 315 may be connectable to one another using various communication media 305 and/or connection models, represented by way of illustration here as Connection C. Certain details of the continuous connection and intermitted connection models are discussed in further detail in U.S. Provisional Application Nos. 62/364,771 and 62/409,677, both of which are incorporated herein by reference in the their entirety.

For example, when display device 310 and partner device 315 are in range and connectable to analyte sensor system 308, analyte sensor system 308 and display device 310 may connect using the intermittent connection model (e.g., Connection A), and partner device 315 may connect to analyte sensor system 308 using the continuous connection model (e.g., Connection B). Under the intermittent connection model, by way of example, display device 310 periodically connects with analyte sensor system 308, exchanges data therewith, and then disconnects. Under the continuous connection model, by way of example, partner device 315 and analyte sensor system 308 establish a connection and then continuously exchange signaling to maintain that connection while data is exchanged. By way of further example, with the intermittent connection model, there may be a chance that between subsequent periodic connections, other devices connect to analyte sensor system 308 or attempt to do so simultaneously with display device 310, such that display device 310 may be unsuccessful in reconnecting with analyte sensor system 308 (a variety of other circumstances may lead to this as well). By contrast, under the continuous connection model, typically barring a severe event, the connection between partner device 315 and analyte sensor system 308 is more likely to be maintained and not interrupted. In this manner, partner device 315 may maintain a more reliable, prioritized connection with analyte sensor system 308 and may have a better quality of services as a result. As such, for example patient-critical applications such as the automated delivery of insulin by partner device 315, it may be the case that the continuous connection model is preferred as between partner device 315 and analyte sensor system 308.

With further reference to FIG. 7D, partner device 315 and display device 310 may maintain communication via Connection C, using any of the connection models described herein. Thus, partner device 315 can directly share medicament delivery data and other information with display device 310. It will further be appreciated here that the respective connection models used by display device 310 and partner device 315 to connect to analyte sensor system 308 may switch. It will also be appreciated that both display device 310 and partner device 315 can connect to analyte sensor system 308 using the intermittent connection model or the continuous connection model. It should also be appreciated and will be discussed herein that in embodiments, that one or more of analyte sensor system 308, display device 310, and partner device 315 may use the advertisement broadcast connection scheme of communication session 760 for any of Connection A, B, and/or C in system 304.

Regardless of the connection models employed between analyte sensor system 308, on the one hand, and display device 310 and/or partner device 315 on the other hand, display device 310 and partner device 315 may connect to one another using any of the intermittent connection model, the continuous connection model, and/or the advertisement broadcast connection scheme of communication session 760 (referencing FIG. 7C). Furthermore, any of the communication media and/or connection models employed (e.g., in Connections A, B, and C) can switch to a different connection model subsequent to connection establishment, including in a subsequent communication session.

H. Overview of Alerts

In certain embodiments, one or more alerts, alarms, and/or notifications (in some cases, simply "alerts") are associated with analyte sensor system 308, display device 310, and/or partner device 315. For example, alerts may involve one or more alert conditions that indicate when the respective alert has been triggered. Alerts may be triggered based on characteristics of analyte data generated using analyte sensor system 308. For example, a hypoglycemic alert may include alert conditions indicating a minimum glucose level. The alert conditions may also be based on transformed sensor data, such as trending data, and/or sensor data from multiple different sensors (e.g., an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In embodiments, alerts may be triggered based on events or conditions monitored or detected at partner device 315. For example, an alert may be triggered if it is determined (e.g., based on self-diagnostics) that partner device has a mechanical or other failure. In example implementations where partner device 315 is an insulin pump, an alert may be triggered based on a pump fault such as an occlusion. In embodiments, alerts may be triggered if partner device 315 has not delivered insulin to a user or has not done so according to calculated dosages (e.g., based on analyte data).

In certain embodiments, each of the alerts is associated with one or more actions that are to be performed in response to triggering of the alert. Alert actions may include, for example, activating an alarm via a user interface of analyte sensor system 308, such as displaying information on a display of analyte sensor system 308 or activating an audible or vibratory alarm of analyte sensor system 308. In embodiments, alert actions include transmitting data to one or more display devices 310 and/or partner device 315 such that the alert may be provided via user interface 435 and/or 635 (with reference to FIGS. 4 and 5B). For any alert action that is associated with a triggered alert, one or more delivery options may define the content and/or format of the data to be transmitted, the device to which the data can be transmitted, when the data can be transmitted, and/or a communication protocol that may be used for delivery of the data. For example, the propagation of alerts may be prioritized to partner device 315. In embodiments, however, users may be inundated by alerts due to the number of connected devices that may be employed in connection with the gathering and use of analyte data. In such cases, it may be useful to coordinate alerts and notifications across a user's devices, for example, in according to an escalation scheme that may be predefined, adaptable based on the network topology, and/or based on user preferences.

In certain embodiments, multiple alert actions (each having respective delivery options) may be associated with a single alert such that displayable sensor information or other alert information having different content and formatting, for example, can be transmitted to respective display devices 310 and/or partner devices 315 or other devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module of analyte sensor system 308 in response to triggering of a common alert. Advantageously, the sensor electronics module need not be tied to a single display device 310, but rather can be configured to communicate with a plurality of different display devices 310 directly, systematically, simultaneously (e.g., via broadcasting), regularly, periodically, randomly, on-demand, in response to a query, based on alerts or alarms, and/or the like.

In embodiments, analyte sensor system 308 is configured to provide one or a plurality of different alarms directly and/or via transmission of a data package indicating an alarm should be initiated by one or a plurality of display devices 310 (e.g., sequentially and/or simultaneously). In certain embodiments, analyte sensor system 308 merely provides a data field indicating that an alarm condition exists, and display device 310, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, analyte sensor system 308 can perform multiple actions, such as activating an alarm on the sensor electronics module, transmitting a data package to a monitoring device indicating activation of an alarm on the display, and transmitting a data package as a text message to a care provider.

In embodiments, analyte sensor system 308 is configured to wait a time period for the host to respond to a triggered alert (e.g., by pressing or selecting a snooze and/or off function and/or button on analyte sensor system 308 and/or display device 310), after which additional alerts can be triggered (e.g., in an escalating manner) until one or more alerts are responded to. In embodiments, analyte sensor system can be configured to send control signals (e.g., a stop signal) to partner device 315 associated with an alarm condition (e.g., hypoglycemia), such as an insulin pump, wherein the stop alert triggers a stop of insulin delivery via the pump. Although reference is made above to analyte sensor system being configured to provide and/or trigger alerts, it should be appreciated that display device 310 and/or partner device 315 may additionally or alternatively provide and/or trigger alerts.

I. Connectivity Integration of Partner Devices

FIG. 8 depicts system 800 that, for example, may be used in connection with wireless analyte (e.g., glucose) monitoring, and in some instances for diabetes management, including for example the provision of medicaments. System 800 may involve various components interconnected via one or more wired and/or wireless connections for the communication and exchange of information such as analyte data, medicament delivery data, diabetes management feedback and related guidance and services, alerts/notifications, control signaling, and other information.

As illustrated by way of example in FIGS. 8, embodiments of system 800 include one or more of analyte sensor system 308; display devices 310*a*, 310*b*, and/or 310*c*; partner device 315; server systems 334*a* and/or 334*b*; and services 805 that may be provided via server systems 334*a* and/or 334*b*. Here it should be noted that in embodiments, server system 334*b* may be associated with partner device 315, and/or may be maintained by a manufacturer or provider of partner device 315, and server system 334*a* may be associated with analyte sensor system 308, and/or may be maintained by the manufacturer or provider of analyte sensor system 308. Additionally, and embodiments services 805 may be split into separate services respectively supported, maintained, facilitated, and/or provided by manufacturers/providers of an analyte sensor system 308, on the one hand, and partner device 315, on the other hand. Thus, both or either of server systems 334*a* and 334*b* may provide a gateway for receiving services 805 (e.g., backend cloud services). For services 805 supported on behalf of the manufacturer of partner device 315 only (e.g., in some cases, insulin pump related information, alerts, malfunction support, etc.), such services 805 may be provided via server system 334*b*. For services 805 supported on behalf of the manufacturer of analyte sensor system 308 only (e.g., in some cases, providing the ability for another individual/entity to monitor analyte data for a user of display device 310), such services 805 may be provided via server system 334*a* in this example. In embodiments, services 805 may utilize both server systems 334*a* and 334*b* (e.g., in some cases, providing the ability for another individual/entity to monitor analyte data and insulin administration data for a user of display device 310 and partner device 315). Additional aspects of remote services that may be provided via cloud servers, for example server systems 334*a*/334*b*, are discussed below.

Certain of the foregoing components and features of the same shown in FIG. 8 have largely been described above with reference to, e.g., FIGS. 1, 2A, 2B, 3A-C, 4, 5A, 5B, 6, and 7A-D. The components system 800 can be interconnected by various links 802*a-d*, 804*a-b*, 806*a-b*, 808*a-b*, and 810, as shown in FIG. 8, where these links can each respectively be implemented using communication media 305 for communication purposes. It should be appreciated that links 802*a-d*, 804*a-b*, 806*a-b*, 808*a-b*, and 810 may be any type of communication link, including, for example, point-to-point, broadcast, multicast, etc. With respect to embodiments, it should be appreciated that like numbered elements shown in system 800 may be implemented in that manners described above.

FIG. 9A depicts system 900 that, for example, may be used in connection with wireless analyte (e.g., glucose) monitoring, and in some instances for diabetes management, including for example the provision of medicaments. System 900 may involve various components interconnected via one or more wired and/or wireless connections for the communication and exchange of information such as analyte data, medicament delivery data, diabetes management feedback and related guidance and services, alerts/notifications, control signaling, and/or other information. Embodiments of system 900 include one or more of analyte sensor 308; display devices 910, including mobile phone 910*a*, analyte display device 910*b*, and/or wearable device 910*c*; partner devices 915, which may include medicament delivery device 915*a*, first insulin pump 915*b*, second insulin pump 915*c*, and insulin pen 915*d*; and/or display devices 910', which may include mirror 910*d*, vehicle 910*e*, and/or key fob 910*f*. In the example implementation shown in FIG. 9A, these components are configured to be part of personal area network (PAN) 902, and are interconnected by links 906*a-j*, 908, 916, and 918, as shown in FIG. 9A, where these links can each respectively be implemented using communication media 305 for communication purposes. PAN 902 may employ a one or more of at least BLE, Wi-Fi, and the like.

System 900 may also include router 920*a* coupled to one or more devices within PAN 920 (e.g., to mirror 910*d* via link 914), though not all possible links are expressly shown. Router 920*a* may in turn be coupled via link 922 to server(s) 920(*b*) (e.g., server system 334, with reference to FIG. 2A), which may in turn be coupled via link 924 to cell network 920*c* (e.g., a 4G LTE network or the like). Cell network 920*c* may also be coupled via link 926 to cellular-enabled devices within PAN 902, such as mobile phone 910*a*. In embodiments, any of the devices shown in FIG. 9A may be cellular-enabled and thus couplable directly to cell network 920*c* and/or WAN 904 or elements thereof. For example, analyte sensor system 308 may be equipped with a cellular or other longer range radio component and may thus be couplable directly to cell network 920*c* and/or WAN 904 or elements thereof. As shown in FIG. 9A, router 920*a*, server(s) 920*b*, and cell network 920*c* may be configured to be part of wide area network (WAN) 904. Links 914, 922, 924, and 926 may be implemented using communication media 305 (e.g., may be wired or wireless, etc.). WAN 904 may generally provide cloud services to one or more devices in PAN 902. Again not all possible links between the devices in WAN 904 and the devices in PAN 902 are expressly shown, but they will be appreciated by one of skill in the art upon studying the present disclosure. It should also be appreciated that in some cases, elements of WAN 904 may be incorporated into PAN 902 and vice versa.

A number of the foregoing components of system 900 and features of the same have been described above with reference to at least, e.g., FIGS. 1, 2A, 2B, 3A-C, 4, 5A, 5B, 6, and 7A-C. One of skill in the art upon studying the present disclosure will recognize where and how the above descriptions of these components may be applicable here, whether or not the same is expressly conveyed herein.

With regard to system 900, where system 900 includes partner devices 915, two examples may drive the particular arrangement and/or implementation of the above-listed components of system 900 for wireless analyte monitoring and/or diabetes management. The first example does not involve medicament (e.g., insulin) delivery by partner devices 915 (e.g., by medicament delivery device 915*a*). Under this example, in embodiments, system 900 includes analyte sensor system 308, one or more display devices 910, 910' that are given authority to send command/control signals to analyte sensor system 308 (e.g., mobile phone 910*a* and/or analyte display 910*b*), as well as one or more display devices 910, 910' that are configured to be in a display only state (e.g., wearable device 910*c* and/or key fob 9100. In embodiments, this example involves display devices 910*a* and 910*b* operating in a command/control state (e.g., smartphone 120 or the like and analyte display device 110, referencing FIG. 1), and one or more display devices 910, 910' operating in a display only state (e.g., key fob 910*f* and smart mirror 910*d* or wearable device 910*c*, etc.).

The second example, unlike the first example, does involve medicament (e.g., insulin) delivery by at least one of partner devices 915 (e.g., medicament delivery device 915a). The medicament delivery by medicament delivery device 915 in this example may or may not be automated (e.g., an automated insulin pump or non-automated insulin pen). In this second example, where medicament delivery device 915a that delivers medicaments is part of system 900, interoperability issues may be introduced regarding which device (e.g., medicament delivery device 915, analyte sensor system 308, and/or display devices 910, 910') may control/manage the generation of analyte data, including for example the calculation of CGM values and the like.

With respect to this second example, in order to flexibly and adaptively support potentially varying and a priori unknown system requirements 650 (referencing FIG. 5B for example) of various partner devices 915 from an interoperability standpoint, where such partner devices 915 may be provided by various manufacturers/developers different from the manufacturers/developers of other components of system 900 (e.g., display devices 910, 910' and/or analyte sensor system 308, etc.), in some cases medicament delivery device 915a (or like partner devices 915) should be able to control the exchange of data between analyte sensor system 308 and display devices 910, 910' via links 906a-g. Such control may be provided, for example, by a user of display devices 910, 910 (e.g., a user of phone 910a, where authority for the control is given using mobile phone 910a to medicament delivery device 915 via link 916).

In embodiments, aspects of communication sessions and/or sensor sessions should also be controlled (e.g., partner devices 915, analyte sensor system 308, and/or display devices 910, 910' should in some cases be able to limit command/control signaling, including where such signaling is related to analyte data). For example, if medicament delivery device 915a is used for insulin delivery, the transmission of command signaling to analyte sensor system 308 may be restricted to only certain devices within system 900. Certain partner devices 915 may in some cases be generally less robust, for example, in terms of maintaining accuracy in a relatively high interference environment. In such cases, for example due to system requirements 650 of medicament delivery device 915a, the probability of medicament delivery device 915a receiving analyte data from analyte sensor system 308 inaccurately may be reduced where display devices 910, 910' are restricted from sending control/command signaling related to, e.g., starting, stopping, or calibrating of a sensor session. For example, such signaling may result in analyte sensor system 308 operating in a fashion that is not compatible or optimal or preferred with respect to medicament delivery 915a, as may be reflected for example by system requirements 650 thereof. In embodiments, it may be beneficial to delegate authority to send control/command signals to only particular devices within system 900 based on the device type and/or based on an operation mode of system 900. In embodiments, it may be beneficial to flexibly add or remove devices (e.g., partner devices 915 and/or display devices 910, 910') to/from system 900, whether in PAN 902 or WAN 904, to manage the access of such devices to analyte sensor system 308, and/or to manage how alerts propagate across various such devices and other devices within system 900.

In embodiments, it may also be beneficial to system 900 (including, e.g., for medicament delivery device 915a) to provide a means for controlling alert settings, for safety and/or robustness purposes. In embodiments, if certain links become unavailable (e.g., link 906d between analyte sensor system 308 and medicament delivery device 915a, link 922 between mobile phone 910a and cell network 920c, etc.), whether literally or due to system constraints such as power etc., and/or depending on other network conditions/configurations of PAN 902 and/or WAN 904 that will be discussed herein, it may be beneficial to adaptively modify aspects of system 900. Additionally, in some cases, it is beneficial to authenticate partner devices 915 attempting to establish a connection with analyte sensor system 308 and/or prevent unauthorized partner devices 915 from accessing analyte sensor system 308.

Accordingly, embodiments of the present disclosure provide a more flexible/adaptable system of analyte sensor system 308, display devices 910, 910' and/or partner devices 915, as well as methods of using the same, where such flexibility/adaptability may including setting or modifying configuration parameters 520 of analyte sensor system 308, alerts/alarms that may propagate through system 900, control/command capabilities of display devices 910, 910' and/or partner devices 915, connection models employed among devices in system 900, and so forth. In embodiments, the flexibility/adaptability is facilitated at least in part using diabetes management partner interface (DMPI) 750 that may be implemented using analyte sensor system 308. As will be described in further detail, in embodiments, various devices within system 900, including for example partner devices 915, can utilize DMPI 750 to access/modify configuration parameters 520 of analyte sensor system 308 and (re)configure aspects thereof and/or aspects of, e.g., display devices 910, 910', for operation in accordance with system requirements 650 of partner device 915 (e.g., medicament delivery device 915a). For example, system requirements 650 may be driven or based on safety and/or regulatory requirements applicable to medicament delivery device 915a, user experience configurations/settings/constraints, power consumption specifications/constraints, etc. System requirements 650 may be used to determine the format of data packages transmitted to partner devices 915 and/or display devices 910, 910' the display devices, as well as the protocol used for transmitting such data packages, based on the respective preferences/specifications/etc. of partner devices 915 and/or display devices 910, 910'.

With further reference to FIG. 9A, example embodiments involving various partner devices 915 within system 900 will now be described. In the below-described example implementations, system 900 may involve three partner devices 915, namely, first insulin pump 915b, second insulin pump 915c, and insulin pen 915d. Generally, these three partner devices 915 may each have different capabilities and performance characteristics, which may be reflected in certain respective system requirements 650 (referencing FIG. 5B) of the three partner devices 915, and each of the three partner devices 915 may use DMPI 750 (referencing FIG. 10A by way of example) of analyte sensor system 308 to modify configuration parameters 520 of analyte sensor system 308 in accordance with respective system requirements 650. In this manner, analyte sensor 308 may be adapted for better interoperability with any one of the first and second insulin pumps and the insulin pen, whichever partner device 915 is connecting to analyte sensor system 308 and/or within system 900. It will be appreciated upon studying the present disclosure that this description of first insulin pump 915b, second insulin pump 915c, and insulin pen 915d can apply equally to any examples of partner devices 915, including medicament delivery device 915a and similar devices.

For illustrative purposes, more detail will now be provided with respect to the respective characteristics of first and second insulin pumps 915b, 915c and insulin pen 915d in these example implementations. By way of example, first insulin pump 915*b* may have a relatively robust algorithm for administration of medicaments, may have a bigger (or higher capacity) battery or power supply, and may require blood glucose calibrations to occur every 12 hours. First insulin pump 915*b*'s relatively robust algorithm may essentially mean that the algorithm may be relatively less susceptible to interference from other devices that may attempt to connect to analyte sensor system 308, such as display devices 910, 910', including where such interference may involve interference during connection establishment or interference with sending command signaling to analyte sensor system 308. For example, the algorithm of first insulin pump 915*b* may be able to operate better across a larger range of configuration parameters 520, and may be able to better handle calibrations and start/stop events initiated by other devices. The 12 hour blood glucose calibration requirement may reflect accuracy constraints of the first insulin pump (and, e.g., can be reflected in system requirements 650 of first insulin pump 915*b*).

By way of further example, second insulin pump 915*c* may have a relatively less robust algorithm used in the administration of medicaments, may be less constrained in terms of blood glucose accuracy calibrations (e.g., may be able to use a factory calibration accuracy level), and may support remote services provided by server 920*b* (e.g., via a connection/link to server 920*b* directly through cell network 920*c* (which link is not shown in FIG. 9A), indirectly through router 920*a* (which link is also not shown), or indirectly for example through mobile phone 910*a*). Second insulin pump 915*c*'s relatively less robust algorithm may essentially mean that second insulin pump 915*c* was not designed to operate well in a high interference environment, where other devices within system 900 may be competing to establish connections with analyte sensor system 308 and/or may be sending command/control signaling thereto.

Continuing the illustrative example, insulin pen 915*d* may have hard/soft keys to receive user input, and may include a simple user interface, both of which can be represented for example by user interface 635 (referencing FIG. 5B). Insulin pen 915*d* may further be adapted to query and share data with analyte sensor system 308, for example to read analyte data therefrom and share insulin related information (e.g., related to dosage) therewith.

Given the above example information regarding first and second insulin pumps 915*b*, 915*c* and insulin pen 915*d*, example scenarios of how DMPI 750 may be used to flexibly adapt system 900 will now be provided. A first example scenario may involve the use of first insulin pump 915*b* with analyte sensor 308. Once first insulin pump 915*b* and analyte sensor system 308 are configured for use (e.g., applied to the user, powered on, etc.), the user's authorization for first insulin pump 915*b* to take control of analyte sensor system 308 and begin administered medicaments to the user may be requested. For example, such request may be provided to the user via user interface 435 of mobile phone 910*a* (referencing FIG. 4) that may be connected to analyte sensor system 308 and/or the first insulin pump, via user interface 635 of first insulin pump 915*b* (referencing FIG. 5B), and/or via a user interface of analyte sensor system 308. If the user authorizes the request, first insulin pump 915*b* may use DMPI 750 to access and set and/or modify configuration parameters 520 of analyte sensor system 308, in accordance with system requirements 650 of first insulin pump 915*b* (e.g., referencing FIG. 10A).

In this example, in terms of first insulin pump 915*b* accessing configuration parameters 520 via DMPI 750, the developer of first insulin pump 915*b* may have already integrated and tested pump 915*b* with analyte sensor system 308 prior to the products being sold or provided to the user. In this manner, first insulin pump 915*b* may include instructions, code, or other files in storage 615 that enable first insulin pump 915*b* to properly navigate DMPI 750 and configuration parameters 520. In embodiments, such instructions may be obtained by first insulin pump 915*b* by downloading and/or installing a software design kit associated with analyte sensor system 308. For example, insulin pump 915*b* may obtain such instructions or other information from server 920*b* and/or WAN 904 or elements thereof.

By way of example, first insulin pump 915*b* may use DMPI 750 to change one or more wireless connectivity parameters of configuration parameters 520. The wireless connectivity parameters may include settings related to a database that includes/stores information related to accessibility of devices (e.g., a whitelist) maintained by analyte sensor system 308, and first insulin pump 915*b* may change such whitelist settings, for example, such that first insulin pump 915*b* may not age off the whitelist until a battery level of first insulin pump 915*b* falls below a particular threshold (e.g., 5%). First insulin pump 915*b* may set the wireless connectivity parameters in this manner because, as mentioned above, first insulin pen 915*b* has a larger battery (e.g., higher battery capacity), and for example if for some reason first insulin pump 915*b* is disconnected from analyte sensor system 308 (e.g., by going out of range), then it may be beneficial for first insulin pump 915*b* to seek to re-establish connection with analyte sensor system 308 as soon as the opportunity arises.

First insulin pump 915*b* may use DMPI 750 to set or change additional wireless connectivity parameters, such as a timeout setting for the transmission of advertisement messages, for example so that analyte sensor system 308 advertises for a total of 1 second before ceasing the transmission of advertisement messages. That is, in this example, advertisement duration 614 (referencing FIG. 6) may be set to 1 second. First insulin pump 915*b* may set the wireless connectivity parameters in this manner because first insulin pump 915*b* may have a relatively accurate scanning algorithm (e.g., as may have been determined by developers of first insulin pump 915*b* or by other means), such that first insulin pump 915*b* may be able to reliably establish a connection with analyte sensor system 308 when appropriate (e.g., once every advertisement window interval 612, which may be 5 minutes in some cases) without advertising for a longer duration. By shortening advertisement window interval 612, battery power may be saved.

Furthermore, first insulin pump 915*b* may use DMPI 750 to change one or more access control parameters of configuration parameters 520. The access control parameters may include, for example, a number of display devices 910, 910' that analyte sensor system 308 can maintain a connection with, and/or may include, for example, a level of access or control such display devices 910, 910' may have with respect to analyte sensor system 308. By way of illustration, first insulin pump 915*b* may set either or both of these access control parameters such that there are no restrictions imposed. First insulin pump 915*b* may set the access control parameters in this manner because, as mentioned above, first insulin pump 915*b* may have a relatively robust algorithm for insulin administration, and therefore may not need to prevent other devices from sending calibrations etc. (e.g., because first insulin pump 915*b*'s algorithm may be able to handle such outside events and adjust to them accordingly).

Additionally, first insulin pump 915*b* in this example may use DMPI 750 to change one or more analyte data parameters of configuration parameters 520. The analyte data parameters may include a calibration period for analyte sensor system 308. For example, first insulin pump 915b may set the calibration period to 12 hours, per the above-mentioned system requirement 650 of first insulin pump 915b.

A second example scenario may involve the use of second insulin pump 915c with analyte sensor 308. Similar to the above example involving first insulin pump 915b, after set up and authorization, second insulin pump 915c may use DMPI 750 to access and set and/or modify configuration parameters 520 of analyte sensor system 308, in accordance with system requirements 650 of second insulin pump 915c (e.g., referencing FIG. 10A). Similar to the previous example, in terms of second insulin pump 915c accessing configuration parameters 520 via DMPI 750, the developer of second insulin pump 915c may have already integrated and tested the pump with analyte sensor system 308 prior to the products being sold or provided to the user. In this manner, second insulin pump 915c may be adapted to properly navigate DMPI 750 and configuration parameters 520. In embodiments, second insulin pump may also reconfigure DMPI 750 before accessing configuration parameters 520.

With respect to the second example scenario, several situations are contemplated here. In a first situation, where, as an initial matter when deciding to employ an insulin delivery device, the user selects second insulin pump 915c instead of first insulin pump 915b or insulin pen 915d. In a second situation, the user may have already been using first insulin pump 915b or insulin pen 915d for a time but then may switch to second insulin pump 915c. That is, while first and second insulin pumps 915b and 915c and/or insulin pen 915d are not necessarily used simultaneously, this example encompasses first and second insulin pumps 915b and 915c and/or insulin pen 915d being used in a serial fashion (e.g., user decides to use different pump product, or the first pump product breaks, etc.) It should also be appreciated that any partner devices 915 may be used in a serial fashion.

By way of example, second insulin pump 915c may use DMPI 750 to set or change wireless connectivity parameters of analyte sensor system 308, including the timeout setting for the transmission of advertisement messages, for example so that analyte sensor system 308 may advertises for a total of 5 seconds before ceasing the transmission of advertisement messages. Second insulin pump 915c may set the wireless connectivity parameters in this manner because second insulin pump 915c may have a relatively less accurate scanning algorithm (e.g., as may have been determined by developers of second insulin pump 915c or by other means), such that second insulin pump 915c may not be able to as reliably establish a connection with analyte sensor system 308 when appropriate (e.g., once every advertisement window interval 612, which may be minutes in some cases) without advertising for a relatively longer duration.

Additionally, second insulin pump 915c in this example may use DMPI 750 to change additional wireless connectivity parameters. Such wireless connectivity parameters may be related to the use of remote (e.g., cloud-based) services that for example may be provided by server 920b (e.g., services 805 with reference to FIG. 8). By way of illustration, second insulin pump 915c may set the wireless connectivity parameters to enable the use of such remote services (e.g., a cloud-based support module), and to configure analyte sensor system 308 to transmit diabetes management feedback received in connection with such remote services to display devices 910, 910' that may be within range of and/or connecting to analyte sensor system 308 (e.g., where in some cases display devices 910, 910' may be in a display only state/mode). Second insulin pump 915c may set these wireless connectivity parameters in this fashion because second insulin pump 915c may have been approved to propagate such diabetes management feedback to other display devices 910, 910', etc. Furthermore, second insulin pump 915c may set these wireless connectivity parameters such that if the remote services become unavailable (e.g., by loss of a link, such as for example links 914, 922, 924, or 926, or the like, to server 920b), then the diabetes management feedback feature may be disabled and a related notification to display devices 910, 910' etc. that may be within range of and/or connecting to analyte sensor system 308.

Furthermore, second insulin pump 915c may use DMPI 750 to change one or more access control parameters of configuration parameters 520, including for example by setting the number of display devices 910, 910' that analyte sensor system 308 can connect to three devices, and by setting the level of access or control of such display devices 910, 910' with respect to analyte sensor system 308 such that the up to three display devices 910, 910' operate in a display only state or mode wherein such display devices 910, 910' may be able to display analyte and/or insulin delivery data, related notifications/alarms, and other information, but are without the ability to send control/command signaling to analyte sensor 308. Second insulin pump 915c may set the access control parameters in this manner because, as mentioned above, second insulin pump 915c may have a relatively less robust algorithm for insulin administration, and therefore may seek to prevent other devices from sending calibrations etc. (e.g., because second insulin pump 915c's algorithm may not be able to handle such outside events or adjust to them accordingly).

Moreover, with respect to the analyte data parameters that may be included in configuration parameters 520, second insulin pump 915c may not make any changes to the factory calibration parameters (e.g., including the factory calibration period) that may be default for analyte sensor system 308 as provided off the shelf or by the manufacturer thereof. This may be because, as mentioned above, second insulin pump 915c can use a factory calibration accuracy level. In this situation, analyte sensor system 308 may not generate calibration prompts, and can simply follow the default calibration schedule.

A third example scenario may involve the use of insulin pen 915d with analyte sensor system 308. Similar to the above example involving first and second insulin pumps 915b, 915c, after set up and authorization of insulin pen 915d for use, including for multiple daily injections of insulin that may be made manually, insulin pen 915d may use DMPI 750 to access and set and/or modify configuration parameters 520 of analyte sensor system 308, in accordance with system requirements 650 of insulin pen 915d (e.g., referencing FIG. 10A). Similar to the previous examples, in terms of insulin pen 915d accessing configuration parameters 520 via DMPI 750, the developer of insulin pen 915d may have already integrated and tested the pen with analyte sensor system 308 prior to the products being sold or provided to the user. In this manner, insulin pen 915d may be adapted to properly navigate DMPI 750 and configuration parameters 520.

By way of example, insulin pen 915d may use DMPI 750 to change one or more access control parameters of configuration parameters 520, including for example making a selection to establish a direct connection with analyte sensor system 308, as opposed to establishing a connection to analyte sensor system 308 indirectly, e.g., via mobile phone 910*a*. Notwithstanding this selection, mobile phone 910*a* may still establish connections with analyte sensor system 308 and/or insulin pen 915*d* and exchange information therewith, subject to how configuration parameters 520 may otherwise be set.

Insulin pen 915*d* may also use DMPI 750 to change wireless connectivity parameters for analyte sensor system 308, including with respect to the transmission of advertisement messages, for example so that analyte sensor system 308 can advertise according to default settings for display devices 910, 910', etc., but with respect to insulin pen 915*d* analyte sensor system 308 can advertise using an extended advertisement duration 614 and/or an decreased advertisement window interval 612 (referencing FIG. 6). Insulin pen 615*d* may set the wireless connectivity parameters in this manner because for devices such as insulin pen 615*d*, users may need a more responsive system that for example has access to up to date glucose data readily available to the user.

Additionally, insulin pen 615*d* may use DMPI 750 to access analyte data parameters of configuration parameters 520 to enable the use of a bolus calculator that may be implemented, for example, by analyte sensor system 308. For example, DMPI 750 may provide insulin pen 915*d* with access to bolus calculation parameters that may be maintained by analyte sensor system 308, such that analyte sensor system 308 can modify the bolus calculation parameters. In embodiments of the present disclosure, analyte sensor system 308 may use the bolus calculation parameters to provide a bolus-related recommendation to the user, where the recommendation is based on a calculation performed by analyte sensor system 308 using the bolus calculation parameters (e.g., and a bolus calculator of analyte sensor system 308).

Insulin pen 915*d* in this example may also use DMPI 750 to change one or more additional analyte data parameters of configuration parameters 520. For example, insulin pen 915*d* may set the calibration period to 12 hours, in some cases for reasons similar to those discussed above with respect to system requirement 650 of first insulin pump 915*b*.

With further regard to example scenario involving insulin pen 915*d*, in some cases, the user may want and/or need to administer insulin, and may accordingly select a bolus value on insulin pen 915*d* (e.g., using user interface 635, with reference to FIG. 6). A connection may then be established between insulin pen 915*d* and analyte sensor system 308, such that insulin pen 915*d* may send the user's selected bolus value thereto. If the user's blood glucose level is declining more than is preferable/normal, and/or if the user already has a substantial amount of insulin on board, then analyte sensor system 308 can use the above-mentioned bolus calculator to make a bolus-related recommendation to the user and/or a safety decision. Analyte sensor system 308 may in this situation send a notification or alert to the user regarding the amount of insulin selected by the user (e.g., that the selected bolus value is too high). In such cases, analyte sensor system 308 can attempt to prevent the user from injecting the selected bolus value. For example, there may be a mechanical prevention feature on insulin pen 915*d* that prevents the user from injecting a bolus that exceeds the bolus value calculated by analyte sensor system 308. Such a mechanical prevention feature may be implemented, for example, by disabling (retracting) medicament delivery mechanism 640 (e.g., a needle) and/or preventing an overly large bolus from being moved into an injection reservoir of the insulin pen. Signaling from analyte sensor system 308 may trigger the mechanical prevention feature, for example.

As will be described below, additional configuration parameters 520 and/or system requirements 650 may be present in embodiments of system 900, and one of ordinary skill in the art will appreciate upon studying the present disclosure additional aspects of using configuration parameters 520 and/or system requirements 650 in the context of the above example scenarios as well as in other contexts expressly or implicitly described or alluded to herein. It should be appreciated that the above example scenarios and features thereof are not necessarily required in all embodiments of the present disclosure, and with respect to embodiments may disclosed features by way of illustration only.

Figure 10A:
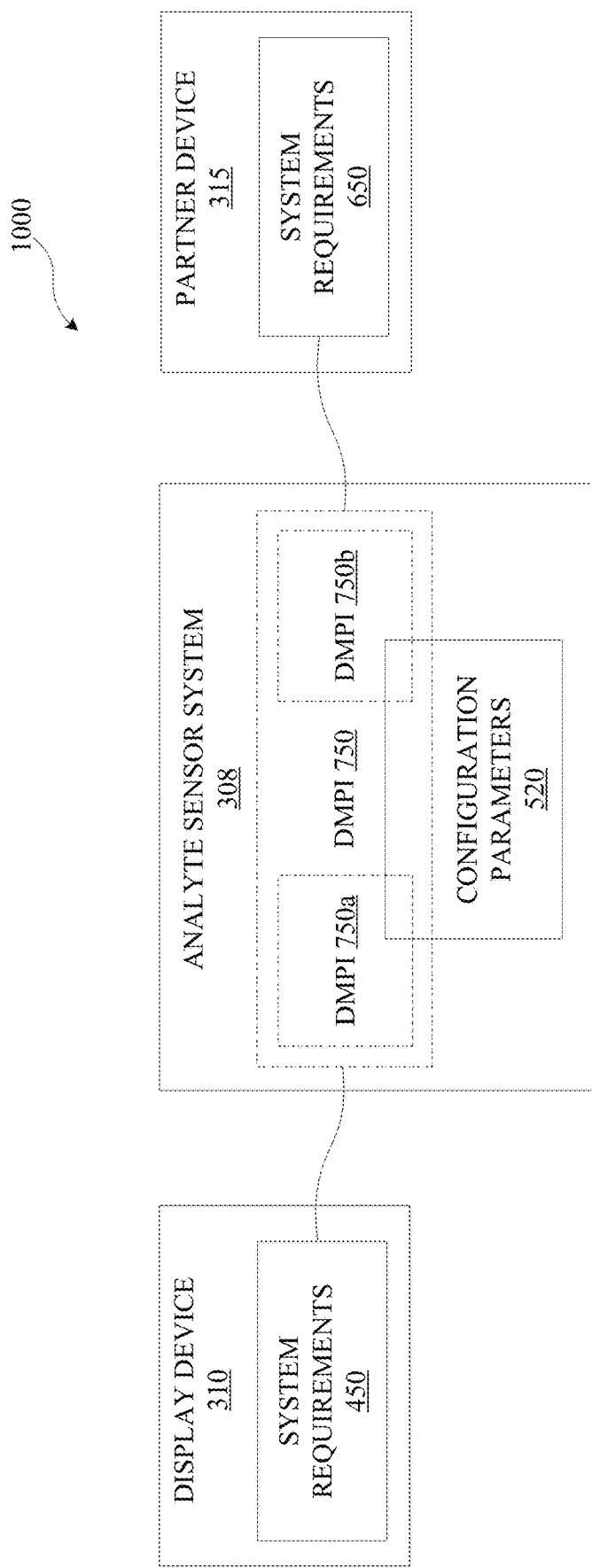
FIG. 10A illustrates aspects of an example system that may be used in connection with implementing embodiments of the disclosure.

Given the general context of the above example scenarios, additional details regarding configuration parameters 520 and system requirements 650 will now be described with reference to FIG. 10A. For example, as shown in FIG. 10A, within system 1000, partner device 315 may include system requirements 650 associated therewith that should be met in order to support functionality according to pre-determined expectations, design constraints, system specifications, and/or the like. In order to support system requirements 650, partner device 315 may use DMPI 750 of analyte sensor system 308 to access configuration parameters 520 (e.g., of analyte sensor system 308). Configuration parameters 520 can serve as flexible settings that may be adapted, varied, programmed, set, and/or modified by partner device 315 using DMPI 750 such that communications between/among analyte sensor system 308, partner device 315, and/or display device 310 allow system requirements 650 to be met.

By way of example, configuration parameters 520 may include wireless connectivity parameters, access control parameters, power management parameters, and/or analyte data parameters. The wireless connectivity parameters may generally relate to wireless connectivity and communications within system 900 (referencing FIG. 9A, and/or system 800 referencing FIG. 8, etc.), and the handling of wireless communications and connectivity with analyte sensor system 308, including with and/or by one or more of display device 310 and partner device 315, as well as other connections that are described herein (e.g., between display device and partner device 315).

The wireless connectivity parameters may relate to aspects of a whitelist that may be maintained by analyte sensor system 308. For example, the wireless connectivity parameters may relate to age-off settings by specific devices or groups of devices. For example, where partner device 315 is an insulin pump that dies, a default age-off time may be used as a backup mechanism to halt the use of the insulin pump in case the user does not realize the pump has died, though the age-off in this scenario may be subject to user override in the event that the user approves not aging off the pump. In example implementations, the pump may have a known lifespan, and the age-off time may be set to accommodate this. For example, the known lifespan may be battery-driven and/or the pump may need to be replaced/serviced after a known amount of time, which may be reflected in system requirements 650, and the pump may set its age off time accordingly by modifying configuration parameters 520 using DMPI 750. This age off time may be adjusted on the fly, for example, if problems arise sooner than expected, or if due to intervening circumstances the expected issues are pushed out in time (e.g., due to efficient power management or less power-hungry use than expected). Additionally, partner device 315 may be able to use DMPI 750 to modify whitelist settings in order to force certain devices to age off the whitelist such that battery budget may be saved vis-à-vis analyte sensor system 308 and/or partner device 315.

In embodiments, the wireless connectivity parameters may relate to a hierarchy/prioritization of connection ordering among connectable devices (e.g., by types of devices, by particular devices, etc.). The wireless connectivity parameters may relate which devices or types of devices may be whitelisted (e.g., partner devices 315 vs. display devices 310, and including particular devices). In embodiments, the wireless connectivity parameters may relate to connection modes (as will be described in further detail elsewhere herein) to be employed for certain devices or under certain conditions; and/or to network configuration settings, e.g., to provide fallback configurations and/or routines in case certain connections, such as cloud, cellular, or personal area network connections, are not available, etc.

In embodiments, the wireless connectivity parameters may include a condition under which partner device 315 is to be removed from a whitelist maintained by analyte sensor system 308. The condition may be set/modified such that partner device 315 is to be removed from the whitelist when a battery level of partner device 315 meets or crosses a threshold. For example, if the battery level of partner device 315 drops such that the use of partner device 315 may not be sustainable for much more time (e.g., less than 10%), partner device 315 may be removed from the whitelist, and the user may be notified that the user should not rely on partner device 315 going forward (e.g., for the delivery of medicaments etc.).

For example, the wireless connectivity parameters may include wireless connection settings, such as settings related to advertising timeouts, structure, and/or protocols. With reference to FIG. 6, in embodiments, the wireless connectivity parameters may be used to set/modify advertisement structure 622, advertisement duration 614, advertisement window interval 612, and/or advertisement period 616. In some cases, the wireless connectivity parameters may relate to settings in server system 334 and/or the user of services provided via server system 334.

The power management parameters that may be included in configuration parameters 520 may be used to implement battery budget control, for example. In some cases, configuration parameters 520 related to power management may be implemented based on system requirements 650 of partner device 915, as well as power management concerns regarding analyte sensor system 308 and/or display devices 910, 910'. For example, even if system requirements 650 indicate that a particular partner device 915 would be power-hungry, a decision may still be made as to whether such a partner device 915 should be allowed to consume the power that would satisfy system requirements 650. Accordingly, embodiments of the present disclosure involve controlling how the battery budget is allocated between/among analyte sensor system 308, partner devices 915, and/or display devices 910, 910'. For example, thresholds may be set, in some cases on per-device basis, such that if it is determined that proposed settings for power management parameters would cause such thresholds to be met, user approval may be requested before such proposed settings are implemented vis-à-vis configuration parameters 520.

In embodiments where system requirements 650 may create power management implications for analyte sensor system 308, configuration parameters 520, including in some cases parameters other than power management parameters may be set/modified in order to effect a trade-off between data reliability and battery life of analyte sensor system 308. For example, certain wireless connectivity parameters, e.g., as discussed above, may be set to age off particular display devices 910, 910' in response to power management implications created by system requirements 650. In additional examples, aspects of advertisement structure 622 (e.g., with reference to FIG. 6) may be modified via settings/modifying configuration parameters 520 in order to manage power consumption. In yet further examples, connection models and/or operating modes may be changed in order to manage power consumption, and such changes may be effected via settings/modifying configuration parameters 520. In some cases, the trade-off between data reliability and battery life may be determined using a slide bar provided by user interface 435 (for example referencing FIG. 4) and/or running on analyte sensor application 425*a* and/or partner device application 425*b*. In embodiments, the trade-off may be implemented through an automatic adjustment to configuration parameters 520. For example, a low battery mode may be implemented using a predetermined set of values for configuration parameters 520. Such a mode may be entered automatically or manually or semi-manually with some user intervention.

The analyte data parameters that may be included in configuration parameters 520 may include, for example, algorithm settings for analyte sensor system 308 (e.g., calibration schedule/settings, CGM start/stop/calibrate access, factory calibration settings, etc.), alert/alarm/notification settings (e.g., to set which display device 310/partner device 315 receives which alerts, which display device 310/partner device 315 can acknowledge or respond to which alerts, if special alerts are enabled for particular partner devices, the ordering for sending/escalating alerts, the types of alerts to send under certain conditions, etc.). The analyte data parameters may include accuracy parameters and/or calibration parameters for analyte sensor system 308. For example, the calibration parameters may include a calibration period for analyte sensor system 308. The calibration period may be modified or set in accordance with system requirements 650 of partner device 315 regarding required accuracy levels of analyte or CGM data. For example, partner devices 315 from different manufacturers may have different accuracy requirements and may thus impose different demands on calibrations. The analyte data parameters may also include a factory calibration code that can be used to set or modify the calibration period (e.g., in some cases to set the calibration period to zero). In example embodiments, the analyte data parameters include bolus calculation parameters that may be used to perform calculations and provide bolus recommendations based on the calculations. In example embodiments, the analyte data parameters may concern the types of analyte information that can be read/sent, including for example expected glucose value (EGV), rate, state, predicted EGV, errors, and the like.

The access control parameters that may be included in configuration parameters 520 may include one or more of a number of display devices 310 and/or partner devices 315 connectable to analyte sensor system 308, and a level of access or control analyte sensor system 308 may give to one or more of display devices 310 and/or partner devices 315 in terms of sending command and/or control signaling to analyte sensor system 308 where the command/control signaling relates to analyte data. In some cases, before being granted, the level of access or control may need to be approved by a user (e.g., via analyte sensor application 425*a* and/or partner device application 425*b*, with reference to FIG. 4). Different types of display devices 310 and/or partner devices 315 may be granted different levels of access or control. In embodiments the access control parameters may include security and/or privacy related parameters. For example such security/privacy parameters may involve encryption keys that may be used for exchanging information with partner devices 315. In some cases, analyte sensor application 425*a* and partner device application 425*b* and/or medicament delivery application 625 may generate public and private keys where the public keys are shared and the private keys are used to encrypt data exchange among the applications. In some cases, such keys may be stored remotely, for example in server 920*b*. Additional security/privacy features may involve identity resolution and/or tracking prevention.

By way of example, referencing FIG. 9A, in some cases, if a user wants to add a display device 910, 910' or a partner device 915 to system 900, mobile phone 910 (or another display device 910, 910') may notify the user regarding changes that may result to the user's piconet structure (e.g., in terms of how command/control commands may be used, how alerts and alarms may change, etc.). This may be done using a known mapping of how system requirements 650 of partner device 915 may imply modifications to configuration parameters 520. In some cases, the addition of display devices 910, 910' or partner devices 915 to system 900 may be subject to an approval procedure implemented by a specific partner device 915, for example so that partner devices 915 can confirm that system requirements 650 will still be met with the addition of the device. Regarding the addition of partner and/or display devices 915, 910, 910', the user may provide authorization ahead of time for specific devices using application 425*b*.

In embodiments, configuration parameters 520 may be adapted automatically in response to changes relating to system 900. By way of example, medicament delivery devices 915*a* or other partner device 915 may become unavailable, in which case configuration parameters 520 may be modified and/or may be restored to a prior state. Additionally, configuration parameters 520 may be adapted in response to system 900 entering into a particular operating mode, as described below. For instance, in the hybrid operating mode, configuration parameters 520 may be modified so that medicament delivery device 915*a* may be configured to use the continuous connection model. Configuration parameters 520 may be adapted according to a projected battery life of medicament delivery device 915*a*, for example to change the connection model used to connect analyte sensor system 308 and medicament delivery device 915*a* in order to save battery. In embodiments, configuration parameters 520 may be modified adaptively based on time of day, location, or radio conditions. The user may delegate certain controls to any devices within system 900. For example, the user may authorize medicament delivery device 915*a* to act as a system administrator of sorts, such that medicament delivery device 915*a* handles the addition/removal of display devices 910, 910', connection models and operating modes, management of alerts, authentication/encryption processes, etc. Once authorized by the user, processes may be managed and permissions granted as need, for example using a system of registration and subscription or various services or characteristics (e.g., that may be supported in BLE).

Additionally, in embodiments, as display devices 910, 910' are added/removed from system 900, there may be implications on system requirements 650 of partner devices 915 that trigger modifications to configuration parameters 520 or other aspects of system 900. For example, system requirements 650 may impose a limit on the number of display devices 910, 910' that may be connectable to analyte sensor system 308. If that limit is implicated by the addition of display devices 910, 910', certain other display devices 910, 910' may be removed to maintain operation in accordance with system requirements 950. The removal may occur following a pre-determined hierarchy of display devices 910, 910' that should be removed if the limit is implicated, or may be based on removing a particular display device 910 if similar display devices 910, 910' are connectable (e.g., removing a user's PC if the user's tablet is also connectable).

Configuration parameters 520 may also accommodate specific scenarios that may be encountered in connection with the use of medicament delivery device 915*a* in system 900. One such scenario involves the exchange of medicament deliver device 915*a* for a new medicament delivery device 915*a* (e.g., as described below in connection with operating modes). For example, medicament delivery device 915*a* may become old or otherwise subject to disposal. In example implementations, medicament delivery device 915*a* may be disposable, e.g., may be designed to have a known usable life, after which medicament delivery device 915*a* should be replaced in its entirety. By way of illustration, where medicament delivery device 915*a* is an insulin pump, a pump session may end after 3 days, at which time the pump may need to be replaced, in whole or in part (e.g., in some cases, just medicament delivery mechanism 640 may need to be replaced, referencing FIG. 5B). In embodiments, analyte sensor system 308 may likewise need to be replaced periodically, in whole or in part (e.g., in some cases, just continuous analyte sensor 10 may need to be replaced, referencing FIG. 1), and the replacement period may differ from the that of medicament delivery device 915*a*. For example, the replacement period for analyte sensor system 308 may be 7 days.

The difference in replacement periods as between medicament delivery device 915*a* and analyte sensor system 308 may result in a situation in which a sensor session for analyte sensor system 308 to collect and generate analyte data is expiring while the pump session for medicament delivery device 915*a* is ongoing. This can potentially create medical complication for the user of analyte sensor system 308 and medicament delivery device 915*a*, because the user may need to replace at least a component of analyte sensor system 308, but medicament delivery device 915*a* may require continuous, substantially continuous, or at least somewhat regular reception of analyte data generated using analyte sensor system 308. Changing at least a component of analyte sensor system 308 (e.g., sensor 10), can disrupt the at least somewhat regular reception of analyte data that may be required/expected by medicament delivery device 915*a*.

Accordingly, embodiments of the present disclosure involve using DMPI 750 to facilitate relatively undisrupted operation of medicament delivery device 915*a* through periodic device/component replacements that may occur with respect to analyte sensor system 308 and/or medicament delivery device 915*a*. In embodiments, this may involve analyte sensor system 308 indicating to a user thereof when the medicament delivery session of medicament delivery device 915*a* and/or the sensor session of analyte sensor system 308 is expected to end (e.g., when medicament delivery device 915*a* is expected to need replacement of at least a component thereof). For example, this may entail one or more of analyte sensor application 425*a*, partner device application 425*b*, mobile phone 910*a* (or other display device 910, 910'), medicament delivery application 625, and medicament delivery device 915a notifying the user of the expected replacement in advance (e.g., replacement is expected in 12 hours).

In the case of medicament delivery device 915a (or a component thereof) being replaced, the replacement medicament delivery device 915a can then essentially mimic the communication of the old medicament delivery device 915a to take the whitelist slot of the old medicament delivery device 915a. This may allow for an overlap in the sensor session with the medicament delivery session in order to avoid or reduce the effects of a discontinuity that may arise in connection with the replacement. By way of example, the old medicament delivery device 915a may send data to mobile phone 910a where the data enables analyte sensor system 308 to establish communication with the new medicament delivery device more easily. This information may be used to bond both the old and new medicament delivery device to 910a at the same time. That is, for example, where analyte sensor system 308 does not have new medicament delivery device 915a's bonding data, mobile phone 910a can send bonding data information from old medicament delivery device 915a to new medicament delivery device 915a, such that new medicament delivery device 915a may use the bonding data for facilitating connection establishment with analyte sensor system 308. For example, analyte sensor system 308 could whitelist advertise to new medicament delivery device 915a, and new medicament delivery device 915a could then respond using bonding information of old medicament delivery device 915a. By way of further illustration, new medicament delivery device 915a may use the information regarding old medicament delivery device 915a received via mobile phone 910a to replicate the GAPP address, encryption and security keys, other bonding information, and/or timing information (e.g., regarding timing of connections, advertisement intervals etc.), as employed by old medicament delivery device 915a.

In embodiments, for this to occur, the information may need to be transferred from old medicament delivery device 915a to new medicament delivery device 915a. Other information may be transferred as well, such as for example insulin on board, diagnostics, etc. The transfer may be facilitated by analyte sensor system 308. For example, DMPI 750 may be used to access/retrieve the information from old medicament delivery device 915a and share the information with mobile phone 910a for subsequent transfer to new medicament delivery device 915a.

In embodiments, configuration parameters 520 may be used to enable analyte sensor system 308 to effectively simulate aspects of a previously implemented analyte sensor system 308. For example, medicament delivery device 315a may have previously been integrated with and/or used with a particular analyte sensor system 308 that employed a specific algorithm for generating analyte data. In some cases, a clinical trial may have been run using such a particular analyte sensor system 308, and the clinical trial may have been approved and/or successful. Configuration parameters 520 used in the particular analyte sensor system 308 could be stored in medicament delivery device 915a and via DMPI 750 could be used to update configuration parameters 520 as stored in analyte sensor system 308. As such, analyte sensor system 308 may be configured to in effect simulate the previously implemented analyte sensor system 308.

In embodiments, the simulation of another analyte sensor system 308 may be accomplished in various ways. For example, accuracy metrics associated with the simulated analyte sensor system 308, such as MARD and/or other accuracy metrics may be replicated and implemented through modifying configuration parameters 520. Sensor algorithms, calibration settings, wireless connectivity parameters, and any aspects of other configuration parameters 520 described herein, including connection models and operating modes that were employed previously (for example, in a clinical trial) can also be simulated through the setting and/or modifying of configuration parameters 520.

In embodiments, a range of values for configuration parameters 520 of analyte system sensor system 308 may be defined, for example by medicament delivery device 915a, server 920b, or other remote source, where the range of values represents a set of safe operating parameters. The safe operating parameters can represent or be equivalent to configuration parameters previously determined to have satisfied certain requirements, such as those required by the FDA. Examples of such configuration parameters 520 include additive bias, multiplicative bias, lag, gaps, and sampling rates. Accordingly a set of configuration parameters 520 previously determined to be acceptable may be downloaded to analyte sensor system 308 and implemented with the understanding that certain requirements previously tested will be met.

Turning back to FIG. 10A, with respect to system requirements 650 of partner device 315, in embodiments, system requirements 650 may largely (but do not necessarily) mirror configuration parameters 520 described above. System requirements 650 may include or be associated with one or more of a battery capacity or power management of partner device 315, an accuracy requirement of partner device 315, a communication protocol to be used or supported by partner device 315, a regulatory requirement applicable to partner device 315, and an expected operational time of partner device 315.

With respect to accuracy requirements of partner device 315, certain system requirements 650 may relate to calibrations of analyte sensor system 308 vis-à-vis the gathering and generation of analyte data. For example, system requirements 650 may include a calibration schedule, calibration control, and/or a factory calibration applicable to analyte sensor system 308. As discussed elsewhere herein, certain partner devices 315 may be capable of tolerating inaccuracies that may be generated using a factory calibration at analyte sensor system 308 (e.g., may be relatively more robust), while other partner devices may require greater accuracy and hence difference calibration settings. Exposing these calibration-related (and other) system requirements 650 to analyte sensor system 308 using DMPI 750 can allow configuration parameters 520 of analyte sensor system 308 to be adapted to handle a variety of partner devices 315 with varying degrees of robustness.

In some cases, as will be discussed below with reference to FIGS. 10A and 10B, the nature and/or extent of system requirements 450 that may be stored on display device 310, and/or whether system requirements 450 are stored on display device 310, may vary depending upon the particular arrangement of analyte sensor system 308, display device 310, and/or partner device 315. In some cases, system requirements 450 that may be stored on display device 310 may be exposed to or received from or modified by partner device 315 via DMPI 750 that can allow partner device to set/modify system requirements 450.

With reference to FIG. 10A, in some cases, display device 310 may include system requirements 450, where at least some of system requirements 450 may be associated with display device 310 such that such system requirements 450 should be met in order to support functionality according to pre-determined expectations, design constraints, system specifications, and/or the like as pertaining to display device 310. In order to support system requirements 450, display device 310 may use DMPI 750 of analyte sensor system 308 to access configuration parameters 520, in a fashion that may be substantially similar to that described above in connection with partner device 315 accessing configuration parameters 520.

In embodiments, system requirements 450 may not pertain to display device 310 (or at least not solely to display device 310), but may (in addition) pertain to partner device 315. For example, where display device 310 has established a connection with analyte sensor system 308, and it is expected that partner device 315 may be used in the future, display device 310 may obtain and store system requirements 650 of partner device 315 as at least part of system requirements 450. Then, display device 310 may, via DMPI 750, set/modify configuration parameters 520 in preparation for partner device 315 establishing a connection with analyte sensor system 308, such that upon such connection being established, operation may go forward according to system requirements 650 but without partner device 315 making any (or perhaps minimal) modification to configuration parameters 520. Or, for example, display device 310 may upload system requirements 450 to analyte sensor system 308 (e.g., via DMPI 750) with an indication that system requirements 450 pertain to partner device 315, such that a set of configuration parameters 520 may be pre-configured in anticipation of establishing connection with partner device 315. Once a connection is established between analyte sensor system 308 and partner device 310, the pre-configured set of configuration parameters 520 may be implemented, and operation may go forward according to system requirements 650 but without partner device 315 making any (or perhaps minimal) modification to configuration parameters 520.

FIG. 10A also shows that in embodiments of system 1000, DMPI 750 may include one or more of sub-interfaces or separate interfaces DMPI 750a and DMPI 750b, as the case may be. In such embodiments, DMPI 750a may be dedicated or allocated to display device 310 for accessing analyte sensor system 308, while DMPI 750b may be dedicated or allocated to partner device 315. Referring to FIG. 9A, in some cases, DMPI 750a may be specific to a particular display device 910, 910' (or group thereof), and/or DMPI 750b may be specific to a particular partner device 915 (or groups thereof).

Figure 10B:
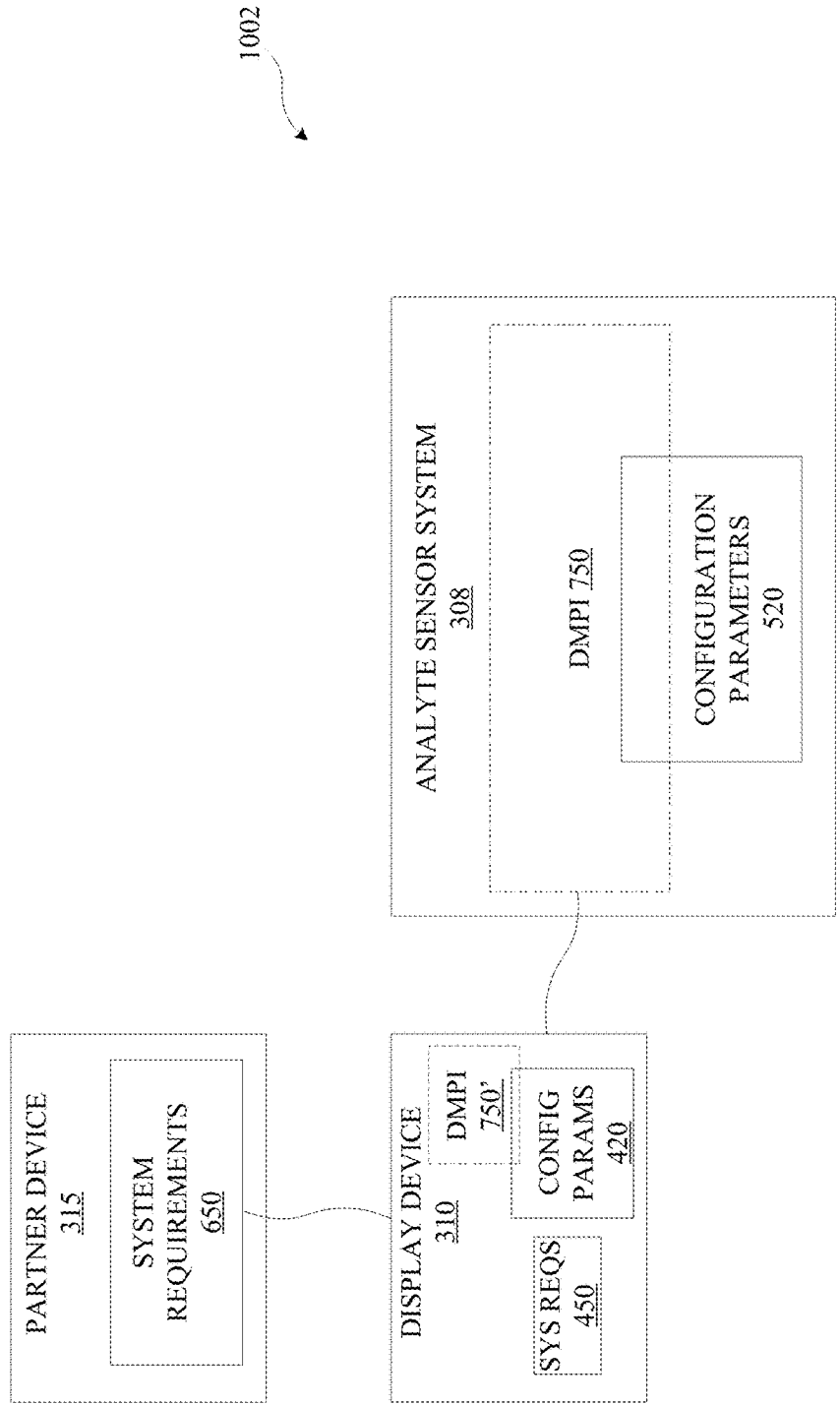
FIG. 10B illustrates aspects of an example system that may be used in connection with implementing embodiments of the disclosure.

FIG. 10B illustrates example system 1002, in which partner device 315 includes system requirements 650 associated therewith. Partner device 315 is not connected directly with analyte sensor system 308 in this example, but rather is connected therewith through intermediary display device 310. As shown, display device 310 may include DMPI 750'. Partner device 315 may use DMPI 750' to access, set, and/or modify configuration parameters 420 stored in display device 310. In order to support system requirements 650, display device 310 may then access configuration parameters 520 of analyte sensor system 308 using DMPI 750 and may set configuration parameters 520 according to the values for configuration parameters 420 set by partner device 315. In this manner, configuration parameters 520 may be adapted in accordance with system requirements 650 where partner device 315 is not directly connected to analyte sensor system 308.

At this juncture, embodiments of methods and features that may be implemented in connection with system 900 shown in FIG. 9A will now be described with reference, by way of example to FIGS. 9B through 9F, 9J, and 9K. FIG. 9B is an operational flow diagram illustrating various operations that may be implemented, for example, using elements shown in FIG. 9A. FIG. 9B shows operations 932A and 932B of method 930, where method 930 may involve using DMPI 750 (with reference by way of example to FIG. 10A) to configure analyte sensor system 308 for wireless communication with partner devices 915. The operations of method 930 may be used advantageously to implement a flexible and adaptable system wherein different partner devices from different manufacturers may be accommodated through the use of a configurable diabetes management partner interface.

At operation 932A, method 930 includes analyte sensor system 308 receiving authorization to provide one of partner devices 915 (for example, medicament delivery device 915a) with access to configuration parameters 520 (referencing FIG. 5B by way of example) stored in storage 515 (referencing FIG. 3C for example) of analyte sensor system 308. The authorization may be received from, for example, a user who may provide the authorization via mobile phone 910a or other display device 910, 910' using caps PAN 902 and/or caps WAN 904. The access to configuration parameters 520 may be provided via DMPI 750. At operation 932B, method 930 involves analyte sensor system 308 setting or causing a modification to configuration parameters 520, whereas described above the modification may be made according to system requirements 650 of the one partner device 915. Operation 932B occurs responsive to input received, for example over a link in PAN 902 (e.g., link 906d, 906h, 906i, 906j) from the one partner device via DMPI 750. In embodiments, the one partner device 915 may be implemented as an automatic insulin delivery device (for example, an insulin pump) or a manual insulin delivery device (for example, an insulin pen).

As described above, in embodiments, configuration parameters 520 may include one or more of a set of wireless connectivity parameters (for example, relating to a white list maintained for analyte sensor system 308, advertisement messaging, connection models, operating modes, etc.), a set of access control parameters (for example, relating to what types of devices can connect to analyte sensor system 308 while medicament delivery device 915a is connected to analyte sensor system 308, and/or what type of signaling such devices may exchange with analyte sensor system 308), a set of analyte data parameters (for example, relating to accuracy, security, and/or calibration etc.), a set of power control parameters, or any other parameters that may be used in system 900. As also described herein, and embodiments, system requirements 650 may include or be associated with one or more of a battery capacity of the one partner device 915, and accuracy requirement of the one partner device 915, a communication protocol to be used or supported by the one partner device 915, a regulatory or other safety requirement applicable to the one partner device 915, and an expected operational time of the one partner device 915.

In embodiments, the set of wireless connectivity parameters within configuration parameters 520 includes a condition under which the one partner device 915 is to be removed from a white list maintained for analyte sensor system 308. In embodiments, operation 932B optionally includes additional operations as illustrated by way of example in FIG. 9C. For example, FIG. 9C shows that at operation 934A, operation 932B (analyte sensor system 308 setting or causing the modification to configuration parameters 520 according to system requirement 650 of the one partner device 915) may include analyte sensor system 308 setting the condition such that the one partner device 915 is to be removed from the whitelist when a battery level of the one partner device 915 meets the threshold.

In embodiments, the set of access control parameters within configuration parameters 520 includes an advertisement structure or aspects thereof (for example, advertisement structure 622, referencing FIG. 6 and elements thereof). In embodiments, operation 932B optionally includes at operation 934A analyte sensor system 308 using DMPI 752 set or modify by the advertisement structure or aspects thereof, for example to effect a trade-off between connection reliability and power consumption.

In embodiments, the set of analyte data parameters within configuration parameters 520 includes a calibration period for analyte sensor system 308. In such embodiments, operation 932B optionally includes at operation 934C analyte sensor system 308 using DMPI 750 to set or modify the calibration period. In some cases, the calibration period may be set to zero or none. For example, the calibration period may be set in accordance with system requirements 650 related to accuracy required by the one partner device 915 in connection with the delivery of medicaments. In embodiments, the set of analyte data parameters includes a factory calibration code for analyte sensor system 308. Operation 932B may include at operation 934D analyte sensor system 308 using DMPI 7502 receive from the one partner device 915 an indication to use the factory calibration code, according to system requirements 650 of the one partner device 915.

With further reference to FIG. 9C, in embodiments, the set of wireless connectivity parameters within configuration parameters 520 includes settings stored in server 920b (or for example server system 334a and/or 334b, with reference to FIG. 8). In such embodiments, operation 932B may include at operation 934E analyte sensor system 308 using DMPI 750 to configure analyte sensor system 308 to use services provided via server 920b (or server system 334a and/or 334b). To illustrate, configuration parameters 520 may be set/modified in order to enable analyte sensor system 308 to support the services. For example, where analyte sensor system 308 may not have a direct connection to WAN 904, such services may be provided using an intermediate device connected to WAN 904, such as for example mobile phone 910a.

Operation 932B optionally includes at operation 934F analyte sensor system 308 using DMPI 752 configure analyte sensor system 308 to transmit diabetes management feedback to one or more display devices 910, 910' connected to or in range of analyte sensor system 308. Operation 934F is executed in response to the services provided via server 920b, in certain embodiments. Diabetes management feedback may include, by way of example, direction or instruction relating to a user's health or actions that may affect analyte levels (for example insulin levels) within the user. Such direction or instruction may be provided by the user's health cover provider, friend, or family member, etc., connected, at least indirectly, to analyte sensor system 308 via at least WAN 904. At operation 934G, if the services provided via remote server 920b become unavailable, analyte sensor system 308 may use DMPI 752 configure analyte sensor system 308 to disable the use of the services and send a related notification to relevant display devices 910, 910' connected to or in range of analyte sensor system 308. In this manner individuals or entities monitoring the user via server 920b can be made aware if a disconnection occurs and take action accordingly.

FIG. 9D is an operational flow diagram illustrating various operations that may be implemented, for example, using elements shown in FIG. 9A. FIG. 9D shows operations 938A and 938B of method 936, where method 936 may involve using DMPI 750 (with reference by way of example to FIG. 10A) to configure wireless communications among analyte sensor system 308 and one or more of display devices 910, 910' and/or partner devices 915. The operations of method 936 may be used advantageously to implement a flexible and adaptable system wherein different partner devices from different manufacturers may be accommodated through the use of a configurable diabetes management partner interface.

As shown in FIG. 9D, method 936 includes at operation 938A analyte sensor system 308 enabling a first wireless signal communication path. The first wireless communication signal path is between analyte sensor system 308 and one of display devices 910, 910', where here for illustration purposes mobile phone 910a (and, for example link 906g) will be discussed. Nevertheless, it should be appreciated that method 936 may include enabling the first wireless signal communication path between analyte sensor system 308 and any of display devices 910, 910'. As further illustrated at operation 938A also, for the first wireless communication path, analyte sensor system 308 provides mobile phone 910a with a first degree of access or control over analyte sensor system 308. For example, in some cases the first degree of access or control can allow mobile phone 910a to send command control signaling to analyte sensor system 308. In other cases, for example depending on the operation mode that is implemented, the first degree access or control may not allow mobile phone to send command control signaling.

Method 936 also includes, at operation 938B, analyte sensor system 308 enabling a second wireless communication path. The second wireless communication path is between analyte sensor system 308 and one of partner devices 915. Analyte sensor system 308 enabling the second wireless communication path per operation 938B also includes causing a modification to the first degree of access or control in order to implement a second degree of access or control according to system requirements 650 of the one partner device 915. The modification is caused in response to input received from the one partner device 915 via DMPI 750. My way of example analyte sensor system 308 may receive the input from the one partner device 915, and in response thereto use DMPI 752 modify configuration parameters 520 and thereby modify the first degree of access or control.

In embodiments, operation 938B optionally includes additional operations as illustrated by way of example in FIG. 9E. For example, as shown in FIG. 9E, operation 938B may include operation 942A. According to operation 942A, causing the modification to the first degree of access or control, in connection with operation 938B, may include using DMPI 750 to set or change configuration parameters 520 implemented by analyte sensor system 308, in accordance with system requirements 650 of the one partner device 915. In embodiments configuration parameters 520 include one or more of access control parameters for display devices 910, 910' (e.g., mobile phone 910a) and/or partner devices 915 (e.g., medicament delivery device 915a), accuracy or calibration parameters for analyte sensor system 308, and wireless communication parameters for communications to be exchanged between/among analyte sensor system 308 and one or more display devices 910, 910' and partner devices 915.

FIG. 9F shows that operation 942A may, in example implementations, include operations 946A to 946C. Accordingly, in embodiments of method 936, operation 942A (using DMPI 750 to set or change configuration parameters 520) optionally includes granting to the one partner device 915 permission to configure the accuracy or calibration parameters for analyte sensor system 308, mentioned above, in accordance with system requirements 650. Additionally operation 942A may include at operation 946B revoking from, for example, mobile phone 910a permission to configure the accuracy or calibration parameters for analyte sensor 308. For example such permission may be revoked in accordance with certain operating modes described herein.

In embodiments, the access control parameters include a whitelist for devices connectable to analyte sensor system 308, for example partner devices 915 and/or display devices 910, 910'. In some such embodiments at operation 946C using DMPI 750 to set or change configuration parameters 520, per operation 942A of method 936, includes setting or modifying an amount of time the one partner device 915 is to remain on the whitelist before being removed from the whitelist.

FIG. 9J is an operational flow diagram illustrating various operations that may be implemented, for example, using elements shown in FIG. 9A. FIG. 9J shows operations 986A through 986M that may be included in embodiments of method 984, where method 984 may involve using DMPI 750 (with reference by way of example to FIG. 10A) to facilitate the exchange of wireless communications with analyte sensor system 308. The operations of method 984 may be used advantageously to implement a flexible and adaptable system wherein different partner devices from different manufacturers may be accommodated through the use of a configurable diabetes management partner interface.

As shown in FIG. 9J, method 984 includes at operation 986A using DMPI 752 establish a first connection between analyte sensor system 308 and a first partner device (for example purposes only, medicament delivery device 915a will be referred to in connection with the first partner device). At operation 986B, method 984 includes analyte sensor system 308 providing medicament delivery device 915a with access to configuration parameters 520 (referencing FIG. 3C, by way of example) via DMPI 750. At operation 986C, method 984 includes setting or causing a first modification to configuration parameters 520 in response to input received from medicament delivery device 915a via DMPI 750. By way of example, medicament delivery device 915a may send the signal received as input at analyte sensor system 308 using link 906d (referencing FIG. 9A for example). Setting or causing the first modification is done according to system requirements 650 of medicament device 915a. At operation 986D, method 984 includes using DMPI 750 to establish a second connection between analyte sensor system 308 and a second partner device (for example purposes only, insulin pen 915d will be referred to in connection with second partner device). In embodiments, using DMPI 750 to establish the second connection occurs after the first connection has been terminated. At operation 986E, method 984 includes analyte sensor system 308 providing insulin pen 915d with access to configuration parameters 520 via DMPI 750. At operation 986F, method 948 additionally includes causing a second modification to configuration parameters 520 in response to input received from insulin pen 915d via DMPI 750. By way of example insulin pen 915d may send the signal received as input at analyte sensor system 308 using link 906j. Causing the second modification is done according to system requirements 650 of insulin pen 915d.

In embodiments, method 984 may further include at operation 986G, responsive to analyte sensor system 308 receiving identification information for a third partner device (for example purposes only, first insulin pump 915b will be referred to in connection with the third partner device), using DMPI 750 to attempt to establish a third connection between analyte sensor system 308 and first insulin pump 915b. In some cases, the identification information for first insulin pump 915b is stored in server 920b (or, for example, server system 334a and/or 334b, with reference to FIG. 8). The identification information may indicate whether first insulin pump 915b is authorized to communicate with analyte sensor system 308. In embodiments, as shown by way of example in FIG. 9K, analyte sensor system 308 receiving the identification information for first insulin pump 915b in connection with operation 986G includes at operation 990 in on it sensor system 308 receiving the identification information from one of display devices 910 (for example, mobile phone 910a) that received the identification information from server 920b (or, for example, server system 334a and/or 334b, with reference to FIG. 8).

Referring back to FIG. 9J, embodiments of method 984 may additionally include at operation 986H, responsive to analyte sensor system 308 receiving the identification information for first insulin pump 915b, using the identification information to determine whether first insulin pump 915b is authorized to communicate with analyte sensor system. At operation 986J, method 984 may include, responsive to determining that first insulin pump 915b is not authorized to communicate with analyte sensor system 308, denying the attempt to establish the third connection between analyte sensor system 308 and first insulin pump 915b. At operation 986K, method 984 may include, responsive to determining that first insulin pump 915b is authorized to communicate with analyte sensor system 308, using DMPI 750 to establish the third connection between analyte sensor system 308 and first insulin pump 915b.

In example implementations, determining that first insulin pump 915b is not authorized to communicate with analyte sensor system 308 (e.g., in connection with operation 986J) occurs at a first time, determining that first insulin pump 915b is authorized to communicate with analyte sensor system 308 (e.g., in connection with operation 986K) occurs at a second time, and the identification information for first insulin pump 915b is updated at server 920b between the first time in the second time. That is, for example, between the first and second time first insulin pump 915b may have been authorized to communicate with analyte sensor system 308 through updated identification information received at the cloud. One of skill in the art upon studying the present disclosure will appreciate that identification information may be stored in any of the elements shown in system 900 and updated, such that authorization for partner devices 915 and/or display devices 910, 910' may be provided and/or controlled via PAN 902 and/or WAN 904 and elements interconnected therein as shown in FIG. 9A.

In embodiments, method 984 further includes at operation 986L, responsive to establishing the third connection between analyte center system 308 and first insulin pump 915b, causing a third modification to configuration parameters 520 in response to input received from first insulin pump 915b via DMPI 750. By way of example first insulin pump 915b may send the signal received as input at analyte sensor system 308 using link 906h. Causing the third modification is done according to system requirements 650 of first insulin pump 915*b*. In some cases, system requirements 650 of first insulin pump 915*b* are stored in server 920*b* (or, for example, server system 334*a* and/or 334*b*, with reference to FIG. 8). In some such cases, method 984 may further include at operation 986M causing a fourth modification to configuration parameters 520 in response to input received via DMPI 750 where the fourth modification is done according to an updated version of system requirements 650 of first insulin pump 915*b* stored at server 920*b*. That is, for example according to embodiments of the present disclosure, system requirements 650 for partner devices 915 may be updated dynamically via cloud connected mechanisms, and/or using any of the other elements interconnected in system 900 via PAN 902 and/or WAN 904 or the like.

Certain aspects that may be involved with interfacing analyte sensor system 308 with additional partner devices 915 using DMPI 750 will now be described. As described above, partner devices 915 may include insulin pen 915*d*. Unlike automated medicament delivery devices, such as first and second insulin pumps 915*b* and 915*c*, insulin pen 915*d* typically uses manual intervention in order to deliver insulin. As a result, in embodiments, some of the concerns expressed herein regarding the automatic delivery of medicaments, including below in connection with operating modes, may not apply. Such concerns may, for example, relate to the effect of interference on the accuracy/precision of medicaments that are delivered.

In embodiments, as discussed above, insulin pen 915*d* can determine bolus values the user has calculated and/or how much insulin was delivered. For example, a bolus calculator can be used in conjunction with insulin pen 915*d*. Such a bolus calculator could be implemented on mobile phone 910*a* and use analyte data received from analyte sensor system 308 and manual entry from a carbohydrate counter. Using this information, the bolus calculator may provide a suggestion of how much insulin to dose. This information could be displayed on mobile phone 910*a*, or the information could be transmitted to insulin pen 915*d*. Where insulin pen 915*d* includes a display, the transmitted information can be displayed to the user using the display of insulin pen 915*d*. The user may then approve the dosage suggestion or may adjust the calculated dosage. Once the user administers a dose of insulin using insulin pen 915*d*, dosage related information may be sent back to analyte sensor system 308 and/or mobile phone 910*a*, such that insulin on board may be tracked. Additionally or alternatively, the user may manually enter dosage information into analyte sensor system 308 and/or mobile phone 910*a*, such that insulin on board may be tracked.

Where insulin pen 915*d* includes a display and/or other input/output functions/mechanisms, insulin pen 915*d* may be more amenable to direct communication with analyte sensor system 308. By way of example, analyte sensor system 308 may or may not add insulin pen 915*d* to a white list, may set or modify configuration parameters 520 responsive to system requirements 650 of insulin pen 915*d*, etc. Moreover, analyte data, EGV, and/or insulin related data may be displayed on insulin pen 915*d*. Further, calibrations could be entered directly into insulin pen 915*d*. In terms of the bolus calculator, where insulin pen 915*d* includes a display, the bolus calculator may more effectively be implemented on insulin pen 915*d*, and likewise a decision supporting module for the bolus calculator may be implemented on insulin pen 915*d* more easily. In embodiments, the piconet arrangement of system 900 may be adaptive in such a way that direct communication between analyte sensor system 308 and insulin pen 915*d* is based on the presence of mobile phone 910*a*, for example in PAN 902. For example, in some cases, mobile phone 910*a* may not be needed if insulin pen 915*d* includes a display and is connectable within PAN 902. As another feature of insulin pen 915*d* carb counting and/or meal calculation could be integrated.

Referring again to FIG. 9A, additional embodiments of system 900 may leverage the increasing number of every day devices and objects that are being connected through wireless technology. By way of example, partner devices 915 may include a smart refrigerator that detects which and how many of certain food objects and/or drinks are consumed by a given user and relays this information to mobile phone 910*a* where the information may be integrated with analyte data and/or medicament delivery data. The integration of such information may enable useful characterizations of how the user's health, including for example insulin and blood glucose levels and the like, vary as a result of the food/drink the user consumes, including characterizing such variations as a function of time. Other connected devices that may provide useful information, including for example analyte data, include gym equipment, scuba equipment, and airplanes, trains, cars, boats, or other recreational vehicles. Such devices can provide for analyte data collection under special circumstances and in an ongoing fashion that is reasonably convenient for users.

In another example, special medical circumstances or other situations involving urgency may create the need for additional features. For example where user is relying on mobile phone 910*a* to track analyte data and provide a CGM history/profile, the user's mobile phone 910*a* may be locked. It may thus be difficult for first responders to use mobile phone 910*a* to get insight into the user's analyte-related information. Embodiments of the present disclosure include providing an interface that enables access to certain information in special circumstances without unlocking mobile phone 910*a*. For example, DMPI 750 may be configured to receive a special key or override signal reserved for first responders such as police, medical professionals, caregivers etc. In some cases, an override mode may be enabled based on geographical location, such that for example, when a user enters a hospital the user's analyte data may be accessed without unlocking mobile phone 910*a*. It should be appreciated that these features may be applied to other display devices 910, 910' and/or partner devices 915.

In some cases, sensor 10 may be adapted to gather information on analytes related to muscle fatigue. Analyte data may then be provided to the user to help the user avoid becoming overly fatigued. This may be useful to, for example, athletes, military personnel, etc. In some cases, sensor 10 may be adapted to gather information on analytes related to alcohol consumption. The analyte data may then be used to prevent drunk driving. For example, analyte sensor system 308 may signal the user's vehicle to enforce security measures that prevent the user from operating the vehicle and/or to simply warn the user or other occupants of the vehicle that the users blood alcohol concentration exceeds predetermined levels.

J. Integration/Coordination of Alerts

In some embodiments, the alerts and alarms and/or notification that are generated in various devices in system 900, for example, may be coordinated to notify users more efficiently. Here, the coordination and integration of alerts and alarms is discussed more particularly referencing FIG. 9A and the example context of system 900. In the context of system 900, a problem or issue may occur where any number of display devices 910, 910', partner devices 915, and so forth are connectable to analyte sensor system 308 and/or medicament delivery device 915a. More specifically, in the context of system 900 there may be situations in which, due to the number of devices being used, there may be many potential combinations of alarms that may be triggered (e.g., related to analyte data, medicament data, battery levels, diagnostics, device status, etc.), some of which may be redundant and/or annoying and/or unnecessary. As such, when display devices 910, 910' and/or partner devices 915 are connected in system 900, in some cases, users may not want to receive multiple alarms on each of the devices triggered by the same event (e.g., Hypoglycemia). By way of example, analyte sensor application 425a that may run in mobile phone 910a may trigger an alarm when a user's glucose level is low. Additionally, upon receiving analyte data, medicament delivery device 915a and/or application 625 running thereon may trigger an alarm based on the users glucose level. In certain situations the triggering of both alarms is unnecessary and potentially inefficient, redundant, or undesirable. Here, it should be noted that where medicament delivery device 915a delivers medicaments automatically, no analyte related alerts should be necessary. Thus, to a certain extent the alert describes here may be more useful when the delivery of medicaments is not automatic.

Accordingly, embodiments of the present disclosure, including for example with respect to system 900, involve the intelligent coordination of alerts. With respect to system 900, the alerts may be coordinated across and based on the configuration of capital PAN 902 and WAN 904. At a high level, the coordination of alerts may be facilitated based on user input, based on system requirements 650 of partner devices 915, etc. In terms or alert coordination based on user input, the user may also configure all alerts for display devices 910, 910' and/or partner devices 915 etc., for example, through user interface 435, analyte sensor application 425a, and/or partner device application 425b (referencing FIG. 4). The user can use user interface 435 of mobile phone 910a, for example, to configure how alerts are set and provided on different display devices 910, 910' and/or partner devices 915. Any device shown in FIG. 9A may be used for coordinating alerts based on user input.

For example, assuming alerts are enabled at both mobile phone 910a and medicament delivery device 915a, and further assuming that additional display devices 910, 910' are in use or may be in use, the user may first navigate, e.g., sensor application 425a to select a certain display device 910, 910' for primary user interaction. This could also include, in some cases specifying a hierarchy of user preferences for display devices 910, 910'. By way of example, if sensor application 425a running on mobile phone 910a is selected as the primary interaction means, all alerts related to analytes, and most if not all alerts related to medicament delivery device 915a may issue via application 425a, at least as a first line of defense. Of course, the user's selection can be modified if, for example, the primary user interaction device becomes inoperable. For example a selected secondary device may be shifted to become the primary interaction means and/or a secondary device may be chosen automatically from in-range devices. Additionally, a fallback hierarchy may be established based on user input, a predetermined scheme, etc.

In embodiments, if the user does desire to employ multiple devices for alerts the user can select a sequence of alerts in terms of which devices the alert should be triggered on in which order, as well as what type of alert may be used for particular device and system 900. Alerts can also be configured as a function of time or as a function of events, such that for example at night, during a movie, during a moot meeting, alerts may be haptic. Or a heavy sleeper may want to configure alerts to be increased in volume during nighttime.

In some cases, to provide alerts more efficiently, escalating alerts may be implemented. For example, an alert may be provided as a first measure at mobile phone 910a and/or wearable device 910c. Then, if the alert is not acknowledged, the alert may be provided at medicament delivery device 915a. Additionally, alerts may change in type and/or intensity during the escalation process. If not acknowledged by a certain point, the alert may be propagated to entities or individuals monitoring the user (e.g., via server 920b) and/or emergency services providers.

Embodiments, partner devices 915 may govern the coordination of alerts. In some example situations, alerts may be controlled via configuration parameters 520. For example if certain alert characteristics are defined in system requirements 650 of medicament delivery device 915a, such alert characteristics may be implemented in system 900 by medicament delivery device 915a using DMPI 752 sat configuration parameters 520 accordingly.

In embodiments involving the implementation of medicament delivery device 915a as a pump (e.g., an insulin pump), special considerations may be made with respect to alerts. For example, certain pump-specific faults (e.g., undetected cannula problems) may result in medicaments not being delivered as expected. Hence, a user may experience, for example, hypoglycemia or may even develop ketones. Additional pump-specific faults may involve battery failure, drainage, or other mechanical failures.

Accordingly, embodiments of the present disclosure involve the configuration of alerts triggered by pump-specific faults. By way of example, where the user is relying on a certain remote device (e.g., display device 910, 910' etc.) connected to medicament delivery device 915a under the intermittent connection model, four pump specific faults, it may be desirable to notify the user of the alert without waiting for the next transmission opportunity. Thus, medicament delivery device 915a may temporarily override the setting of the remote device has the sole or even primary device for providing alerts in order to provide the alert to the user more quickly. Alternatively, connecting to the medicament delivery device 915a using the continuous connection model may be a way to avoid this issue.

In addition, for any fault or error related issues with medicament delivery device 915a, diagnostic information may be provided to analyte sensor system 308. In embodiments, such diagnostic information can be shared with analyte sensor system 308 using DMPI 750. For example, configuration parameters 520 may include a diagnostics field or array that may be populated with such information. The diagnostic information could then be propagated to other devices in system 900, including mobile phone 910a, mirror 910d, etc. For example, such information may be propagated via mesh networking, a series of network of connected devices, including common-place devices, and/or machine-to-machine transactions, and the like.

In certain embodiments, pump-specific faults may be difficult to detect. As an example, if there is only a partial cannula occlusion, and alarm may not be triggered at medicament delivery device 915a (e.g., no problem may detected due to the partial nature of the occlusion). Such problems may arise, because, for example, each time an infusion set is changed, there is a risk that the infusion site or cannula does not have a proper insulin absorption or is completely or partially occluded. Occlusions, particularly partial occlusions, for example involving a kink in cannula, may be difficult to detect. This is problematic because undetected cannula problems may lead to hypoglycemia and even ketoacidosis, which can be life-threatening. As such, standards of care can be implemented to monitor for such difficult to detect problems, including monitoring insulin delivery mechanisms. But periodic monitoring may be burdensome and/or expensive. Additional issues may arise where a partial occlusion may cause the user's blood glucose level to rise, but due to other factors the user may not be able to detect the reason behind the blood glucose level change (for example, the user may suspect that the book level change has resulted from the user's food consumption).

Accordingly, embodiments of the present disclosure involve medicament delivery device 915a providing information related to the functionality of medicament delivery device 915a via analyte sensor application 425a, analyte sensor system 308, and/or other means in system 900. Such information may include, by way of example, reservoir change information, e.g., pump rewind time, pump prime time, cannula fill time and/or amount. Such information may include, for example fluid pressure metrics or other measures that are used to generate occlusion alerts, e.g., a combination of cannula fills, reservoir changes, and pump primes, which may be used to determine when part of an infusion set may have been changed. Additionally, fluid pressure may be used to further develop an individualized characterization for the user that can dictate when alarms may be appropriate vis-à-vis infusion set issues.

In embodiments the above information may be combined with analyte data in order to assist in distinguishing between blood glucose level changes that result from infusion set issues and such changes that may result from the user's consumption of sugar, for example. By way of illustration, the analyte data may indicate that the change in blood glucose level is related to the user's consumption of sugar whereas the infusion set information can be used to identify the partial occlusion issue.

K. Operating Modes

With further reference to FIG. 9A, embodiments of the present disclosure related to various operating modes that may be implemented in connection with system 900 will now be described. At a high level, it should be appreciated that different operating modes may be implemented depending upon, for example, whether any partner devices 915 are connecting to analyte sensor system 308 and whether such partner devices are adapted to deliver medicaments to a user are available for connection with analyte sensor system 308, and/or in some cases depending further upon system requirements 650 of partner devices 915. In example deployments, a medicament delivery operating mode may be specific to a configuration of system 900 that utilizes at least one partner device 915 adapted to deliver medicaments to a user (e.g., medicament delivery device 915a) and does not utilize any display devices 910, 910'. As another example, a display operating mode may be specific to a configuration of system 900 that does not utilize at least one partner device 915 adapted to deliver medicaments to a user. A hybrid operating mode may be specific to a configuration of system 900 that utilizes at least one partner device 915 adapted to deliver medicaments to a user and that utilizes at least one display device 910, 910'. Features for each of these operating modes will now be discussed.

In embodiments, the medicament delivery operating mode may be employed in order to accommodate system requirements 650 of medicament delivery device 915a that is adapted to delivery medicaments to a user (e.g., an insulin pump or other automatic medicament delivery device), where system requirements 650 are such that medicament delivery device 915a should have a dedicated connection with analyte sensor system 908. For example, such system requirements 650 may indicate that medicament delivery device 915a is not relatively robust. In the medicament delivery operating mode, remote devices other than medicament delivery device 915a (e.g., display devices 910, 910') may be blacklisted from connecting to analyte sensor system 908.

By way of example, medicament delivery device 915a may implement the medicament delivery operating mode by using DMPI 750 to access and set/modify configuration parameters 520, and in some cases specifically wireless connectivity parameters of configuration parameters 520, to remove all remote devices (e.g., display devices 910, 910' and other partner devices 915) from the whitelist. Additionally or alternatively, medicament delivery device 915a may use DMPI 750 to set access control parameters of configuration parameters 520 such that analyte sensor system 908 accepts connection requests from medicament delivery device 915a only. For example, medicament delivery device 915a may include a flag or other information in a packet sent with a connection request sent to analyte sensor system 308, where the flag or other information indicates the connection request originated from medicament delivery device 915a or a class of devices that includes medicament delivery device 915a.

The medicament delivery operating mode may be entered automatically in some cases. For example, a connection may be established between medicament delivery device 915a and analyte sensor system 308, following which medicament delivery device 915a may be registered with analyte sensor system 308 and whitelisted. Thereupon, analyte sensor system may enter into and operate in the medicament delivery operating mode. This operating mode may be changed subsequently, for example if system requirements 650 of medicament delivery device 915a can support the hybrid operating mode, or for example if medicament delivery devices 915a is removed from the whitelist.

According to embodiments, entering the medicament delivery operating mode may require authentication of medicament delivery device 915a. For example, in some cases, the medicament delivery operating mode may be enabled using analyte sensor application 425b, referencing FIG. 4. A user wishing to use medicament delivery device 915a may download and/or install analyte sensor application 425a and/or partner device application 425b. Then partner device application 425b may authenticate itself and/or medicament delivery device 915a for communication with analyte sensor application 425a. This authentication may be by exchange hash values or other means. Following authentication, analyte sensor system 308 may enter the medicament delivery operating mode medicament. In some cases, user input (including, e.g., password, fingerprint, or facial recognition input) may be solicited to authorize entering the medicament delivery operating mode.

In embodiments, when operating in the medicament delivery operating mode, analyte sensor system 308 may include in advertisement messages a mode indicator that indicates to remote devices receiving the advertisement messages that analyte sensor system 308 is operating in the medicament delivery mode. The mode indicator may be encrypted. In some cases, upon receiving such advertisement messages, the remote devices other than medicament delivery device 915a may be adapted to detect from the mode indicator that analyte sensor system 908 is operating in medicament delivery mode and therefore such remote devices may ignore the advertisement messages. In some cases, upon receiving such advertisement messages, the remote devices other than medicament delivery device 915a may respond with a connection request, but analyte sensor system 308 may be adapted to ignore the connection request upon detecting that the connection request did not originate from medicament delivery device 915a (or a class of devices that includes medicament delivery device 915a).

Additional techniques may be employed for preventing remote devices other than medicament delivery device 915a from communicating with analyte sensor system 308. For example, medicament delivery device 915a may use DMPI 750 to set configuration parameters 520 of analyte sensor system 308, and by way of specific example may set wireless connectivity parameters thereof, such that medicament delivery device 915a may occupy all the available advertisement slots. In some cases, this may involve medicament delivery device 915a using DMPI 750 to modify configuration parameters 520 such that there is only one advertisement slot and that slot is allocated to medicament delivery device 915a. Or one slot may be occupied by medicament delivery device 915a while the other slot may be occupied by controller 645. As such, it may be the case that no other remote device will be able to connect with analyte sensor system 308.

More generally, in connection with operating in the medicament delivery operating mode (and/or the hybrid mode), analyte sensor system 308 may give medicament delivery device 915a permission to configure the whitelist maintained by analyte sensor system 308, including age off (e.g., time out) rules for other devices (e.g., display devices 910, 910') or classes of devices.

In embodiments, the display operating mode can be used when no partner devices 915 adapted to deliver medicaments to a user (e.g., insulin pumps 915b, 915c or other automatic medicament delivery device, insulin pen 915d, or more generally medicament delivery device 915a) are utilized within system 900. Typically, the display operating mode may be less restrictive than the medicament delivery operating mode, because in the display operating mode, system requirements 650 of medicament delivery device 915a are not imposed upon the operation of analyte sensor system 308. Thus, in example implementations of the display operating mode, various display devices 910, 910' may establish connections and receive/send communications related to analyte data, control, etc.

In embodiments, where system 900 has been operating in medicament delivery mode, but medicament delivery device 915a stops communicating with analyte sensor system 308 (e.g., because the user powered down or detached medicament delivery device 915a, or the device otherwise stopped functioning), analyte sensor system 308 may remove medicament delivery device 915a from the whitelist and fall back to display operating mode (assuming no other medicament delivery device 915a is being utilized). This fall back may involve restoring configuration parameters 520 to a state that existed prior to configuration parameters 520 being set/modified by medicament delivery device 915a using DMPI 750.

In embodiments, the hybrid operating mode may be used, for example in system 900, where it is feasible to accommodate system requirements 650 of medicament delivery device 915a that is adapted to deliver medicaments to a user (e.g., an insulin pump or other automatic medicament delivery device), while at the same time providing other remote devices (e.g., display devices 910, 910') with at least the opportunity to receive analyte data from analyte sensor system 308 (in addition to medicament delivery device 915a receiving the analyte data). For example, where medicament delivery device 915a may be sufficiently robust to allow remote devices other than medicament delivery device 915a to receive analyte data in a display only state, however, medicament delivery device 915a may not be robust enough to deal with such remote devices additionally sending command/control signaling to analyte sensor system 308.

Thus, in this example of the hybrid operating mode, while display devices 910, 910' may be able to receive analyte data (e.g., using communication session 720, 740, or 760, with reference to FIGS. 7A-7C), such display devices 910, 910' may not send calibration commands to analyte sensor system 308. In this manner, system 900 may operate in accordance with system requirements 650 of medicament delivery device 915a, while at the same time allowing display devices 910, 910' to provide, for example, a trend graph to the user and/or allowing analyte data to be provided to be monitored using a remote devices connected via WAN 904 (e.g., by a medical professional or friend or family member of the user). Displayable analyte data may be encrypted for communication to various devices via PAN 902 and/or WAN 904. In embodiments, alerts may be controlled and/or somewhat limited vis-à-vis display devices 910, 910'. For example, alerts may be channeled through medicament delivery device 915a instead of being provided from all devices receiving analyte data from analyte sensor system 308.

In embodiments of the hybrid operating mode, system requirements 650 may reflect that medicament delivery device 915a is relatively more robust, and thus remote devices other than medicament delivery device 915a may be allowed to communicate with and send command/control messages to analyte sensor system 308, and/or may be able to access accuracy or calibration parameters, start/stop events, etc. relative to analyte sensor system 308. For example, system requirements 650 may indicate that medicament delivery device 915a is sufficiently robust to allow remote devices other than medicament delivery device 915a to not only receive analyte data but also to send command/control signaling to analyte sensor system 308 without disturbing the operation of medicament delivery device 915a. Thus, in this example of the hybrid operating mode, display devices 910, 910' may be able to send calibration commands to analyte sensor system 308, and system 900 may nevertheless operate in accordance with system requirements 650 of medicament delivery device 915a.

The hybrid operating mode may be implemented using DMPI 750 to set configuration parameters 520 of analyte sensor system 308, for example, to allow remote devices other than medicament delivery device 915a to connect to analyte sensor system 308 and/or receive analyte data therefrom (e.g., in a display only state for such remote devices), and in some cases may allow such remote devices to send command/control signaling to analyte sensor system 308. For example, this may be accomplished through medicament delivery device 915a using DMPI 750 to set the access and control parameters described above. Additionally, DMPI 750 may be used to set the wireless connectivity parameters described above in order to, for example, send analyte data to the remote devices where the analyte data can be included in advertisement messages transmitted (e.g., broadcasted) by analyte display device 308 (for example per communication session 760 with reference to FIG. 7C). The hybrid mode, in embodiments, may require authentication (e.g., as described above for the medicament delivery mode) before being employed.

In some instances, the user may control which version of the hybrid operating mode is employed—e.g., whether devices other than medicament delivery device 915a may send control/command signaling relating to analyte data. For example, user interface 435 of mobile phone 910a may provide a GUI that allows the user to select between versions of the hybrid operating mode. In some cases, the GUI may additionally provide the user with warnings, recommendations, and/or system performance implications associated with choosing one version of the hybrid operating mode versus another version. It is also contemplated that other operating modes (e.g., the medicament delivery mode, display only mode) as described above, may also be user-selectable, for example, via user interface 435.

As alluded to above, embodiments of the present disclosure include changing between the above-described operating modes. For example, if the user decides to stop using medicament delivery device 915a, or if medicament delivery device 915a experiences battery failure or some other malfunction, then system 900 may transition from employing the medicament delivery operating mode or the hybrid operating mode to the display operating mode. Or, for example, the transition among modes may simply be based on user preference as indicated, for example, via user interface 435 of display device 910, 910'. Transitioning between operation modes may involve sending a mode command.

As another example, system 900 may transition from medicament delivery mode to hybrid mode if the user is switching/replacing medicament delivery device 915a. To illustrate, if the user's insulin pump is broken or otherwise needs to be replaced, the user may manually initiate a transition from medicament delivery mode to hybrid mode before disengaging the insulin pump. In this manner, even when the insulin pump is removed, display devices 910, 910' may continue to receive analyte data from analyte sensor system 308 and provide such data to the user. Then, once the replacement insulin pump is installed, the system may transition back to medicament delivery mode. The transition back to the medicament delivery mode may occur automatically, without user intervention, for example in response to analyte sensor system 308 detecting a connection request from the replacement insulin pump. In this situation, it may not be necessary to transition to the display operating mode when the insulin pump is removed, because of the relatively short time during which the insulin pump is expected to be out of commission.

In embodiments, one or more display devices 910, 910' may recommend to the user that the operating mode be transitioned. For example, the presence of medicament delivery device 915a may be detected by analyte sensor system 308 (e.g., via a connection request) and/or one or more display devices 910, 910', and as a result, a recommendation may be provided to the user to transition to the medicament delivery or hybrid operating mode. In embodiments, such transitions may be triggered and/or occur automatically upon detecting the presence and/or system requirements 650 or medicament delivery device 915a. For example, system requirements 650 of medicament delivery device 915a may be shared with analyte sensor system 308 and/or display devices 910, 910', and upon parsing system requirements 650, it may be determined that a particular operating mode (e.g., medicament delivery mode) is necessary to accommodate system requirements 650 or that a particular operating mode may be more suitable. Transition schemes between operating modes for various scenarios may in embodiments be pre-programmed to default configurations, any of which be implemented.

A specific example of transitioning among operating modes will now be provided. In this specific example, system 900 has been operating in display operating mode, with the user monitoring analyte data via mobile phone 910a. In this example, a direct connection between medicament delivery device 915a and analyte sensor system 308 will be established (e.g., using link 906d). On mobile phone 910a, the user may enable the medicament delivery operating mode, for example, in anticipation of setting up medicament delivery device 915a. In response, mobile phone 910a may signal a mode switch to analyte sensor system 308 (e.g., using link 906g). A connection may then be established between analyte sensor system 308 and medicament delivery device 915a (e.g., by the process described in connection with FIG. 7A or FIG. 7B). In some cases, mobile phone 910a may remain connected to analyte sensor system 308. This may provide redundancy during the transition process.

Medicament delivery device 915a may then use DMPI 750 to set/modify configuration parameters 520 in accordance with system requirements 650. For example, medicament delivery device 915a may provide system requirements 650 to analyte sensor system 308 so that analyte sensor system 308 can modify configuration parameters 520. Additional information may be assessed in setting the configuration parameters 520, including for example, an age off time for medicament delivery device 915a, how long a sensor session will last (e.g., to coincide with insulin alerts), and the types of alerts that will be used and how they will propagate and be acknowledge through PAN 902/WAN 904. Upon terminating the use of medicament delivery device 915a, the user can so indicate via mobile phone 910a, such that mobile phone 910a send another mode switch signal to analyte sensor system 308 to remove medicament delivery device 915a from the whitelist and modify configuration parameters 520 to revert to their previous values. The above example may be modified such that medicament delivery device 915a does not directly connect to analyte sensor system 308 but rather connects thereto via mobile phone 910a via links 916 and 906g. It should also appreciated that mode switches can generally be employed in an adaptive manner and/or based on user input, in order to accommodate changes to the configuration of system 900, including for example changes relating to what devices are connectable to analyte sensor system 308 and/or are present within PAN 902 and/or WAN 904.

At this juncture, embodiments of methods and features that may be implemented in connection with FIG. 9A and operating modes that may be implemented in relation thereto (by way of example) will now be described with reference, by way of example to FIGS. 9G, 9H, and 9L through 9S. FIG. 9G is an operational flow diagram illustrating various operations that may be implemented, for example, by elements shown in FIG. 9A. FIG. 9G shows operations 950A through 950M that may be implemented in connection with embodiments of method 948, where method 948 may involve using DMPI 750 (with reference by way of example to FIG. 10A) four analyte sensor system 3082 control wireless communications among analyte sensor system 308 and one or more remote devices connectable to analyte sensor system 308, where the one or more remote devices include one of display devices 910, 910' and one of partner devices 915. For purposes of illustration only, reference will be made to FIG. 9A and, for display devices 910, 910', mobile phone 910*a* will be referenced for the one display device 910, 910', and for partner devices 915, medicament delivery device 915*a* will be referenced for partner devices 915, unless noted otherwise. It should be appreciated, however that these specific examples of display devices 910, 910' and partner devices 915 are nonlimiting as to the scope of the present disclosure. The operations of method 948 may be used advantageously to implement a flexible and adaptable system wherein different partner devices from different manufacturers may be accommodated through the use of a configurable diabetes management partner interface, including for example to implement various operating modes, as described herein.

As shown in FIG. 9G, method 948 includes at operation 950A analyte sensor system 308 determining whether a connection request received from one of the remote devices originated from a partner class within the one or more remote devices. In the context of method 948, the remote devices in the partner class are adapted to provide medicaments. The partner class includes medicament delivery device 915*a*.

At operation 950B, if the connection request originated from the partner class, then method 948 includes DMPI 750 enabling selection of an operating mode corresponding to the partner class. In order to support system requirements 650 of medicament delivery device 915*a* (for example referencing FIG. 5B), the operating mode corresponding to the partner class uses a set of configuration parameters 520 (for example referencing FIG. 3C) for the partner class. The set of configuration parameters 520 are maintained within analyte sensor system 308.

At operation 950C, method 948 optionally includes exchanging the wireless communications with at least one of the remote devices using the operating mode corresponding to the partner class (e.g., any of display devices 910, 910' and/or partner devices 915). FIG. 9H shows additional operations that may be carried out in connection with operation 950C of method 948, according to certain embodiments. For example, at operation 954A, exchanging the wireless communications using the operating mode corresponding to the partner class per operation 950C may include transmitting a mode indicator usable by the at least one of the remote devices to determine the operating mode is selected by analyte delivery device 308. That is a mode indicator may be sent by analyte sensor system 308 to connectable devices within range to convey to such devices the operating mode being employed in connection with the use of analyte sensor system 308.

As mentioned above, the set of configuration parameters 520 that may be used to support system requirements 650 of medicament delivery device 915*a* (again, by way of example) may include one or more of access control parameters for mobile phone 910*a* or medicament delivery device 915*a*, accuracy or calibration parameters for analyte sensor system 308 and wireless communication parameters for communications to be exchanged among analyte sensor system 308 and one or more of the remote devices. In embodiments, the mode indicator referenced in connection with operation 954A is operable by analyte sensor system 308 to use DMPI 750 to deactivate access by a set of the remote devices that are not in the partner class to one or more of the access control parameters, the accuracy or calibration parameters, and the wireless communication parameters. Additionally, in embodiments access to these parameters by the set of the remote devices that are not in the partner class is activated when analyte sensor system 308 uses an operating mode corresponding to the set of remote devices not in the partner class.

With further reference to FIG. 9H, operation 954B involves modifying a white list maintained for analyte sensor system 308 in order to switch off slots for devices other than medicament delivery device 915*a*. That is, for example according to operation 954B, devices other than medicament delivery device 915*a* may be prevented from receiving and/or responding to advertisement messages transmitted by analyte sensor system 308. Operation 954C involves transmitting advertisement messages directed to only medicament delivery device 915*a* or partner device controller 645 (for example referencing FIG. 5B) that may be used in conjunction with medicament delivery device 915*a*. For example operation 954C may involve employing device-specific advertising. Alternatively or additionally, operation 954C may involve analyte sensor system 308 rejecting connection requests received in response to transmitted advertisement messages, where such connection requests are received from devices other than medicament delivery device 915*a*. In embodiments, operation 950C may include at operation 954D, responsive to a command received via DMPI 750, analyte sensor system 308 accepting connection request received from medicament delivery device 915*a* only. By way of example, a user of analyte sensor system 308 may specify (for example, using user interface 435) that only medicament delivery device 915*a* may communicate with analyte sensor system 308. As such, analyte sensor system 308 may be adapted to disregard connection requests that do not originate with medicament delivery device 915*a*.

Referring again to FIG. 9G, if at operation 950A it is determined that the connection requests did not originate from the partner class, method 948 optionally includes at operation 950D analyte sensor system 308 selecting an operation mode corresponding to a set of the remote devices that are not in the partner class. The operating mode corresponding to the set of the remote devices that are not in the partner class uses a set of configuration parameters 520 specific to the set of remote devices that are not in the partner class. That is, for example DMPI 750 may be used to adaptively configure the operation of analyte sensor system 308 and/or remote devices within system 900, such as for example display devices 910, 910' based on an assessment that the connection request was not received from partner devices 915. This may be advantageous, for example, for the reasons above described above with respect to certain partner devices 915, such as for example insulin pumps 915*b* and 915*c*, that potentially have less robust algorithms or other system requirements 650 that may not be operate optimally in an environment that includes interference from other remote devices.

Where mobile phone 910*a* is in the set of remote devices that are not in the partner class, embodiments of method 948 include at operation 950E using DMPI 750 to provide mobile phone 910*a* with access to the set of configuration parameters 520 specific to the set of remote devices that are not in the partner class. In some such embodiments, method 948 further includes at operation 950F analyte sensor system 308 setting or modifying a value for one of the set of configuration parameters 520 specific to the set of remote devices that are not in the partner class, responsive to input received from mobile phone 910*a*. That is for example according to an operating mode that may be employed where partner devices 915 are not communicating with analyte sensor system 308, other remote devices may be enabled to more freely configure certain characteristics of analyte sensor system 308 as may be facilitated using configuration parameters 520.

At operation 950G, method 948 optionally includes determining that analyte sensor system 308 has not received a wireless communication from medicament delivery device 915a for at least a predetermined amount of time. In response to such a determination, and further in response to receiving a connection request from one of the remote devices in a set of the remote devices that are not in the partner class, at operation 950H, method 948 may include analyte sensor system 308 selecting an operating mode corresponding to the set of the remote devices that are not in the partner class. The operating mode corresponding to the set of remote devices that are not in the partner class may follow a set of configuration parameters 520 specific to the set of remote devices. That is, for example, according to an operating mode that may be employed where medicament delivery device 915a has not communicated with analyte sensor system 308 for a certain amount of time, which may be predetermined, programmable, adaptable, and/or variable, analyte sensor system 308 may be adapted to employ an operating mode more tailored to display devices 910, 910', as opposed to being more tailored to medicament delivery device 915a. In this manner, the flexibility of system 900 enabled by DMPI 750 can enable system 900 to adapt and optimize according to what devices are being used in PAN 902 and/or WAN 904. Additionally, at operation 950J, medicament delivery device 915j may be removed from a whitelist for example that may be maintained for analyte sensor system 308. In some cases, it may be advantageous to remove medicament delivery device 915a from the whitelist if it is determined that medicament delivery device 915a is not communicating with analyte sensor system 308, for example to allow other devices to be whitelisted in the case that the whitelist caps the number of devices that may be whitelisted.

Embodiments of method 948 optionally includes at operation 950K analyte sensor system 308 using DMPI 750 to receive from medicament delivery device 915a a value for one of the set of configuration parameters 520. For example this value may be passed from medicament delivery device 915a to analyte sensor system 308 using link 906d. Method 948 may additionally include at operation 950L analyte sensor system 308 modifying the one configuration parameter 520 using the value received from medicament delivery device 915a. At operation 950M, method 948 may include analyte sensor system 308 sending the value for the one configuration parameter 520 to mobile phone 910a, for example using link 906g. The value may include one or more of a specified time after which medicament delivery device 915a is to be removed from a whitelist maintained for analyte sensor system 308, and a specified time after which mobile phone 910a is to be removed from the whitelist. In this manner the user of mobile phone 910a can be apprised of age off times for medicament delivery device 915a and/or mobile phone 910a, or indeed any other remote device shown in system 900.

FIG. 9L is an operational flow diagram illustrating various operations that may be implemented, for example, by elements shown in FIG. 9A. FIG. 9L shows operations 958A through 958C that may be implemented in connection with embodiments of method 956, where method 956 may involve using DMPI 750 (with reference by way of example to FIG. 10A) to allow configurability of analyte sensor system 308 that exchanges wireless communications with partner devices 915 and/or display devices 910, 910' (referencing FIG. 9A, for example). For purposes of illustration only, where appropriate, reference will be made to FIG. 9A and, for display devices 910, 910', mobile phone 910a, and for partner devices 915, medicament delivery device 915a. It should be appreciated, however that these specific examples of display devices 910, 910' and partner devices 915 are nonlimiting as to the scope of the present disclosure. The operations of method 956 may be used advantageously to implement a flexible and adaptable system wherein different partner devices from different manufacturers may be accommodated through the use of a configurable diabetes management partner interface, including for example to implement various operating modes, as described herein.

As shown in FIG. 9L, method 956 includes at operation 958A analyte sensor system 308 determining that a first connection request was sent from a remote device in a first class of remote devices. The first class of remote devices may encompass display devices 910, 910'. Thus, for example, the remote device in the first class of remote devices may be mobile phone 910a that can use link 906g to communicate with analyte sensor system 308. At operation 958B, method 956 includes analyte sensor system 308 determining that a second connection request was sent from a remote device in a second class of remote devices. The remote devices of the second class of remote devices are adapted to deliver medicaments to user. Thus, for example, the remote device in the second class of remote devices may be medicament delivery device 915a. The first class of remote devices in the second class of remote devices may be defined such that none of the remote devices of the first class of remote devices belongs to the second class of remote devices and vice versa.

At operation 958C, method 956 includes analyte sensor system 308 using anyone of a plurality of operating modes. Various operating modes have or will be discussed herein, and in embodiments such operating modes may be used in connection with operation 958C. But, for purposes of illustration, specific operating modes will now be discussed in connection with embodiments of method 956 and more specifically operation 958C. According to operation 958C, a first operating mode of the plurality of operating modes is specific to a first configuration that utilizes a remote device in the second class of remote devices and does not utilize a remote device in the first class of remote devices. As such, under the first configuration, medicament delivery device 915a is connected/connecting to analyte sensor system 308 but mobile phone 910a is not connected/connecting to analyte sensor system 308. A second operating mode of the plurality of operating modes that may be used in connection with operation 958C is specific to a second configuration that does not utilize a remote device in the second class of remote devices. As such, under the second configuration, mobile phone 910a is connected/connecting to analyte sensor system 308 but neither medicament delivery device 915a nor any other partner device 915 adapted to deliver medicaments two user is connected/connecting to analyte sensor system 308. A third operating mode of the plurality of operating modes that may be used in connection with operation 958C is specific to a third configuration that utilizes a remote device in the first class of remote devices and a remote device from the second class of remote devices. As such under the third configuration, both medicament delivery device 915a and mobile phone 910a are connected/connecting to analyte sensor system 308.

FIGS. 9M, 9R, and 9S show additional operations that may be carried out in connection with operation 958C of method 956, according to certain embodiments. For example, as shown in FIG. 9M, where operation 958C involves using the first operating mode of the plurality of operating modes, operation 958C may include at operation 962A providing the remote device and the second class of remote devices authority to use DMPI 750 to modify permissions provided to the remote device in the first class of remote devices. By way of example, medicament delivery device 915a may receive authorization to modify configuration parameters 520 using DMPI 750, and more specifically such configuration parameters 520 related to permissions. In example embodiments, the permissions may be modified in order allow medicament delivery device 915a to restrict mobile device 910a's ability to control analyte data parameters (e.g., such as accuracy or calibration parameters) four analyte sensor system 308.

With further reference to FIG. 9M, where operation 958C involves using the first operating mode of the plurality of operating modes, operation 958C may include at operation 962B analyte sensor system 308 receiving from the remote device in the first class of remote devices and authentication for the remote device in the second class of remote devices to communicate with analyte sensor system 308. For example, a user may authenticate medicament delivery device 915a for communication with analyte sensor system 308, where the user grants authentication via mobile phone 910a. Additionally, where operation 958C involves using the first operating mode of the plurality of operating modes, operation 958C optionally includes at operation 962C, responsive to input received via DMPI 750 from the remote device in the second class of remote devices, analyte sensor system 308 preventing a connection with devices other than the remote device in the second class of remote devices. Thus, for example, management delivery device 915a may use DMPI 752 configure analyte sensor system 308 such that only medicament delivery device 915a is connectable to analyte sensor system 308.

FIGS. 9N, 9P, and 9Q show additional operations that may be carried out in connection with operation 962C of method 956, according to certain embodiments. For example, FIG. 9N shows that operation 962C (preventing the connection with devices other than the remote device in the second class of remote devices) may include at operation 966A using a first advertisement slot to advertise to the remote device in the second class of remote devices and may further include at operation 966B using a second advertisement slot to advertise to the remote device in the second class of remote devices or a controller for the remote device in the second class of remote devices (for example, partner device controller 645, referencing FIG. 5B). In this manner, all available advertisement slots or durations may be used to advertise for medicament delivery device 915a, such that there may be no opportunity for advertising to other remote devices such as, for example, display devices 910, 910'.

FIG. 9P shows that operation 962C (preventing the connection with devices other than the remote device in the second class of remote devices) may include at operation 970 analyte sensor system 308 using DMPI 750 to set or cause a modification to advertisement structure 622 (referencing, for example, FIG. 6) to include a single advertisement duration 614 that may be dedicated to the remote device and the second class of remote devices. As such, in embodiments, DMPI 750 may be used to set/modify configuration parameters 520 such that advertisement structure 622 includes only one advertisement slot, and that advertisement slot is used to advertise to medicament delivery device 915a. In this manner the remote devices such as, for example, display devices 910, 910' may be prevented from connecting with analyte sensor system 308, thus supporting the first operating mode according to example implementations.

FIG. 9Q shows that operation 962C (preventing the connection with devices other than the remote device in the second class of remote devices) may include at operation 974 analyte sensor system 308 accepting connection requests from only the remote device in the second class remote devices. That is, one example of how remote devices other than devices adapted to deliver medicaments to users may be prevented from connecting to analyte sensor system 308 involves rejecting connection requests that do not originate from devices adapted to deliver medicaments to users. In embodiments, one or more packets sent to analyte sensor system 308 with a connection request may identify whether or not the device sending such packets is adapted to deliver medicaments such that analyte sensor system 308 may parse the packet(s) to determine what type of device the packet, and hence in this example the connection request, originated from.

Referring back to FIG. 9M, at operation 962D, where operation 958C involves using the first operating mode of the plurality of operating modes, operation 958C optionally includes analyte sensor system 308 using input received from the remote device in the second class of remote devices via DMPI 750 to modify timeout rules associated with the remote device in the second class of remote devices. For example, medicament delivery device 915a may use DMPI 750 to modify configuration parameters 520 and modify timeout settings for medicament delivery device 915a or for that matter for display devices 910, 910' as well.

Now referencing FIG. 9R, additional operations that may be carried out in connection with operation 958C of method 956 (analyte sensor system 308 using any one of the plurality of operating modes) will now be discussed, according to certain embodiments. More specifically, FIG. 9R illustrates operations that may be carried out in connection with analyte sensor system 308 using the second operating mode of the plurality of operating modes. For example using the second operating mode, in embodiments, includes one or more of modifying a whitelist to exclude the remote device in the second class of remote devices (for example, at operation 978A), rejecting connection requests received from the remote device in the second class of remote devices (for example, at operation 978B), and advertising exclusively for remote devices in the first class of remote devices (for example, at operation 978C). Each of these operations may be used to prevent devices adapted to deliver medicaments to users from connecting to analyte sensor system 308.

FIG. 9S illustrates additional options operations that may be implemented according to embodiments of operation 958C (analyte sensor system 308 using any one of the plurality of operating modes). More specifically, FIG. 9S shows example operations that may be performed in connection with analyte sensor system 308 using the third operating mode of the plurality of operating modes. In the third operating mode of the plurality, display devices 910, 910' may receive and/or present analyte data, but may not have the ability to issue control/command signals that analyte sensor system 308 will implement, for example where such control/command signals relate to the generation of analyte data. In some cases, this version of the third operating mode may be referred to herein as a display only operating mode.

At operation 982A, operation 958C optionally includes analyte sensor system 308 receiving, via DMPI 750, an indication from the remote device in the second class of remote devices of a level of access to analyte sensor system 308 that the remote device in the first class of remote devices is to be given. For example medicament delivery device 915a may use DMPI 750 to access configuration parameters 520 and thereby manage if and how other remote devices such as display devices 910, 910' can connect within system 900, and in some cases specifically to analyte sensor system 308, and/or what level of control or access such remote devices may have within system 900, including for example what level of control/access may be available to analyte sensor system 308. At operation 982B, operation 958C may include analyte sensor system 308 using DMPI 750 to implement the level of access to analyte sensor system 308. At operation 982C, operation 958C optionally includes notifying the remote device in the first class of remote devices of the level of access. That is, for example mobile phone 910a and/or user thereof may be notified of how medicament delivery device 915a is managing the level of control provided to mobile device 910a. In embodiments, according to the level of access, the remote device in the first class of remote devices can receive analyte data from analyte sensor system 308 but cannot access accuracy or calibration parameters within configuration parameters 520 used by analyte sensor system 308 for the third operating mode. That is, for example, medicament delivery device 915a can use DMPI 750 to put this play devices 910, 910' into display only mode by altering permissions granted to display devices 910, 910' (e.g., mobile phone and 910a).

In connection with the above-described operating modes that may be used in embodiments of system 900, and with reference to FIGS. 4 and 5B, one or more of analyte sensor application 425a, partner device application 425b, and medicament delivery application 625 may provide a user with information regarding the operating mode being employed as well as further information related to the operating mode and implications regarding system 900. By way of example, analyte sensor system application 425a may obtain or track information regarding which of the medicament delivery, display, or hybrid operating modes is being used. As such, analyte sensor application 425a may present information to the user via user interface 435 that system 900 is operating in the medicament delivery operating mode. Analyte sensor application 425a may further provide information indicating that analyte sensor system 308 is in range and connectable to one or more display devices 910, 910', but that, as a result of system 900 being in medicament delivery operating mode, analyte sensor system 308 is not exchanging analyte data with such display devices 910, 910'.

In some cases, system 900 may rely on information stored, for example in analyte sensor system 308 (storage 515), display device 310 (storage 415), partner device 315 (storage 615), and/or server system 334 (storage 334b) to determine aspects of operation, such as the operating mode to be used under certain conditions, as well as authenticating and pairing remote devices. For example, a database, table, or other format of information may provide a list of authorized partner devices 915, including medicament delivery devices 915a (e.g., based on identification numbers for each device) and respective operating modes that each such partner devices 915 may support, may provide information regarding authenticating and pairing the partner devices, etc. In some cases, the stored information can act as a master directory of system requirements for a universe of partner devices 915. Such a master director may be maintained in server system 334 for example. Select information may then be downloaded to analyte sensor system 308 if, for example, particular partner devices 915 may be employed in system 900.

With respect to operating modes more generally as described herein, when transitioning among connection modes, connection modes may need to be changed as well. For example, for operating in display operating mode, two display devices 910, 910' may employ the continuous connection model. If medicament delivery device 915a is activated, however, and the operating mode is transitioned to medicament delivery mode, for example, the continuous connection model may be employed as between medicament delivery device 915a while display devices 910, 910' may use the intermittent connection model (e.g., per communication session 720) and/or the advertisement broadcast mode (e.g., per communication session 760).

L. Application Integration & Interfaces

With reference to FIG. 9A, and as discussed in connection with embodiments of the present disclosure, in some cases, a user may be using analyte sensor system 308 and also medicament delivery device 915a (e.g., an insulin pump). In embodiments, elements of the user's PAN 902 may be in connection to remote cloud services, for example provided via WAN 904. In embodiments analyte sensor application 425a (referencing FIG. 4 by way of example) may act as the primary gateway for the user to interact with system 900. Medicament delivery device 915a may have an application running locally thereon (e.g., medicament delivery application 625, referencing FIG. 5B), such that medicament delivery application 625 acts as a secondary gateway for the user to interact with system 900. In some cases, analyte sensor system 308 may employ the intermittent connection model or another connection model discussed herein to share analyte data with analyte sensor application 425a and medicament delivery device 915a periodically. Additionally, medicament delivery device 915a may share medicament-related data with application 425, for example periodically per the intermittent connection model or using another connection model discussed herein.

It should be appreciated, however, that as between analyte sensor system 308 and analyte sensor application 425a/medicament delivery device 915a, on the one hand, and medicament delivery device 915a and analyte sensor application 425a, on the other hand, different connection models and advertisement structures may be employed. As such, inconsistencies may arise in the information that is provided via analyte sensor application 425a and medicament delivery application 625.

Accordingly, embodiments of the present disclosure include an integrative interface to share data between partner devices 915 and display devices 910, 910' within system 900. In some cases, this integrative interface is particularly useful when system 900 is operating in the hybrid operating mode described above. Coordinated sharing of information between display devices 910, 910' and partner devices 915 (e.g., medicament delivery device 915a) can improve insulin visualization, for example, including by providing enriched information such as alerts related to the working status of display devices 910, 910' and/or partner devices 915 and the like. In embodiments, the integrative interface is implemented as part of DMPI 750 (referencing FIG.

In embodiments, the integrative interface facilitates communications and the exchange of information between applications running on different devices within system 900. For example, and with reference to FIGS. 4 and 5B, analyte sensor application 425a that may run on mobile phone 910a may use such an integrative interface to communicate and exchange information with partner device application 425b and/or medicament delivery application 625 running on medicament delivery device 915a. In embodiments, analyte sensor application 425a may obtain (e.g., download and/or install) this interface from server system 334b (e.g., as may be maintained or serviced by the manufacturer of analyte sensor system 308, the provider of analyte sensor application 425a, the manufacturer of medicament delivery device 915a, and/or the provider of partner device application 425b or medicament delivery application 625), from another remote location (including, e.g., an app store or the like), or from medicament delivery device 915a.

Analyte sensor application 425a may then obtain information from medicament delivery device 915a or medicament delivery application 625 running thereon, including from or by way of partner device application 425b. Such information may include pairing/bonding data exchanged between analyte sensor system 308 and medicament delivery device 915a, historical data relating to medicament (e.g., insulin) dosage and the like provided by medicament delivery device 915a, or other information (e.g., user preferences for medicament delivery device 915a, medical information, alert information, etc.). Also, for example, alert information may be provided by partner device application 425b, medicament delivery application 625, and/or medicament delivery device 915a to analyte sensor application 425a, such that analyte sensor application 425a can then pass the alert information to the user. In this manner, alert information can essentially be funneled to the user and/or other systems or individuals monitoring the user, in a coordinated way, thus assisting in preventing the user from being bombarded by too many alerts from too many different (and in some cases overly redundant) sources. That is, analyte sensor application 425a may act as a hub for alerts stemming from different elements of system 900, and may control the propagation and distribution, as well as the escalation and acknowledgement processes associated with alerts, whether such alerts are related to analyte data or insulin data etc.

In addition, analyte sensor application 425a may be used to provide information to partner device application 425b, medicament delivery application 625, and/or medicament delivery device 915a. By way of example, such information may relate to analyte sensor system 308, including a working status thereof, mode of operation being employed, historical data relating to system operation, user preferences and other user-related information (e.g., other remote devices used for health management), and so forth. In some cases, certain data (e.g., analyte or EGV data etc.) may not be shared with partner device application 425b, medicament delivery application 625, and/or medicament delivery device 915a, for example where sharing such information would subject system 900 to regulations that may result in partner device application 425b, medicament delivery application 625, and/or medicament delivery device 915a, etc. being classified as a class 3 medical device. In other cases, however, such data may be shared.

In terms of communications between/among analyte sensor application 425a, partner device application 425b, and/or medicament delivery application 625 (referencing FIGS. 4 and 5B, for example), these applications can be linked together once they are obtained and installed. For example, a user may download one or more of these applications, and navigate through analyte sensor application 425a using user interface 435 to select another application for linking (e.g., partner device application 425b and/or medicament delivery application 625). For example, a particular menu of application 425a may be dedicated to linking with applications associated with partner devices 915 (e.g., applications 425b or 625). In embodiments, the applications may be linked automatically upon installation (with or without user approval, depending on the implementation), according to configuration(s)/settings that may be predetermined by the provider of analyte sensor application 425a, partner device application 425b and/or medicament delivery application 625.

Communications between/among analyte sensor application 425a, partner device application 425b, and/or medicament delivery application 625 may also be facilitated using remote services provided via server 920b. By way of illustration, medicament-related information and/or alerts stemming from medicament delivery device 915a may be uploaded to server 920b and then downloaded, for example, via analyte sensor application 425a running on mobile phone 910a (which, e.g., may belong to a user of analyte sensor system 308 or another individual monitoring the user's analyte data).

In embodiments, server(s) 920b maintained by a manufacturer of analyte sensor system 308 and/or provider of analyte sensor application 425a may include database of partner device applications 425b and/or medicament delivery applications 625 associated with manufacturers of partner devices 915 and/or providers of partner device applications 425b and/or medicament delivery applications 625. In this manner, the relevant application 425b, 625 may be obtained from server 920b once the manufacturer/provider is identified (e.g., using identification information exchanged during or after pairing between analyte sensor system 308 and medicament delivery device 915a).

It should also be appreciated that in embodiments, medicament delivery application 625 may have the interface and/or capability to communicate directly with medicament delivery device 915a only, and not with analyte sensor application 425a or analyte sensor system 308. In some such embodiments, medicament delivery device 915a may not include medicament delivery application 625, but instead medicament delivery device 915a may use partner device 425a running on mobile phone 910a and/or medicament delivery application 625 may run on partner device controller 645, for example. Thus, in example implementations, medicament delivery device 915a may receive information, including for example analyte data, EGV data, sensor data, etc., from analyte sensor system 308 and provide this information to medicament delivery application that is running on partner device controller 645.

In example implementations, partner device controller 645 that may be used in conjunction with medicament delivery device 915a may provide wireless connectivity to medicament delivery 915a (e.g., in some cases, medicament delivery device 915a may not include connectivity interface 605, which instead may be included in partner device controller 645).

In embodiments, the user may be provided (e.g., via analyte sensor application 425a, partner device application 425b, and/or medicament delivery application 625) the ability to implement a tradeoff between convenience and safety/accuracy regarding analyte data and the provision of medicaments, at least to a degree. For example, the user may be provided a degree of control over how expected/needed calibrations to analyte sensor system 308 may be alerted in the context of system 900. Features may thus be provided in accordance with embodiments to enable the user to flexibly strike a balance between care, safety, or quality of diabetes management, on the one hand, and convenience nuisance, and control/level of user interaction on the other hand. In example implementations, a sliding scale concept may enable the user to select different pre-set configurations of various configuration parameters 520 that can be used to govern accuracy, calibration, power management, as well as alerts. In certain situations, the user may, for convenience purposes, want to enable some flexibility in terms of the user's blood glucose levels, for example if the user has an important meeting or other event, the user may want to disable alerts or periodic calibrations. Configuration parameters 520 can be pre-set for such occasion, for example into modes that the user may select accordingly (e.g., meeting mode). It should be appreciated, however, that safety may require limitations on the degree of flexibility that a user may be provided. Such safety limitations may be user-specific, based on the user's medical information, profile, or data gathered over time.

With further reference to FIG. 9A by way of example, embodiments related to setting up implementations of system 900 that include display devices 910, 910' as well as partner devices 915 used for the delivery of medicaments, such as for example medicament delivery device 915a, will now be described. Such implementations of system 900 may include different devices from different manufacturers that are intended to interconnect and interoperate, and it may be advantageous to provide an easy and flexible set up procedure.

Accordingly, embodiments of the present disclosure are directed to facilitating the set up and initial configuration of such implementations of system 900. Some such embodiments include an integrated out-of-the-box experience, such that at least from the user's perspective, medicament delivery device 915a and analyte sensor system 308 and/or analyte sensor application 425a appear to be intended to work together. That is, for such embodiments, the set up process should be configured so that it does not feel like an assembly of unrelated parts. For example, a similar pairing process may be used as between display devices 910, 910' and analyte sensor system 308, on the one hand, and medicament delivery device 915a and analyte sensor system 308, on the other hand.

In embodiments, the user may be provided the option to arrange the order of setting up various devices within system 900. For example, the user may choose to first set up analyte sensor application 425a, then partner device application 425b and/or medicament delivery device 625, or vice versa. Additionally, in some cases the user may be able to select an option wherein applications for 425a and 425b are essentially merged into a single application that includes both the analyte data related features and the medicament delivery data features. In embodiments, the single application option may be enabled/facilitated by DMPI 750. The single application, as a merge of applications 425a and 425b may involve an integration of all the features offered by each application 425a and 425b. Using this option may streamline the set up process, since only a single application will be used.

In one example this single application option may be accomplished by the provider of analyte sensor application 425a providing a software design kit, including for example all the building blocks/features of analyte sensor application 425a, to a manufacturer of partner device 915 (e.g., medicament delivery device 915a) and/or the provider of partner device application 425b or medicament delivery application 625. In this manner, the provider may use the software design kit to incorporate the features of analyte sensor application 425a into partner device application 425b or medicament delivery application 625. In embodiments, the provider of analyte sensor system 308 and/or analyte sensor application 425a may maintain a database of analyte data related features (e.g., any feature implemented in connection with analyte sensor system 308 and/or analyte sensor application 425a), for example in server 920b (referencing FIG. 9A). The manufacturer of partner device 915 (e.g., medicament delivery device 915a) and/or the provider of partner device application 425b or medicament delivery application 625 may then access this database to obtain those software design kit for any feature of interest (e.g., a trend feature for analyzing/displaying a trend in analyte data values), provided that such a feature is accessible (e.g., permissions may be implemented to restrict access to certain features). The software design kit may be obtained (for example, downloaded) and used two designed the relevant feature into partner device application 425b or medicament delivery application 625.

Alternatively or additionally, the provider of partner device 915 (e.g., medicament delivery device 915a), partner device application 425b and/or medicament delivery application 625 may upload features related to partner device 915 (e.g., medicament delivery device 915a), partner device application 425b and/or medicament delivery application 625 two server 920b, for example. By way of illustration such features may include an insulin visualization tool, or the like. Display device 910, 910' may then directly or indirectly access server 920b to download the desired feature for inclusion in, for example analyte sensor application 425b. In some cases the provider of analyte sensor application 425b may create modules for incorporating downloadable code for implementing such features or the like so that features can essentially be implemented in a plug-and-play fashion, without requiring extensive user interaction.

During the setup process, user interface 435, with reference to FIG. 4, may indicate the progress/status of the set up. Additionally, options may be provided for the user to adapt the level of inter-activity involved in the setup process. For example, a power user may exercise the option to assert more control over configuration during the setup process.

In some cases, the setup process may be streamlined where common set of features applied to a first device/application may be conveyed to a second device/application, thus enabling such common aspects to be bypassed when the second device/application set up process occurs. The set up for such common features may be conveyed among different devices using a mutual connection path or link within system 900, since in some instances to devices may not be able to connect directly until after the set up process is completed. Here it should be noted that analyte sensor application 425a may be able to use DMPI 752 access configuration parameters 520 and configure the same in accordance with system requirements 650 of medicament delivery device 915a in response to information identifying medicament delivery device 915a. By way of example and identification number or other identifying information associated with medicament delivery device 915a may be used to identify predetermined, customizable settings for medicament delivery device 915a, and these settings may be implemented my application 425a using DMPI 750 to modify or set configuration parameters 520 according to the settings. Furthermore, such identifying information may be used to encrypt analyte data transmitted to medicament delivery device 915a etc.

Additional embodiments concerning the integration of features across system 900 may involve, for example, features implemented in connection with services that may be provided via servers 920b. Such services may allow other individuals or entities, such as medical professionals, healthcare equipment, friends, and family, to monitor or follow a user with respect to the user's analyte data and/or medicament data generated using analyte sensor system 308 and/or medicament delivery device 915a. In this manner, for example the users blood glucose level or insulin delivery can be monitored by others, for safety purposes. In connection with this monitoring, alerts may be provided to those individuals or entities following the user.

With general reference by way of example to FIG. 9A and system 900, the user may can figure what aspects of analyte data and/or medicament data are exposed to the user's followers. In this connection, the user may set different permissions for different followers, such that certain followers may be able to have greater access to certain data, and may be able to respond to alerts in different ways. In some cases, default permissions may be implemented based on a category of the follower, for example, friends and family may be defaulted to have a first set of permissions, caretakers may be defaulted to have a second set of permissions, and hospitals or doctors may be defaulted to have ⅓ set of permissions.

Another aspect of configuring permissions may use a type of device that is performing the monitoring. By way of example, more restrictive permissions may be set for a follower's television which is more widely visible to other people besides the follower, while less restrictive permissions may be set for a follower's phone or computer. That is, in embodiments the user may customize permissions according to a desired level of privacy. The permissions may also be set in an adaptable manner using location-based information such as whether the setting is private or public, e.g., a restaurant versus a home. In some cases, the permissions may be adaptively set based on the follower's time zone (e.g., if the time zone indicates that the follower might be asleep, the alert can be configured to wake up the follower). Yet another aspect of configuring a follower's access to analyte and/or medicament data and associated alerts may be related to the mode of the device used to follow the user. For example a follower's device may be on silent or airplane mode or do not disturb, but in case of an emergency, as reflected by the analyte and/or medicament data and/or the alert itself, the device setting may be overridden and the alert provided notwithstanding that for example the device is in airplane mode. Additionally the follower's device, if it is in a mode where alerts are not receivable, may so indicate such that for example an alternative means of notifying the follower may be attempted such alternative means may be an email alert or a landline call placed using the follower's device location.

With further regard to services that may be provided via server 920b, in embodiments the availability of access to server 920b through WAN 904 may serve as an input to setting or modifying configuration parameters 520 of analyte sensor system 308. For example analyte sensor system 308 may determine the availability of a connection, whether direct or indirect, to server 920b (e.g., via mobile phone 910a and cell network 920c, router 920a, etc.) in PAN 902. Using the determination, configuration parameters 520 may then be set/modified, for example, to configure the types of alerts that may be employed vis-à-vis analyte and/or medicament data. As cloud services increase in ubiquity, the ability to adaptively utilize such services becomes increasingly advantageous.

Some examples of services that may be provided via WAN 904, including for example servers 920b, will now be discussed. As mentioned, a service that may be provided via WAN 904 involves followers of a user of analyte sensor system 308. Such followers may utilize WAN 904 to connect an electronic device such as a smart phone, television, computer, and the like to PAN 902 and thus receive relevant analyte, medicament delivery, and/or other information related to the use of analyte sensor system 308 and/or the use of medicament delivery device 915a. The follower's electronic device may run an application specifically designed for following the user of analyte sensor system 308 and/or medicament delivery device 915a. This application may then be used on the follower's electronic device to provide alerts, for example the various alerts described above, insulin values, insulin visualization, CGM values, trends, etc.

In embodiments, additional cloud services that may be provided via WAN 904 may involve services provided to the user of analyte sensor system 308 and/or medicament delivery device 915a. By way of example, analyte sensor application 425a, partner device application 425b, and/or medicament delivery application 625 (referencing, for example, FIGS. 4, 5B, 6) may provide web links to tutorials, help files, or videos relating to the use and/or set up of analyte sensor system 308 or medicament delivery device 915a. Such tutorials, help files, or videos may be provided by the respective manufacturers of analyte sensor system 308 or medicament delivery device 915a, or may be provided by others, for example other users.

Another example of a cloud service that may be provided via WAN 904 may involve obtaining settings or system requirements 650 for medicament delivery device 915a that may be specific to the user of system 900. Such settings or system requirements 650 may have been determined by the user's healthcare provider, and may include, for example, one or more of a basal infusion rate, insulin to carb ratio, and the like. These settings or system requirements 650 may be communicated to the user via WAN 904, and may, using DMPI 750, be used to set/modify configuration parameters 520 of analyte sensor system 308.

In one example, the healthcare provider may upload those settings or system requirements 650 to WAN 904. Subsequently, the user may access these settings or system requirements 650 via server 920b, and can download the settings or system requirements 650 for automatic implementation via setting or modifying configure right patient parameters 520 (for example, the download may be direct from server 920b to analyte sensor system 308 or may utilize an intermediate device connectable to WAN 904, such as for example mobile phone 910a or other display device 910, 910'). In this particular example, server 920b (or software implemented in or in connection with server 920b) may periodically (for example, weekly/monthly) gather information related to medicament delivery and analyte data (e.g., insulin and glucose data). Server 920b and/or software implemented in association there with may then analyze the information and determine whether modifications to settings, system requirements 650, and/or configuration parameters 520 may be more effective for the user, including in some cases considering the user's lifestyle and/or health goals.

M. Additional Embodiments

One of skill in the art will appreciate upon studying the present disclosure that various additional embodiments not described explicitly herein are within the spirit and scope of the present disclosure.

Figure 11:
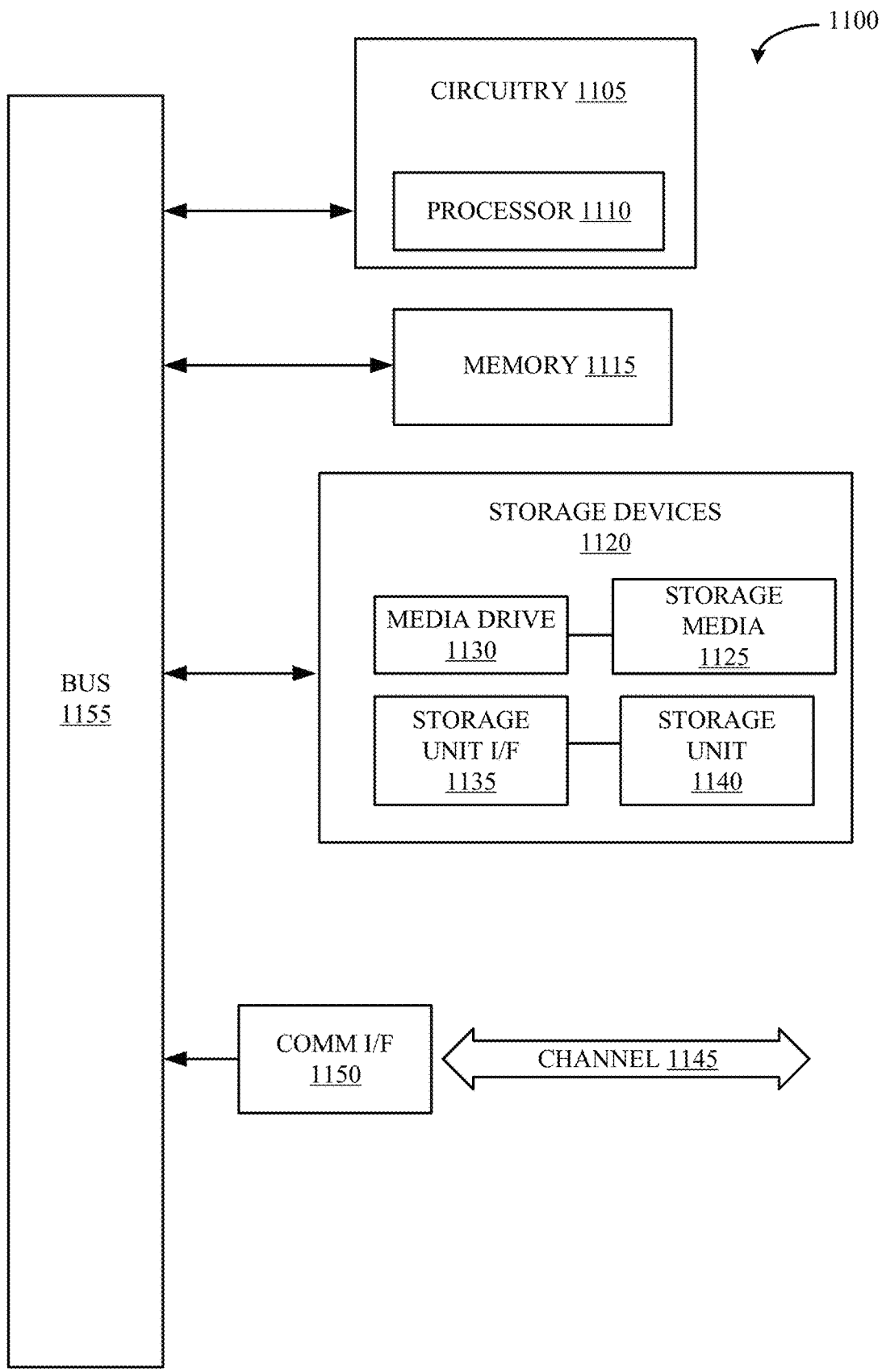
FIG. 11 illustrates an example computing module in accordance with embodiments of the present disclosure.

FIG. 11 illustrates example computing module 1100, which may in some instances include a processor/microprocessor/controller resident on a computer system (e.g., in connection with server system 334, any of the display devices described herein (e.g., display devices 120, 130, 140, 310(a, b, etc.), 910(a, b, etc.), partner devices 315(a, b, etc.), 915(a, b, etc.), and/or analyte sensor system 8, 308, etc. Computing module 1100 may be used to implement various features and/or functionality of embodiments of the systems, devices, apparatuses, and methods disclosed herein. With regard to the above-described embodiments set forth herein in the context of systems, devices, apparatuses, and methods described with reference to the various FIGS. of the present disclosure, including embodiments of analyte sensor system 308, display device 310, 910, etc., partner devices 315, 915, etc., server system 334, 334a, 334b, servers 920b, and components of the foregoing as described and/or contemplated herein, etc., one of skill in the art will appreciate upon studying the present disclosure the additional variations and details regarding the functionality of these embodiments that may be carried out by computing module 1100. In this connection, it will also be appreciated by one of skill in the art upon studying the present disclosure that features and aspects of the various embodiments (e.g., systems, devices, and/or apparatuses, and the like) described herein may be implemented with respected to other embodiments (e.g., methods, processes, and/or operations, and the like) described herein without departing from the scope or spirit of the disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In implementation, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 11. Various embodiments are described in terms of example computing module 1100. After reading this description, it will become apparent to a person skilled in the relevant art how to implement the application using other computing modules or architectures.

Referring now to FIG. 11, computing module 1100 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); other display devices, application-specific devices, or other electronic devices, and the like, depending on the application and/or environment for which computing module 1100 is specifically purposed.

Computing module 1100 may include, for example, one or more processors, microprocessors, controllers, control modules, or other processing devices, such as a processor 1110, and such as may be included in circuitry 1105. Processor 1110 may be implemented using a special-purpose processing engine such as, for example, a microprocessor, controller, or other control logic. In the illustrated example, processor 1110 is connected to bus 1155 by way of circuitry 1105, although any communication medium may be used to facilitate interaction with other components of computing module 1100 or to communicate externally.

Computing module 1100 may also include one or more memory modules, simply referred to herein as main memory 1115. For example, random access memory (RAM) or other dynamic memory may be used for storing information and instructions to be executed by processor 1110 or circuitry 1105. Main memory 1115 may also be used for storing temporary variables or other intermediate information during execution of instructions to be executed by processor 1110 or circuitry 1105. Computing module 1100 may likewise include a read only memory (ROM) or other static storage device coupled to bus 1155 for storing static information and instructions for processor 1110 or circuitry 1105.

Computing module 1100 may also include one or more various forms of information storage devices 1120, which may include, for example, media drive 1130 and storage unit interface 1135. Media drive 1130 may include a drive or other mechanism to support fixed or removable storage media 1125. For example, a hard disk drive, a floppy disk drive, a magnetic tape drive, an optical disk drive, a CD or DVD drive (R or RW), or other removable or fixed media drive may be provided. Accordingly, removable storage media 1125 may include, for example, a hard disk, a floppy disk, magnetic tape, cartridge, optical disk, a CD or DVD, or other fixed or removable medium that is read by, written to or accessed by media drive 1130. As these examples illustrate, removable storage media 1125 may include a computer usable storage medium having stored therein computer software or data.

In alternative embodiments, information storage devices 1120 may include other similar instrumentalities for allowing computer programs or other instructions or data to be loaded into computing module 1100. Such instrumentalities may include, for example, fixed or removable storage unit 1140 and storage unit interface 1135. Examples of such removable storage units 1140 and storage unit interfaces 1135 may include a program cartridge and cartridge interface, a removable memory (for example, a flash memory or other removable memory module) and memory slot, a PCMCIA slot and card, and other fixed or removable storage units 1140 and storage unit interfaces 1135 that allow software and data to be transferred from removable storage unit 1140 to computing module 1100.

Computing module 1100 may also include a communications interface 1150. Communications interface 1150 may be used to allow software and data to be transferred between computing module 1100 and external devices. Examples of communications interface 1150 include a modem or soft-modem, a network interface (such as an Ethernet, network interface card, WiMedia, IEEE 802.XX or other interface), a communications port (such as for example, a USB port, IR port, RS232 port Bluetooth® interface, or other port), or other communications interface configured to operation with the communication media described herein. Software and data transferred via communications interface 1150 may in examples be carried on signals, which may be electronic, electromagnetic (which includes optical) or other signals capable of being exchanged by a given communications interface 1150. These signals may be provided to/from communications interface 1150 via channel 1145. Channel 1145 may carry signals and may be implemented using a wired or wireless communication medium. Some non-limiting examples of channel 1145 include a phone line, a cellular or other radio link, an RF link, an optical link, a network interface, a local or wide area network, and other wired or wireless communications channels.

In this document, the terms "computer program medium" and "computer usable medium" and "computer readable medium", as well as variations thereof, are used to generally refer to transitory or non-transitory media such as, for example, main memory 1115, storage unit interface 1135, removable storage media 1125, and/or channel 1145. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module 1100, circuitry related thereto, and/or a processor thereof or connected thereto to perform features or functions of the present disclosure as discussed herein (for example, in connection with methods described above and/or in the claims), including for example when the same is/are incorporated into a system, apparatus, device and/or the like.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; the term "set" should be read to include one or more objects of the type included in the set; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Similarly, the plural may in some cases be recognized as applicable to the singular and vice versa. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic, circuitry, or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration. Moreover, the operations and sub-operations of various methods described herein are not necessarily limited to the order described or shown in the figures, and one of skill in the art will appreciate, upon studying the present disclosure, variations of the order of the operations described herein that are within the spirit and scope of the disclosure.

In addition, the operations and sub-operations of methods described herein may be carried out or implemented, in some cases, by one or more of the components, elements, devices, modules, circuitry, processors, etc. of systems, apparatuses, devices, environments, and/or computing modules described herein and referenced in various of FIGS. of the present disclosure, as well as one or more sub-components, elements, devices, modules, processors, circuitry, and the like depicted therein and/or described with respect thereto. In such instances, the description of the methods or aspects thereof may refer to a corresponding component, element, etc., but regardless of whether an explicit reference is made, one of skill in the art will recognize upon studying the present disclosure when the corresponding component, element, etc. may be used. Further, it will be appreciated that such references do not necessarily limit the described methods to the particular component, element, etc. referred to. Thus, it will be appreciated by one of skill in the art that aspects and features described above in connection with (sub-) components, elements, devices, modules, and circuitry, etc., including variations thereof, may be applied to the various operations described in connection with methods described herein, and vice versa, without departing from the scope of the present disclosure.

What is claimed is:

1. A system comprising:
a display device and a partner device, the display device configured to provide information regarding analyte values in a user's body and in wireless communication with an analyte sensor system and the partner device, wherein the partner device is an insulin delivery device and is not directly connected to the analyte sensor system, and wherein:
the display device receives analyte data from the analyte sensor system;
the partner device delivers insulin to a user based on analyte data generated using the analyte sensor system, or data derived therefrom, that is received from the display device;
the display device alerts the user and provides analyte data received from the analyte sensor system; and
the display device provides information relating to delivery of insulin by the partner device.

2. The system of claim 1, wherein the display device has an analyte sensor application thereon that is configured to receive medicament-related data from the insulin delivery device and the display device is further configured to provide the medicament-related data to the user.

3. The system of claim 2, wherein the analyte sensor application is configured to receive the medicament-related data periodically from the insulin delivery device using a continuous connection model.

4. The system of claim 1, wherein the display device has an analyte sensor application thereon, wherein the display device is further configured to store volumes of analyte-related data received from analyte sensor system and volumes of medicament-related data received from the insulin delivery device, and wherein the analyte sensor application is configured to receive input and allow a user to interact with the analyte-related data and medicament-related data via a graphical user interface of the display device.

5. The system of claim 1, wherein the display device is further configured to trigger alerts based on events or conditions detected at the insulin delivery device.

6. The system of claim 5, wherein the display device is configured to trigger an alert if the display device determines that the insulin delivery device has a mechanical or other failure.

7. The system of claim 1, wherein the display device is further configured to trigger an alert based on characteristics of the analyte data generated using the analyte sensor system.

8. The system of claim 7, wherein the alert is a hypoglycemic alert that is triggered based on alert conditions indicating a minimum glucose level or based on alert conditions indicating a minimum required trend is present in the user's glucose level.

9. The system of claim 1, wherein the display device is configured to communicate with the analyte sensor system using a continuous connection model which involves the display device performing an initial pairing with the analyte sensor system, after which the display device remains connected to the analyte sensor system by periodically exchanging messaging with the analyte sensor system to maintain the connection.

10. The system of claim 9, wherein the display device is configured to communicate with the analyte sensor system according to the continuous connection model by:
receiving advertisement messages transmitted by the analyte sensor system;
establishing a connection with the analyte sensor system;
periodically exchanging data with the analyte sensor system; and
periodically exchanging ping messaging with the analyte sensor system to maintain the connection.

11. The system of claim 9, wherein the display device is further configured such that, upon the display device becoming disconnected from the analyte sensor system, the user receives a notification via the display device that the connection has been lost.

12. The system of claim 1, wherein the display device is further configured to utilize a wide area network (WAN) to provide at least one of analyte information, medicament delivery information or information related to use of the insulin delivery device to an electronic device of a follower of the user of the analyte sensor system.

13. The system of claim 12, wherein the system further comprises the electronic device of the follower, and wherein the electronic device of the follower runs an application specifically designed for following the user.

14. The system of claim 13, wherein the application on the electronic device of the follower provides one or more of alerts, insulin values, insulin visualization and continuous glucose monitoring (CGM) values.

15. The system of claim 12, wherein the analyte information is glucose data, and the medicament delivery information is insulin data.

16. The system of claim 1, wherein the partner device is configured to deliver insulin to a user based on analyte data generated using the analyte sensor system, or data derived therefrom, by delivering a bolus of insulin to a user based on one or more bolus calculation parameters.

17. The system of claim 16, wherein the partner device is provided access to the one or more bolus calculation parameters.

* * * * *